US007326562B2

(12) United States Patent
Felkner et al.

(10) Patent No.: US 7,326,562 B2
(45) Date of Patent: Feb. 5, 2008

(54) BIOLOGICAL INDICATOR SYSTEM TO DETECT EFFECTIVENESS OF STERILIZATION

(75) Inventors: Ira C. Felkner, West Palm Beach, FL (US); Joseph P. Laico, New City, NY (US)

(73) Assignee: ICF Technologies, Inc., New City, NY (US)

( * ) Notice: Subject to any disclaimer, the term of this patent is extended or adjusted under 35 U.S.C. 154(b) by 95 days.

(21) Appl. No.: 11/281,107

(22) Filed: Nov. 17, 2005

(65) Prior Publication Data

US 2006/0183183 A1  Aug. 17, 2006

Related U.S. Application Data

(63) Continuation of application No. 10/720,576, filed on Nov. 24, 2003, now abandoned, which is a continuation of application No. 10/091,260, filed on Mar. 4, 2002, now Pat. No. 6,942,989, which is a continuation-in-part of application No. 09/563,707, filed on May 2, 2000, now abandoned.

(60) Provisional application No. 60/132,186, filed on May 3, 1999.

(51) Int. Cl.
*C12M 1/34* (2006.01)
(52) U.S. Cl. ................... 435/287.4; 435/31
(58) Field of Classification Search ............ 435/31, 435/287.4
See application file for complete search history.

(56) References Cited

U.S. PATENT DOCUMENTS

| | | | |
|---|---|---|---|
| 3,440,144 A | 4/1969 | Andersen | |
| 3,730,842 A | 5/1973 | Wyatt et al. | |
| 3,770,351 A | 11/1973 | Wyatt | |
| 3,815,000 A | 6/1974 | Phillips et al. | |
| 3,968,250 A | 7/1976 | Boucher | |
| 4,101,383 A | 7/1978 | Wyatt et al. | |
| 4,140,018 A | 2/1979 | Maldarelli et al. | |
| 4,173,415 A | 11/1979 | Wyatt | |
| 4,416,984 A | 11/1983 | Wheeler, Jr. | |
| 4,461,837 A | 7/1984 | Karle et al. | |
| 4,528,268 A | 7/1985 | Andersen et al. | |
| 4,541,719 A | 9/1985 | Wyatt | |
| 4,548,500 A | 10/1985 | Wyatt et al. | |
| 4,596,773 A | 6/1986 | Wheeler, Jr. | |
| 4,616,927 A | 10/1986 | Phillips et al. | |
| 4,621,063 A | 11/1986 | Wyatt et al. | |
| 4,693,602 A | 9/1987 | Wyatt et al. | |
| 4,710,025 A | 12/1987 | Wyatt et al. | |
| 4,717,661 A | 1/1988 | McCormick et al. | |
| 4,810,875 A | 3/1989 | Wyatt | |
| 4,907,884 A | 3/1990 | Wyatt et al. | |
| 4,952,055 A | 8/1990 | Wyatt | |
| 5,073,488 A | 12/1991 | Matner et al. | |
| 5,129,723 A | 7/1992 | Howie et al. | |
| D329,821 S | 9/1992 | Wyatt et al. | |
| 5,167,923 A | 12/1992 | Van Iperen | |
| 5,186,946 A | 2/1993 | Valliéres | |
| 5,223,401 A | 6/1993 | Foltz et al. | |
| 5,252,484 A | 10/1993 | Matner et al. | |
| 5,305,071 A | 4/1994 | Wyatt | |
| 5,366,872 A | 11/1994 | Hird et al. | |
| 5,405,580 A | 4/1995 | Palmer | |
| 5,486,459 A | 1/1996 | Burnham et al. | |
| 5,498,526 A | 3/1996 | Caputo et al. | |
| 5,500,184 A | 3/1996 | Palmer | |
| 5,516,648 A | 5/1996 | Malchesky et al. | |
| 5,530,540 A | 6/1996 | Wyatt et al. | |
| 5,552,320 A | 9/1996 | Smith | |
| 5,616,457 A | 4/1997 | Garcia-Rubio | |
| 5,620,656 A | 4/1997 | Wensky et al. | |
| 5,736,355 A | 4/1998 | Dyke et al. | |
| 5,739,004 A | 4/1998 | Woodson | |
| 5,750,184 A | 5/1998 | Imburgia | |
| 5,770,393 A | 6/1998 | Dalmasso et al. | |
| 5,795,730 A * | 8/1998 | Tautvydas | 435/31 |
| 5,801,010 A | 9/1998 | Falkowski et al. | |
| 5,808,738 A | 9/1998 | Garcia-Rubio | |
| 5,876,960 A | 3/1999 | Rosen | |
| 6,187,555 B1 | 2/2001 | Tautvydas | |
| 6,207,215 B1 | 3/2001 | Wilson et al. | |
| 6,287,518 B1 | 9/2001 | Ignacio et al. | |
| 6,942,989 B2 * | 9/2005 | Felkner et al. | 435/31 |

OTHER PUBLICATIONS

Anderson, E.M. et al. "Potential Application of LASER/Microbe Bioassay Technology for Determining Water-Soluble Vitamins in Foods" *Journal of AOAC International*, vol. 76, No. 3, pp. 682-690 (1993).

Felkner, I.C et al., Ed. Marcel Dekker, Inc., "Development of A *B.Sutilis* System to Screen Carcinogens/Mutagens: DNA-Damaging and Mutation Assays", *Microbiology Series; Microbial Testers: Probing Carcinogenesis*, NY, vol. 5, pp. 93-119 (1981).

Felkner, I.C., Ed. Marcel Dekker, Inc., "Microbial Assay Construction: Rationale, Specificity, and Utility," *Microbiology Series; Microbial Testers: Probing Carcinogenesis*, NY, vol. 5, Part 2, pp. 89-91 (1981).

(Continued)

*Primary Examiner*—Ralph Gitomer
(74) *Attorney, Agent, or Firm*—Flaster/Greenberg P.C.

(57) ABSTRACT

A novel biological indicator system to detect the effectiveness of a sterilization treatment for assessing the viability of and/or changes in bacterial spores exposed to sterilization or disinfection by multi-angle light scattering thereby detecting a change in the spores as indicators of spore viability and the efficacy of the sterilization or disinfection.

10 Claims, 25 Drawing Sheets

OTHER PUBLICATIONS

Felkner, I.C. et al. "Newest Approaches to Quantitative Assessment of Bioactive Organotins" *Science and Technology Letters*, vol. 1, No. 3, pp. 79-92 (Oct. 1989).

Molina-Garcia A. et al., "Dynamic Light Scattering Studies on the Effect of Heat and Disinfectants on Spores of *Bacillus cereus*", *Biochem J.*, vol. 263, No. 3, pp. 883-888 (1989).

Shahamat, M. et al., "Bacterial Retention By Membrane Filters"; Abstract for American Society for Microbiology Meeting, Chicago, IL., One Page (Jun. 1, 1999).

Wyatt P., "Differential Light Scattering: A Physical Method for Identifying Live Bacteria Cells", *Applied Optics.*, vol. 7, No. 10, pp. 1879-1896 (Oct. 1968).

\* cited by examiner

RESULTS PROBLEM No:   Time 2 hours
ESTIMATES FOR A SINGLE POPULATION
Mie Average Diameter (cm) = 2.570334E-04 +/- 3.302753E-05
Concentration (g/mL) meas. = 2.028209E-06
Concentration (g/mL) calc. = 2.028209E-06 +/- 2.261741E-07
Particle No (#/mL)         = 228110.500000

Residual sum of squares    = 5.012901E-05
Res. sum of squares (Norm) = 2.879399E-01
Standard Dev. (Residuals)  = 3.019001E-04
Standard Dev. (Norm. Res)  = 2.288071E-02

RESULTS PROBLEM No:   Time 3 hours
ESTIMATES FOR A SINGLE POPULATION
Mie Average Diameter (cm) = 2.672413E-04 +/- 7.599205E-06
Concentration (g/mL) meas. = 9.346907E-06
Concentration (g/mL) calc. = 9.346907E-06 +/- 2.200983E-07
Particle No (#/mL)         = 935316.800000

Residual sum of squares    = 2.789136E-03
Res. sum of squares (Norm) = 7.187017E-01
Standard Dev. (Residuals)  = 2.251923E-03
Standard Dev. (Norm. Res)  = 3.614872E-02

RESULTS PROBLEM No:   Time 4 hours
ESTIMATES FOR A SINGLE POPULATION
Mie Average Diameter (cm) = 1.969644E-04 +/- 1.826982E-06
Concentration (g/mL) meas. = 3.055250E-05
Concentration (g/mL) calc. = 3.055250E-05 +/- 2.933861E-07
Particle No (#/mL)         = 7636334.000000

Residual sum of squares    = 5.679470E-03
Res. sum of squares (Norm) = 2.113989E-01
Standard Dev. (Residuals)  = 3.213458E-03
Standard Dev. (Norm. Res)  = 1.960514E-02

RESULTS PROBLEM No:   Time 5 hours
ESTIMATES FOR A SINGLE POPULATION
Mie Average Diameter (cm) = 1.405828E-04 +/- 1.859756E-06
Concentration (g/mL) meas. = 2.712445E-05
Concentration (g/mL) calc. = 2.712445E-05 +/- 4.164035E-07
Particle No (#/mL)         = 1.864516E+07

Residual sum of squares    = 9.585535E-04
Res. sum of squares (Norm) = 8.134952E-02
Standard Dev. (Residuals)  = 1.320161E-03
Standard Dev. (Norm. Res)  = 1.216175E-02

Fig. 16

BIOLOGICAL INDICATOR SYSTEM TO DETECT EFFECTIVENESS OF STERILIZATION

CROSS-REFERENCE TO RELATED APPLICATIONS

This application is a continuation of pending U.S. patent application Ser. No. 10/720,576, filed Nov. 24, 2003, now abandoned, which is a continuation of U.S. patent application Ser. No. 10/091,260, filed Mar. 4, 2002, now U.S. Pat. No. 6,942,989, which is a continuation-in-part of prior U.S. patent application Ser. No. 09/563,707, filed May 2, 2000, now abandoned which claims the benefit under 35 U.S.C. § 119(e) of U.S. Provisional Patent Application No. 60/132,186, filed May 3, 1999, the contents of each of which are incorporated herein by reference.

BACKGROUND OF THE INVENTION

The present invention relates to biological indicators of sterilization and disinfection.

Primarily in the health care industry, but also in many other industrial applications, it is nearly always necessary to monitor the effectiveness of the processes used to sterilize equipment such as medical and non-medical devices, instruments and other articles and materials. In these settings, sterilization is generally defined as the process of completely destroying viable microorganisms including structures such as viruses and spores. Standard practice in these health care facilities is to include a sterility indicator in the batch of articles to be sterilized. The use of sterility indicators allows a direct and sensitive approach to assay the lethality of the sterilization process.

A standard type of biological sterility indicator includes a presumably known quantity of test microbial spores. This indicator is placed into the sterilization chamber and exposed to the sterilization process along with the objects to be sterilized. The test microorganisms, for example *Bacillus stearothermophilus* or *B. subtilis* spores, are then contacted with a growth medium and incubated for a specified period of time under conditions which favor proliferation and examined for possible growth, as determined by the presence or absence of certain metabolic products, of any surviving microorganisms. Positive growth indicates that the sterilization process was insufficient to destroy all of the microorganisms. While a wide variety of apparatuses for containing the spores have been developed, there are few variations in the general sterility detection process.

Prior biological indicators disclosed in existing patents contain a preparation of viable spores made from a culture derived from a specific bacterial strain and characterized for predictable resistance to sterilization. Spores of bacteria are often the test organism in conventional biological indicators because they are much more resistant to the sterilization process than most other organisms. Many of the prior art biological indicators are self-contained, meaning that they possess the spores and the incubation media in a single container but typically in separate compartments. Following sterilization, the container is processed so that the spores come into contact with the growth media. The entire container is then incubated for a specific time and the results determined and recorded.

Alternatively, some biological indicators are comprised of spores on a carrier in a package. After being exposed to the sterilization process, the carrier with the spores is transferred from the package to sterile media and incubated.

A major drawback of all these sterility indicators is the time delay in obtaining results of the sterility test. These sterility indicators normally require that the microorganisms be cultured for at least two and often up to seven days to assure adequate detection of any surviving microorganisms. During this time, the items which went through the sterilization process should not be used until the results of the spore viability test have been determined. A viable spore result indicates that proper sterilization conditions were not met.

Many health care facilities have limited resources and must reuse their "sterilized" instruments within 24-48 hours and often immediately. In such settings, the three to seven day holding period for sterility verification is impractical, costly and inefficient.

There are even further time delays and costs necessitated by these traditional commercial biological indicators because technicians must be trained and clean room facilities must be made available in order to determine the viability of the biological indicators using standard microbiological techniques.

Further, most of the conventional growth tests are performed in test facilities outside the medical or dental offices where the sterile instruments are used and prepared, thereby further compounding the costs and delay in obtaining the test results.

The use of an enzyme and its subsequent activity as an indicator in an attempt to overcome the time delay in detecting sterility has also been described previously. While obviating the need for complex sample handling and decreasing the processing time required by biological indicators, the use of enzyme, or multiple enzymes, also have disadvantages. For example, the specialized equipment is often necessary to detect the product made by a single enzyme. Additionally, the use of a single or multiple enzymes does not effectively recreate the response of a complex, living organism to a sterilization process. Thus, the response of an enzyme or enzymes to a sterilization treatment may not properly reflect efficacy of sterilization with respect to biological organisms. That is, although thermostable enzymes may be useful in determining the effectiveness of a sterilization process, they do not provide the same degree of sterilization assurance as do live bacterial spores as biological indicators. Because the activity of a thermostable enzyme can only be correlated with spore death, the degree of inactivation of such an enzyme may not accurately measure the effect of the sterilization process on a living organism in all instances. Low numbers of surviving organisms may not produce sufficient enzyme to break down the indicator substrate so that a color change or colorimetric reading is registered, thereby giving a false negative. Furthermore, the enzyme assay does not function for cold sterilization treatments.

Therefore, there is a need for a biological indicator and methods for the use thereof to accurately detect the efficacy of a sterilization treatment which indicator does not require complex processing and which yields rapid results, i.e., results are obtained in a matter of hours instead of days. The present invention meets this need.

BRIEF SUMMARY OF THE INVENTION

The invention includes a system for detecting the effectiveness of a sterilization treatment. The system comprises a biological indicator, a solid support, a liquid medium, and a multiangle light scattering instrument.

In one aspect, the biological indicator is a spore selected from the group consisting of a *B. subtilis* spore, and a *B. stearothermophilus* spore.

In another aspect, the solid support is selected from the group consisting of an adsorbent filter, a membrane, a matrix, glass, plastic, and metal.

In yet another aspect, the multi angle light scattering instrument is selected from the group consisting of a DAWN Model B MALS photometer, and a DAWN Model F MALS photometer.

In another aspect, the sterilization treatment is selected from the group consisting of a chemical sterilization treatment, and a physical sterilization treatment.

In yet another aspect, the liquid medium is selected from the group consisting of water, a brain heart infusion broth medium, a nutrient broth, and a trypticase soy broth.

The invention also includes a method of assessing the viability of a spore after a sterilization treatment. The method comprises:

(a) exposing a spore to a sterilization treatment;
(b) examining the treated spore using multiangle light scattering; and
(c) evaluating a difference between the multiangle light scattering of the treated spore and a multiangle light scattering of a like spore not exposed to a sterilization treatment to determine whether the treated spore is viable.

In one aspect, the spore and the like spore are selected from the group consisting of a *B. subtilis* spore, and a *B. stearothermophilus* spore.

In another aspect, the sterilization treatment is selected from the group consisting of a chemical sterilization treatment, and a physical sterilization treatment.

In yet another aspect, the chemical sterilization treatment is selected from the group consisting of an ethylene oxide sterilization treatment, a hydrogen peroxide sterilization treatment, a tetrasilver tetraoxide sterilization treatment, and an ozone sterilization treatment.

In a further aspect, the physical sterilization treatment is selected from the group consisting of a radiation sterilization treatment, a gas plasma sterilization treatment, a steam sterilization treatment, and a dry heat sterilization treatment.

In another aspect, the method further comprises examining the like spore using multiangle light scattering prior to the sterilization treatment of the spore in step (a) to provide a standard multiangle light scattering data set for use as the multiangle light scattering of the like spore in step (c).

In yet another aspect, the method further comprises storing the standard multiangle light scattering data to assess viability of a second like spore after sterilizing the second like spore using the sterilization treatment of step (a).

In another aspect, the method further comprises incubating the treated spore with a growth medium prior to step (b).

In yet another aspect, the growth medium is selected from the group consisting of trypticase soy broth, nutrient broth, and brain heart infusion broth.

In another aspect, the method further comprises incubating the spore up to about 24 hours prior to step (b).

In yet another aspect, the method further comprises heat-shocking the treated spore prior to incubating the treated spore with the growth medium.

In another aspect, the sterilization treatment is selected from the group consisting of a steam sterilization treatment, and an ozone sterilization treatment, and the method further comprises examining the treated spore directly after the sterilization treatment.

The invention includes a method of assessing the efficacy of a sterilization treatment. The method comprises:

(a) exposing a biological indicator to a sterilization treatment;
(b) examining a like biological indicator using multiangle light scattering to create a standard profile;
(c) examining the treated biological indicator using multiangle light scattering to create a post-sterilization profile; and
(d) comparing the post-sterilization profile of the treated biological indicator to the standard profile of the like biological indicator, wherein a difference between the post-sterilization profile of the treated biological indicator and the standard profile of the like biological indicator indicates the efficacy of the sterilization treatment.

In one aspect, the biological indicator and the like biological indicator are *B. subtilis* spores.

In another aspect, the method further comprises using a photometer selected from the group consisting of a DAWN Model B MALS photometer, and a DAWN Model F MALS photometer for multiangle light scattering.

In yet another aspect, the sterilization treatment is selected from the group consisting of a physical sterilization treatment, and a chemical sterilization treatment.

In another aspect, the sterilization treatment is selected from the group consisting of a steam sterilization treatment, and an ozone sterilization treatment, and the method further comprises examining the treated spore directly after the sterilization treatment.

The invention includes a method of detecting a change in a biological indicator exposed to a sterilization treatment. The method comprises exposing a biological indicator to a sterilization treatment, and comparing a multiangle light scattering of the treated biological indicator to a multiangle light scattering of a like biological indicator not exposed to a sterilization treatment, wherein a difference between the multiangle light scattering of the treated biological indicator and the multiangle light scattering of the like biological indicator indicates a change in the treated biological indicator.

In one aspect, the method further comprises incubating the treated biological indicator with a growth medium for up to about 24 hours before examining the multiangle light scattering of the biological indicator.

In another aspect, the method further comprises heat-shocking the biological indicator prior to incubating the biological indicator with the growth medium.

In yet another aspect, the method further comprises using an instrument selected from the group consisting of a nephelometer, and a photometer to examine the multiangle light scattering of the biological indicator.

In another aspect, the sterilization treatment is selected from the group consisting of a steam sterilization treatment, and an ozone sterilization treatment, and the method further comprises examining the treated spore directly after the sterilization treatment.

The invention also includes a kit for assessing the viability of a spore after a sterilization treatment. The kit comprises about $2 \times 10^8$ spores adsorbed onto a solid support, a multiangle light scattering photometer, and a liquid medium.

In one aspect, the kit further comprises an instructional material for the use of the kit.

BRIEF DESCRIPTION OF THE SEVERAL
VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 1 is a graph depicting the measurements made by multi-angle light scattering (MALS) of *B. subtilis* untreated but heat-shocked spores (Control) at selected brain heart infusion (BHI) culture incubation intervals of 0 minutes (set 1), 30 minutes (set 6), 2 hours (set 16), and 4 hours (set 21) post heat-shock treatment (i.e., 70° C. for 10 minutes);

FIG. 2 is a graph depicting the MALS obtained from the biological indicator (BI) (approximately $1.7\times10^8$ *B. subtilis* spores dried on a glass slide) following autoclaving at 121° C./15 psi for five minutes followed by static culture incubation in BHI. The MALS data sets were obtained at the following time points after inoculation of the treated spores into culture: Set 6 (0 minutes), set 11 (30 minutes), set 16 (1 hour), set 21 (2 hours), set 26 (3 hours), set 31 (4 hours), and set 1 (24 hours);

FIG. 3 is a graph depicting the MALS measurements obtained from the biological indicator (BI) (approximately $1.79\times10^8$ *B. subtilis* spores dried on a glass slide) following autoclaving at 121° C./15 psi for three minutes. The MALS data sets were obtained at the following time points after inoculation of the treated spores into culture: Set 1 (overnight plus 6 hours), set 3 (0 minutes), and set 13 (1 hour);

FIG. 4 is a graph depicting the results of MALS measurements of *B. subtilis* treated by 3 minutes of autoclaving at selected culture intervals. The graph compares the measurements obtained from set 3 (0 minutes), set 8 (30 minutes), and set 13 (1 hour). Also, the measurements at all 15 angles are disclosed herein to illustrate the recorded MALS input data analyzed to generate the graphs;

FIG. 5 is a graph depicting the MALS measurements obtained using the biological indicator (BI) (*B. subtilis* spores dried on a glass slide) following ethylene oxide (EO) sterilization. The MALS data sets were obtained at six intervals during a four time hour period as follows: Set 9 (0 minutes), set 20 (30 minutes), set 30 (1 hour), set 35 (2 hours), set 40 (3 hours), and set 45 (4 hours). An untreated control sample examined at 0 minutes post-heat shock is shown as set 12;

FIG. 6 is a graph depicting the MALS measurements obtained using the biological indicator (BI) (*B. subtilis* spores) following STERRAD* ($H_2O_2$, hydrogen peroxide) sterilization. The MALS data sets were obtained at eight time points during a twenty-two hour incubation period in a 5% BHI as follows: Set 2 (0 minutes), set 6 (30 minutes), set 10 (1 hour), set 18 (2 hours), set 22 (3 hours), set 26 (4 hours), set 30 (4.75 hours), and set 1 (22 hours);

FIG. 7 is a graph depicting the MALS measurements obtained using the biological indicator (BI) (*B. subtilis* spores) following STERRAD* ($H_2O_2$, hydrogen peroxide) sterilization and comparing the measurements to measurements obtained using untreated control spores. The MALS data sets were obtained by examining samples taken at various time points for $H_2O_2$ sterilized spores incubated in BHI culture after heat shocking, and the data sets are as follows: Set 2 (0 minutes), set 6 (30 minutes), set 10 (1 hour), set 14 (2 hours), set 18 (3 hours), and set 22 (4 hours). Untreated (control) spores were examined at the following time points after heat-shock: set 1 (0 minutes control) and set 5 (30 minutes control);

FIG. 8A is an image depicting the MALS measurements obtained from the biological indicator (BI) (approximately $2.6\times10^6$ *B. subtilis* (Difco) spores dried in a glass vial) following autoclaving at 121° C. at 15 pounds per square inch for various time periods. The spores were examined using MALS directly after treatment. The MALS data sets were obtained at the following duration periods of autoclaving: Sets 13 and 14 (spores autoclaved for 2 minutes), and sets 22 and 23 (spores autoclaved for 15 minutes). Set 2 is a raw (native) untreated spore control and set 3 is a heat-shocked untreated spore control;

FIG. 8B is an image depicting the MALS measurements obtained from the biological indicator (BI) (approximately $2.0\times10^6$ *B. subtilis* WT168 spores dried in a glass vial) following autoclaving at 121° C. at 15 pounds per square inch for various time periods. The spores were examined using MALS directly after treatment. The MALS data sets were obtained at the following duration periods of autoclaving: Sets 15 and 16 (spores autoclaved for 2 minutes), and sets 26 and 27 (spores autoclaved for 15 minutes). Set 6 is a heat-shocked untreated spore control;

FIG. 8C is an image depicting the MALS measurements obtained from the biological indicator (BI) (approximately $2.0\times10^6$ *B. stearothermophilus* spores dried in a glass vial) following autoclaving at 121° C. at 15 pounds per square inch for various time periods. The spores were examined using MALS directly after treatment. The MALS data sets were obtained at the following duration periods of autoclaving: Sets 17 and 18 (spores autoclaved for 2 minutes), and sets 27 and 28 (spores autoclaved for 15 minutes). Set 8 is a heat-shocked untreated spore control;

FIG. 9A is a graph depicting the averaged log weighted intensity (Average Intensity) of *B. subtilis* (Difco) spores autoclaved for 2 or 15 minutes and incubated in culture for 0 to 4 hours post-treatment. More specifically, *B. subtilis*-Difco spores were untreated (♦) or autoclaved for 2 minutes (○) or 15 minutes (▲). MALS analysis was performed at 0, 2, and 4 hours after the spores were inoculated into growth media;

FIG. 9B is a graph depicting the averaged log weighted intensity (Average Intensity) of *B. subtilis* (168WT) spores autoclaved for 2 or 15 minutes and incubated in culture for 0 to 4 hours post-treatment. More specifically, *B. subtilis* 168WT spores were untreated (♦) or autoclaved for 2 minutes (○) or 15 minutes (▲). MALS analysis was performed at 0, 2, and 4 hours after the spores were inoculated into growth media;

FIG. 9C is a graph depicting the averaged log weighted intensity (Average Intensity) of *B. stearothermophilus* spores autoclaved for 2 or 15 minutes and incubated in culture for 0 to 4 hours post-treatment. More specifically, *B. stearothermophilus* spores were untreated (♦) or autoclaved for 2 minutes (○) or 15 minutes (▲). MALS analysis was performed at 0, 2, and 4 hours after the spores were inoculated into growth media;

FIG. 10 is an image depicting the MALS measurements obtained from heat-shocked, untreated *B. subtilis* Difco after various incubation periods. The following MALS data sets are depicted: Set 3 (spores which were heat-shocked and examined at 0 hours post heat-shock), sets 32 and 33 (spores examined 2 hours post heat-shock) and sets 60 and 61 (spores analyzed 3 hours post-heat-shock);

FIG. 11 is a graph depicting the MALS measurements obtained from the biological indicator (BI) (*B. subtilis* (Difco) spores dried in a glass vial) following autoclaving at 121° C./15 psi for 2 minutes. The MALS data sets were obtained at the following time points after inoculation of the treated spores into culture: Set 13 (0 hours), sets 41 and 42 (2 hours post-treatment) and sets 78 and 79 (4 hours post-treatment);

FIG. 12 is a graph depicting the MALS measurements obtained from the biological indicator (BI) (*B. subtilis* (Difco) spores dried in a glass vial) following autoclaving. The MALS data sets were obtained at the following time points after inoculation of the treated spores into culture: Set 22 (0 hours), sets 51 and 52 (2 hours post-treatment) and sets 97 and 98 (4 hours post-treatment);

FIG. 13 is a graph depicting the MALS measurements obtained from the biological indicator (BI) (*B. subtilis* (Difco) spores dried in a glass vial) following treatment with ozone at 0.3 ppm. The MALS data sets were obtained at 0 hours post-treatment where the treatment varied in duration as follows: Set 10 (control, untreated spores), set 39 (5 minutes of ozone), set 44 (10 minutes), set 49 (15 minutes), set 53 (20 minutes), and set 58 (30 minutes); and FIG. 14 is a graph depicting the MALS measurements obtained from the biological indicator (BI) (*B. stearothermophilus* spores dried in a glass vial) following treatment with ozone at 0.3 ppm. The MALS data sets were obtained at 0 hours post-treatment where the treatment varied in duration as follows: Set 18 (control, untreated spores), set 23 (5 minutes of ozone), set 28 (10 minutes), set 48 (15 minutes), and set 35 (20 minutes).

FIG. 16 is a printout of the data demonstrated graphically in FIG. 15;

DETAILED DESCRIPTION OF THE INVENTION

Figure 1:
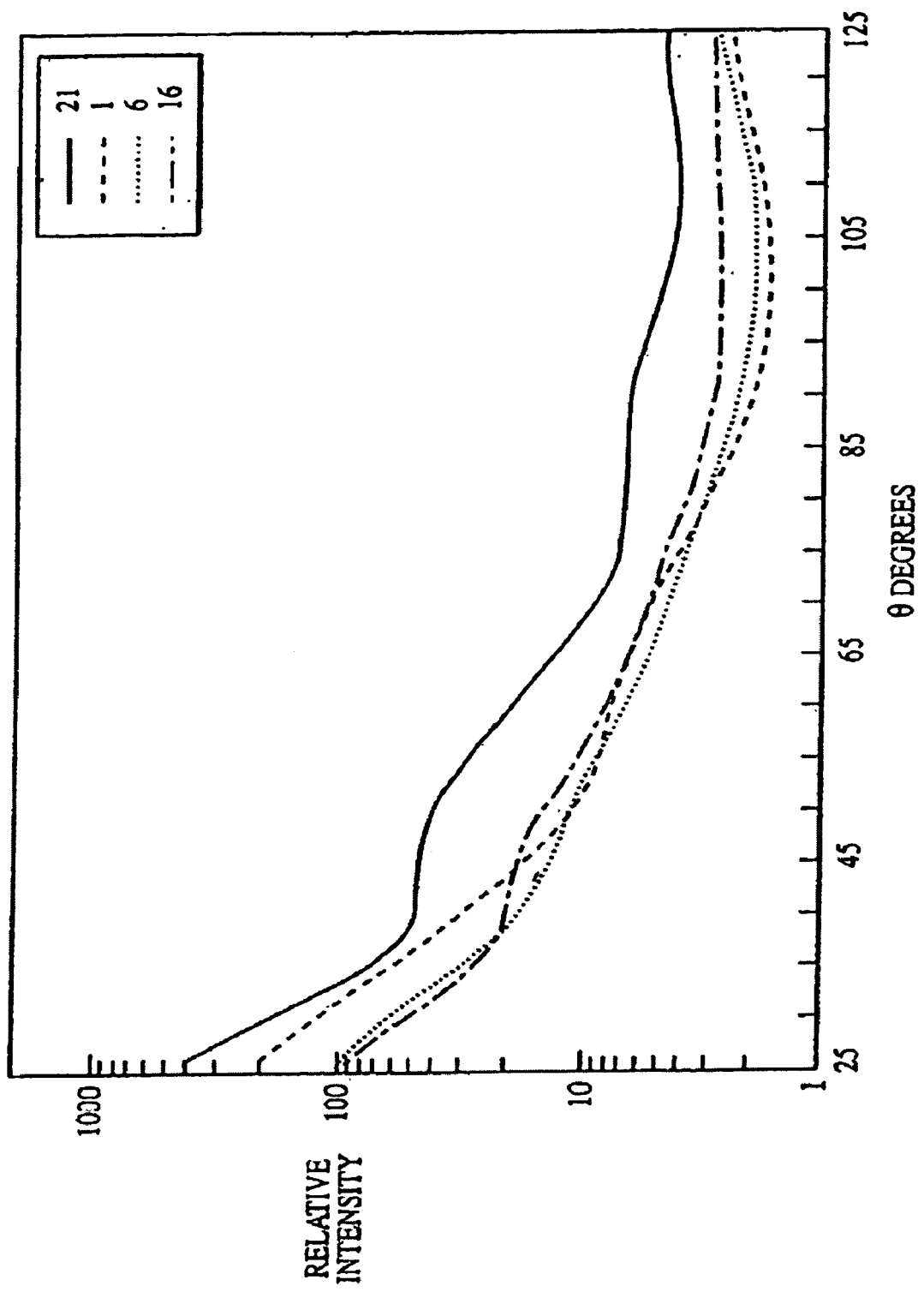

The invention is based on the discovery that *B. subtilis* spores undergo detectable changes as they germinate and grow and/or after various sterilization processes, they may undergo changes that can be measured, identified, and standardized using multi-angle light scattering (MALS). Applicants have further discovered that light scattering by a microorganism is affected by sterilization treatment and the effects of sterilization treatment on light scattering can be detected within minutes of the treatment using MALS. In addition, Applicants have discovered that the change in light scattering correlates to the viability of the microorganism.

Therefore, the present invention includes a system for detecting the effectiveness of a sterilization treatment. The system comprises a biological indicator, a solid support, a liquid medium, and a multiangle light scattering photometer, as these terms are defined and exemplified herein. The system is used as disclosed herein. Briefly, the biological indicator is exposed to a sterilization treatment and the biological indicator is then examined using MALS as disclosed elsewhere herein. The MALS data of the treated biological indicator can be compared to the MALS data of a standard or control profile obtained by examining an untreated like biological indicator using MALS.

Further, the present invention encompasses assays that assess the changes in a biological indicator comprising microorganisms using multiangle light scattering analysis to assess the efficacy of various sterilization methods soon after the sterilization procedure is performed with or without incubation of the microorganism in a growth medium (e.g., brain heart infusion broth, nutrient broth, trypticase soy broth, and the like). Accordingly, the present invention provides a rapid, sensitive and accurate biological indicator for determining the efficacy of sterilization treatments thereby obviating the need for complex culture methods requiring skilled technicians, extensive sample handling, and lengthy incubation periods.

The invention systems and methods detect the presence of viable microorganisms after the completion of a sterilization treatment wherein a source of microorganisms (i.e., a biological indicator, BI) is exposed or subjected to the sterilization treatment and its viability after the treatment is determined using an instrument, such as, preferably, a multiangle light scattering device that assesses changes in the microorganism.

A microorganism is "viable" if the microorganism can exhibit detectable growth (increase in number) and/or a change in morphology (e.g., the microorganism can germinate, change from spore to vegetative cell or rod, and the like) as detected by various methods including methods well-known in the art of microbiology (e.g., trypticase soy agar plate culture, acridine orange direct counts, detection of bacterial metabolites/enzymes, incubation in brain heart infusion broth, and the like) as well as novel methods disclosed elsewhere herein (e.g., multiangle light scattering).

"Incubation" includes contacting a microorganism with an appropriate growth medium under conditions in which the microorganism is expected to grow, i.e., germinate, outgrow and divide. Division can involve cell splitting or the formation of chains. The incubation can be either static or with agitation (e.g., shaking, rotation, rolling, and the like), and the incubation temperature depends upon the species of bacteria, e.g., *B. subtilis* is incubated at about 35-37° C. whereas *B. stearothermophilus* grows at about 55-60° C.

The sterilization method used as the sterilizing treatment of the invention can be any acceptable sterilization procedure, including, but not limited to, chemical sterilization methods such as, but not limited to, tetrasilver tetraoxide, ethylene oxide, hydrogen peroxide, and ozone, and physical sterilization treatments such as, but not limited to, dry heat, steam, gas plasma, and radiation, or any combination of physical and/or chemical methods known or to be developed.

As used herein unless otherwise specified, "sterilization" encompasses any sterilization or disinfection method available or to be developed.

In addition, the present invention should be construed to encompass the detection of the presence of viable microorganisms after a disinfection treatment wherein the effect(s) of a disinfectant, such as chlorine, alcohol, ozone, silver compounds, or other treatment is designed to kill microorganisms. Ozone can be used either as a sterilant or disinfectant. That is, if the process is intended to kill substantially all, and preferably all organisms present, then it is said to be sterilized. If, however, the number of organisms is reduced below that required to cause an infection, then it is said to be disinfected. For example, medical equipment gets sterilized, whereas drinking water or pool water gets disinfected. The method disclosed herein allows one to determine where the required level of disinfection has been achieved.

In one aspect of the invention, a biological indicator is used with a sterilizing process. The U.S. Pharmacopeia XXII, Official Monograph, 1990, pp. 1625-1626 (hereinafter USP XII, 1990), incorporated herein by reference, defines a biological indicator (BI) as a characterized preparation of specific microorganisms resistant to a particular sterilization process. It is used to assist in the qualification of the physical operation of sterilization apparatus in the development and establishment of a validated sterilization process for a particular article, and the sterilization of equipment, materials, and packaging components for aseptic processing. It may also be used to monitor a sterilization cycle, once established, and periodically in the program to revalidate previously established and documented sterilization cycles. BIs typically incorporate a viable culture of a known species of microorganism.

A biological indicator is an organism and more particularly, an organism in a specific form that is most resistant to a sterilization or disinfection process, and which can be used to assess the efficacy (effectiveness) of the particular process. That is, for instance, the biological indicator allows assessment of whether a disinfectant has made water safe to drink and/or whether autoclaving has killed all of the microorganisms present, but is not limited to these uses.

The types of microorganisms, preferably bacteria, used as the biological indicator of the invention to determine the sufficiency of the sterilization treatment include *Bacillus* and *Clostridia* species, such as *B. subtilis, B. stearothermophilus, B. pumilus, Clostridium sporogenes*, and the like. See, e.g., USP XII, 1990. Preferably, the microorganisms are bacteria of the *Bacillus* family, and more preferably, the source of the bacteria is in the form of a spore, since that form is the stage in the bacterial life cycle most resistant to sterilization methods. Even more preferably, the microorganism is a *B. subtilis* spore. However, the invention should be construed to include the examination of the lethality of sterilants or disinfectants against waterborne bacteria such as *Escherichia coli, Legionella* sp., *Campylobacter* sp., and other enteric bacteria, as well as *Staphylococcus* and *Streptococcus* species and other human pathogenic microorganisms such as *Cryptosporidium*, to assess the efficacy of a sterilization and/or disinfection treatment. In addition, more than one type of microorganism can be used as a BI in this invention.

The preferred test strains for use as biological indicators are those that are the most resistant to the processes used for sterilization. The most resistant organisms are those which form endospores, i.e., bacterial spores. Organisms such as *Bacillus subtilis, Bacillus stearothermophilus, Bacillus coagulans*, and *Clostridium sporogenes* have been used for demonstrating the efficacy of moist heat sterilization (autoclaving). The biological indicator must provide a challenge to the sterilization process that exceeds the challenge of the natural microbial burden in or on the product (Agalloco et al., 1998, PDA J. Pharmaceutical Sci. & Tech. 52:346-350).

It will be understood by one skilled in the art, based on this disclosure, that the biological indicator encompasses any microorganism whose resistance to a sterilization treatment exceeds that of the other microorganisms that must be destroyed by the treatment. Further, it will be understood based upon this disclosure that the type of microorganism(s) used as a biological indicator is dependent upon a variety of factors including, but not limited to, the type of sterilization treatment being assessed. For instance, the $D_{121}$ value (the $D_{value}$ is the time required to reduce the number of bacteria (e.g., spores) by 1 log (i.e., 90%)) for *B. subtilis* at 8% humidified ozone sterilization is 5 minutes, but it is 4.3 minutes for *B. stearothermophilus*. Since *B. subtilis* is also used for ethylene oxide, e.g., BI-OK™ (Propper Manufacturing Co., Inc.), and hydrogen peroxide sterilization treatments (e.g., *B. subtilis* is used by Johnson & Johnson in its detectors for use with the STERRAD* hydrogen peroxide sterilizer), it appears to be the choice organism for cold sterilization treatments.

Microorganisms comprising a biological indicator can be placed on a non-porous or porous support such as an adsorbent filter, membrane, matrix, or other solid support made of any suitable inert material. The solid support should not dissolve the reactants or components. Thus, the solid support on which spores are inoculated is simply a vehicle by which a selected number of indicator organisms are held and positioned within the BI.

Solid supports can vary widely in the choice of materials and shapes so long as this function is served. Carriers may be formed of materials such as filter paper, which has excellent storage stability but which has drawbacks in that it cannot be used in STERRAD* sterilization and which may hinder the full retrieval of all organisms following treatment. For example, in some instances, the porosity of filter paper does not allow reproducible and consistent exposure of the spores to the sterilant. Solid supports may also be made of metals such as aluminum or stainless steel, glass, ceramics, plastics, membranes, and combinations thereof.

Solid supports can be inoculated with spores by preparing an aqueous solution comprising spores at a desired spore concentration ranging from about $2 \times 10^6$ to about $2 \times 10^8$ spores per milliliter. An aliquot of the spore mixture is placed onto a solid support. Such operations can be performed according to the USP XII, 1990, Bacteriostasis Test Method. Briefly, a suspension or dispersion of *B. subtilis* spores in water is prepared to yield a desired number of spores per aliquot for inoculating a solid support such as filter paper or, more preferably, a glass slide or glass vial.

The spores are allowed to dry onto the support. Although an air flow can be used to dry the spores onto the support, such as, but not limited to, by placing the support in a laminar flow-hood, to hasten the drying process, this is not required to practice the invention. One skilled in the art will understand based on this disclosure, that the method of drying the spores onto the support includes, inter alia, simply allowing the spores to air dry by leaving them stand, placing the spores in a dessicator containing a desiccant such as, but not limited to, calcium chloride, placing the spores in a laminar-flow hood, and the like. One skilled in the art would understand based upon this disclosure, that heat is preferably not used to dry the spores on a support since, without wishing to be bound by any particular theory, heat drying may be equivalent to heat-shocking, which would likely decrease the spore's resistance to treatment, at least to heat-based sterilization treatments (e.g., dry heat and steam). However, the invention should not be considered limited to drying without heat.

In one embodiment, a commercially available spore suspension comprising about $1.7 \times 10^8$ spores per milliliter was placed on a Teflon-coated slide and was then air dried. In another embodiment, the spore suspension was placed in a polypropylene tube and the sample was then air dried. Further, in another embodiment, the spores were added to a glass scintillation vial and the sample was dried in a laminar flow-hood. However, the present invention should not be construed to be limited to these, or any, particular method of adsorbing the spores onto a solid support. Instead, any method whereby the spores are dried onto a solid support while preserving their viability may be used in the present invention.

In principle and in operation, the biological indicator is subjected to the same sterilization or disinfection treatment as the utensils and/or other items for which sterile conditions are sought. The heat is applied and/or the gas, steam, or chemical and/or physical agent passes into the compartment where the spores are located thereby exposing the spores to or treating the spores with the same sterilization or disinfection process or agent as any of the utensils or other materials.

Following the sterilization or disinfection treatment, a nutrient source is brought into contact with the spores. In one embodiment, the spores are removed from the solid support and inoculated into a liquid culture. Dried spores in a scintillation vial have nutrient liquid added and the spores are suspended. However, the invention should not be construed to be limited to removing the spores from the solid support and transferring them to liquid culture. Instead, the invention is intended to include any procedure whereby the spores are brought into contact with a liquid or solid growth medium under conditions which allow their growth or to include embodiments in which a growth medium is optional. For instance, the invention encompasses the spores being placed in chamber within a closed container wherein the liquid growth medium is separated from the spores within an ampoule or other separate compartment, such as the device described in U.S. Pat. No. 5,167,923, for example. After treatment, the growth medium is brought into contact with the spores by breaking the ampoule without the need to open the chamber containing the spores.

Alternatively, the growth medium may be present in the container in powder or tablet form and, after sterilization treatment, sterile water may be added to the container such that the spores come into contact with the aqueous growth medium using methods which are well-known in the art to maintain the spore and dry growth medium from contacting prior to or during the sterilization treatment (e.g., about $10^8$ spores and dry BHI powder in an amount to give 5% BHI broth when about 1-2 milliliters of water are added).

The invention encompasses a system and/or method of examining a biological indicator using, for example, a multiangle light scattering assay, directly after sterilization treatment or shortly thereafter, e.g., within about one minute to about 4 hours after the treatment. That is, any change in the biological indicator compared with an otherwise identical untreated BI, can be assessed without need for standard bacterial culture methods (e.g., trypticase soy agar plating, growth in BHI for at least about 24 hours to 7 days) as required by prior art BIs (e.g., 3M Attest™, Propper BI-OK™, SURGICOT™, and STERIS®, and the like). Thus, one skilled in the art would understand, based upon the disclosure provided herein, that the biological indicator can be contacted with a growth medium and either analyzed directly using MALS or allowed to incubate with the growth medium until analyzed using MALS at a later time (preferably, from about 0 to about 4 hours after the sterilization or disinfection treatment).

One skilled in the art would appreciate, based upon the disclosure provided herein, that the container acting as the support and containing spores and/or an additional support should allow the sterilant to contact the spores but prevent the spores from contaminating the contents of the sterilization chamber. Moreover, the container should allow the sterilant or disinfectant to contact the spores without allowing the spores to be released into the sterilizer chamber. Preferably, for containers comprising a separate chamber comprising a liquid or solid growth medium, the chamber comprising such growth medium is preferably impermeable to the sterilant or disinfectant and separate from the spores, such that the two are not contacted until sufficient force is applied to break the barrier separating the spores from the growth medium. A plethora of such containers, and others not comprising growth medium, have been described previously and are well-known in the art.

Preferably, the spores are air dried onto Teflon-coated slides as described elsewhere herein. More preferably, the spores are air dried in a cuvette or glass scintillation vial. The spores are then subjected to sterilization or disinfection treatment. The spores are then contacted with a liquid medium including, but not limited to, water, or growth media comprising nutrients. The spores can then be examined using MALS either directly after addition of the liquid medium, or sometime thereafter. That is, the cuvette or vial can be placed directly into a MALS instrument (e.g., DAWN-B) and the spores can be examined without the need to transfer the spores from the cuvette or vial. Alternatively, the liquid medium comprising the spores can be passed through the MALS instrument (e.g., DAWN-F) to examine the spores. The spores may also be examined immediately after sterilization treatment with or without the use of a growth medium by subjecting the spores directly to a MALS instrument such as an Ocean Optics USB-200, commercially available from Ocean Optics, Inc. in Dunedin, Fla. Typically, the spores are examined using MALS from about 0 to about 4 hours after contacting the spores with the liquid medium. More preferably, the spores are examined from about 0 to about 2 hours after contacting the spores with the liquid medium. Even more preferably, the spores are examined from about 0 to about 1 hour after contacting the spores with the liquid medium. Most preferably, for spores treated using steam, and ozone, the spores are examined directly after contacting the spores with the liquid medium.

In another aspect, a suspension or dispersion of spores is air dried, preferably to coat the interior of a plastic or glass container (e.g., a cuvette, a scintillation vial, and the like), and a dry form of the growth medium can be placed in the container. The dry growth medium can be kept separate from the spores as described previously elsewhere herein using methods well-known in the art. Following sterilization or disinfection, sterile water can be added and the spores brought into contact with now aqueous growth medium formed by adding water.

Preferably, the spores are dried on a slide or in a container and, following sterilization or disinfection treatment, the spores are contacted with a liquid medium including, but not limited to, water, a growth medium comprising nutrients, and the like. It would be understood by one skilled in the art, based on this disclosure, that the liquid medium used depends on the type of spore being examined and that a growth medium is optional. A wide variety of growth media for use with various spore types is well known in the art and the selection of the appropriate growth medium for the spore used is well within the knowledge of one skilled in the art.

Where spores on a slide are used, the spores are removed from the slide after sterilization or disinfection treatment using a liquid medium. The spores can then be transferred to a container and contacted with a growth medium and examined using MALS as described previously elsewhere herein. That is, the spores can be placed in a container which is then placed in the MALS instrument and examined, or the spores can be passed through a MALS instrument such as the Model F which does not require that the sample be placed in a container within the instrument. Thus, it would be understood by one skilled in the art based on this disclosure, that the invention includes incubating the spores in a container which can be placed in a MALS instrument, grown in one container and then transferred to a container that can be placed in a MALS instrument, or grown in a container and then removed from the container and examined using a MALS instrument that does not require a container to be placed within it. Such MALS instruments are described elsewhere herein and/or are well known in the art.

As an alternative to the slide or other support, a tube can be used which is formed of borosilicate in the shape of a vial or a glass, or plastic cuvette suitable for use in a preferred multiangle light scattering instrument such as, for example, the DAWN Model B and/or the DAWN Model F photometer. Thus, using the same closed-tube in an assay system, the spores can be exposed to a sterilization treatment, contacted with a liquid growth medium, and cultured such that the entire sample, without further sample handling, can be examined directly using MALS thereby minimizing sample handling and decreasing the possibility of bacterial contamination and/or sample loss. In addition, such a procedure and system decrease the costs and delays associated with prior art biological indicators used to determine the efficacy of the treatment.

After the spores are inoculated into the liquid culture, a heat shock step is desirably, but not necessarily, performed. Heat shock is a sublethal thermal treatment given to liquid spore suspensions to activate enzymes in preparation for germination. Thus, a preferred sequence is a heat-shock step, cooling, diluting the spore suspension, and then incubating the spores. A preferred heat-shock procedure in a vial comprises heating the spores at 70° C. for 10 minutes to induce germination. The spores are suspended in 5% BHI broth, placed in a heating block for 10 minutes at 70° C., and cooled to about 37° C. by refrigerating at 4° C. for about 5 minutes. However, the invention encompasses other heat-shock procedures that are well known in the art, and the precise parameters depend on the identity of the organism whose spores are being heat shocked as would be understood by one skilled in the art based upon this disclosure. These heat-shock parameters include heating at a temperature ranging from about 60° C. to about 80° C. for from about 8 minutes to about 12 minutes, followed by cooling from about 5 to 15 minutes. Alternatively, where heat-based or ozone treatments are involved, the heat-shock step followed by cooling and diluting the spores, can be omitted. Further, there may be other sterilants that affect the spores such that heat-shocking is unnecessary. Further, one skilled in the art would understand, based upon this disclosure, that the control, untreated standard sample is heat-shocked such that the spores will germinate in a short period of time allowing assessment of the efficacy of treatment, generally, within about 0 to 4 hours.

Any growth medium, liquid or solid, that will support the growth of the spores can be used in the present invention when a growth medium is desired and the invention is therefore not limited to any particular growth medium. A preferred growth medium includes, but is not limited to, brain heart infusion (BHI) broth for growth of B. subtilis bacteria.

Following sterilization treatment and heat-shock and/or incubation of the spores in growth medium, the spores are examined using MALS. In one embodiment, the DAWN Model B photometer was used to derive data sets for each sample at various time points. In another embodiment, a Model F photometer was used for MALS analysis. However, the present invention should not be construed to be limited to this or any other particular photometer, nephelometer, or other light scattering instrument. Rather, any light scattering instrument capable of distinguishing the various spore forms on the basis of their light scattering profile can be used to assess the viability of the biological indicators.

The MALS photometer (Wyatt, 1968, Appl. Optics 7:1879; Wyatt et al., 1976, In: Analysis of Foods and Beverages, Modern Techniques, p. 225, Charalambous, ed., Academic Press, NY) uses a MW linear polarized He—Ne laser as the light source as described in Felkner et al. (1989, Sci. Technol. Lett. 1:79-92) and Anderson et al. (1993, J. A.O.A.C. Int. 76:682-689). Briefly, the laser provides high power density at the point where the sample is irradiated and thus illuminates the sample by means of a narrow beam diameter (the $1/e^2$ diameter of the Gaussian beam profile is 0.39 mm). Very small particles or molecules, whose refractive indices are close to the refractive index of the suspending medium, scatter light according to the Rayleigh-Debye-Gans (RDG) theory, i.e., as a function of sin $(\theta/2)$.

The laser incident beam passes through a suspension of particles, e.g., bacterial cells, resulting in the light being scattered (e.g., Anderson et al., 1993, J. A.O.A.C. Int. 76:682-689). The scattered light is collected simultaneously by 15-18 transimpedance photodiodes (detectors) which are located with respect to the incident laser beam at discrete angles incrementally displaced in units of sin $(\theta/2)$. The diffraction scattering patterns of particles, such as bacteria, can satisfy the RDG theory and have nearly equidistant spacings of the scattering pattern peaks and valleys when plotted against sin $(\theta/2)$. The laser beam system thus generates unique profiles of particles in the bacterial size range (1-3 mm) by measuring the intensities at the various angles and plotting the relative intensity against the scattering angle. The resulting data are displayed graphically as the log (relative intensity) against scattering angle. The height of the overall intensity profile along the y axis correlates to the number of particles and/or microorganisms in a suspension, and the curve displacement between smaller and larger scattering angles along the x axis correlates to the size and distribution and distribution of particles, respectively. This profile is the differential light scattering (DLS) profile for the particles in solution.

When a reading is taken on a sample, the array of 15 detectors simultaneously collects the scattered light and the intensity at each detector can be plotted graphically versus the scattering angle in degrees. These readings are collectively referred to as a "set" which can be displayed as a computer generated curve. Thus a set reading is taken on a sample at time 0 and at one or more subsequent times. The curves for two samples (each with two sets) are stored in a computer. The computer stores the data from each set under a unique number and the set numbers will be displayed when the data are shown either in graphic or tabular form.

The averaged log weighted intensities of a set (i.e., averaged from all 15 detectors) correlate directly to the number of particles so that the number of bacteria at time 0 ($N_o$) and the number of bacteria at a subsequent time (N) can be calculated using algorithms in a commercial software program (Wyatt Technology Corp., Santa Barbara, Calif. and Technical Assessment Systems, Inc., Washington, D.C.). Thus, $N/N_o$ can be used to show changes in the number of particles over time and to calculate the generation time, i.e., time elapsed between set readings by $ln_x$ of $N/N_o$, which is equal to the logarithmic doubling time of a bacterial culture (TAU).

As demonstrated herein, the MALS system easily differentiates between cellular shapes and resolved cell size/shape differences of approximately 5% in accordance with Wyatt (1968, supra). Response to sterilization treatments is detected through decreased normal cell numbers and/or cell shape changes compared to control (untreated) cell suspensions. These changes are detected immediately (2-6 minutes) in the case of autoclaved spores and ozonated spores, or the shape changes are expressed during cell germination as seen in the spores sterilized using ethylene oxide and hydrogen peroxide elsewhere herein. Without wishing to be bound by theory, EO treated spores exhibit an altered germinating body morphology but cell division likely does not occur, indicating inactivation of the spores. Thus, the altered morphology and/or its timing would be dependent upon the nature of the sterilization treatment. Comparison of data from the exposed and unexposed cell populations using a variety of sterilization conditions herein allowed the detection and quantitative analysis of specific responses to sterilization. With respect to $N/N_o$ values, control variations are expected to be 10% or less, and TAU values generated from $N/N_o$ are significant when they are ≧10% different from the control.

In one embodiment using a DAWN Model B multiangle light scattering photometer, the instrument comprised fifteen photodiodes. However, applicants have determined that fifteen photodiodes are not required for detection of spore viability, growth, change in number and/or morphology. Instead, at least about 5 detectors arranged from about 23 to about 120 degrees $\theta$ (where $\theta$ (theta) is the angle(s) at which the diodes are place to detect light scattering of the particles in solution), or as many as a maximum of about 18 detectors can be used to detect the viability or change in number and/or morphology of the microorganisms following sterilization or disinfection treatment. Most preferably, 5 or 6 detectors are used.

Accordingly, although the examples provided herein disclose using the DAWN Model B or F photometer for MALS, a number of variations of the light scattering photometer instrument are encompassed in the invention. The various principles involved in the use of MALS for the examination of various particles are described in, e.g., U.S. Pat. Nos. 4,907,884; 4,710,025; 4,693,602; 4,616,927; 4,548,500; 4,541,719; 4,173,415; 4,101,383; 3,815,000; 3,770,351; 3,730,842, which are incorporated by reference herein. Therefore, any light scattering instrument can be used which can distinguish among the various forms of sporulating bacteria. The preferred number of photoreceptors and/or angles at which they can be arranged ranges from at least 4 to about 18 photoreceptors at angles ranging from about 20° to about 160°.

A biological indicator is also provided which provides immediate determination after sterilization of whether the test microorganisms of the biological indicator (e.g., *Bacillus subtilis* spores) were killed. Autoclaved spores have been assessed for viability by a spectrophotometric procedure using MALS instrumentation available from Ocean Optics Model USB-2000. It is expected that the same result may be achieved using any other similar instrumentation. Further, without wishing to be bound by theory it is expected that such spores subjected to ethylene oxide or a hydrogen peroxide plasma (i.e., as in a STERRAD® sterilization system) can also be successfully monitored for the effectiveness of the sterilization using the Ocean Optics Model USB-2000 or a similar instrumentation. When normal spores are compared with autoclaved spores using the Ocean Optics Model USB-2000 or any similar instrumentation, they are markedly different in their appearance when viewed by electron microscopy, and their spectroscopic properties are likewise quite different. Both simulations and actual experiments using such instrumentation showed that it can be immediately determined whether spores have been killed by autoclaving. Spectroscopic simulations based on electron microscopy gave a strong indication that the Ocean Optics Model USB-2000 or a similar instrument can readily determine whether ethylene oxide or hydrogen peroxide-sterilized spores have been killed. Furthermore, the results should be quantitative, i.e., it can be determined from the data what the number of damaged and/or killed spores is relative to the number of normal/viable spores.

The light scattering profiles of untreated spores (i.e., "like" spores which are otherwise identical to treated spores except they have not been subjected to sterilization or disinfection treatment), prior to or in the absence of incubation or after incubation in growth media, are measured at various time points and can be used to generate a standard profile or control for each time point (which encompasses various stages of germination). Such standard profiles can be compared with the corresponding profile of treated spores which have been processed in the same manner, using the data analysis software provided with the light scattering photometer unit.

Alternatively, a control untreated sample can be run in parallel and contemporaneously with the treated spore sample being queried such that the light scattering profiles of the untreated versus the treated spores at one or more time points can be compared. Also, light scattering profiles of treated spores at different time intervals may be undertaken and compared over time such that, for example, a lack of detectable change in the profiles over time would indicate that no change in morphology and/or growth has occurred thereby indicating that the spores are not viable after sterilization treatment.

In sum, the invention includes the comparison of profiles of a treated sample compared to a standard profile derived previously as well as comparison of the profiles of a treated and an untreated (control) sample where the control sample is run in parallel with the treated sample, and the comparison of a profile of a treated sample with the profile obtained from the same sample at a later time point of incubation, or any permutation or combination of these profiles.

Preferably, the profiles of treated and the reference profile (e.g., a standard profile run previously using untreated spores or a control profile obtained using untreated spores processed in parallel with the sample being assayed), may be compared at 0 minutes after sterilization or disinfection treatment of the spores with or without heat-shocking (i.e., the spores are examined "directly" after treatment). More preferably, the profiles are compared at or about 30 minutes after treatment, even more preferably at or about 1 hour after treatment, yet even more preferably at 2 hours, and even more preferably after 3 hours, yet more preferably after 4 hours, and most preferably after 24 hours of incubation following sterilization or disinfection treatment.

Without wishing to be bound by any particular theory, the change in the light scattering profile of a sterilization treated spore, as detected using MALS, can be due to altered morphology caused by the treatment and/or by lack of germination or altered germination due to the treatment, and/or by decreased number of normal particles being detected by the MALS instrument due to degradation of the spores caused by sterilization or disinfection and/or by shrinkage of the spores beyond the detection limits of the instrument all due to the sterilization or disinfection treatment. One skilled in the art would understand, based upon the disclosure provided herein, that the precise mechanism whereby the MALS profile of a microorganism is affected by sterilization treatment is not crucial to the present invention. The important feature of the invention is that sterilization and disinfection affect the light scattering profile of a microorganism as detected using multi-angle light scattering analysis even if the mechanism is different for different sterilants or is not fully understood.

The invention includes various kits which comprise a biological indicator, such as a spore of various bacteria and/or *Cryptosporidium*, where a known number of the spores, preferably about $2 \times 10^8$ cells, are adsorbed onto a solid support. The kit further comprises a multiangle light scattering photometer for examining the light scattering of both untreated control spores and spores which have been subjected to a sterilization or disinfection treatment, and instructional materials which describe use of the kit to perform the methods of the invention. Although exemplary kits are described below, the contents of other useful kits will be apparent to the skilled artisan in light of the present disclosure. Each of these kits is included within the invention.

In one aspect, the invention includes a kit for assessing the viability of a bacterial spore after a sterilization treatment. The kit is used pursuant to the methods disclosed in the invention. Briefly, the kit may be used to assess the viability of a hot (e.g., dry heat or saturated heat) or cold (e.g., gas plasma, ethylene oxide, hydrogen peroxide, ozone, and the like) sterilization treatment.

The kit includes a multiangle light scattering photometer. The MALS photometer is used per the instruction provided with the device and is used to detect any growth, change in number of organisms, or change in morphology of the organism following the sterilization treatment.

Moreover, the kit preferably comprises an instructional material for the use of the kit. These instructions simply embody the examples provided herein.

The invention also includes a kit for assessing the viability of a bacterial spore after a disinfection treatment. The kit is used pursuant to the methods disclosed in the invention. Briefly, the kit may be used to assess the viability of a hot (e.g., dry heat or saturated heat) or cold (e.g., gas plasma, ethylene oxide, hydrogen peroxide, ozone, and the like) disinfection treatment.

The kit includes a multiangle light scattering photometer. The MALS photometer is used per the instruction provided with the device and is used to detect any growth, change in number of organisms, or change in morphology of the organism following the disinfection treatment.

Moreover, the kit preferably comprises an instructional material for the use of the kit. These instructions simply embody the examples provided herein.

The invention is further described in detail by reference to the following, non-limiting examples. Thus, the invention should be construed to encompass any and all variations which become evident as a result of the teaching provided herein.

EXAMPLE 1

Determining the efficacy of sterilization using a biological indicator (BI):

The experiments presented in this example are summarized as follows. The data presented herein disclose a novel biological indicator (BI) system for monitoring the efficacy of "hot" or "cold" (i.e., non-heat, e.g., chemical, radiation) sterilization. The BI system consists of a known quantity of purified and standardized *Bacillus subtilis* spores that were dried onto a glass slide, which were then placed into a container (i.e., a glass petri dish for steam treatment and plastic petri dish for cold sterilization), and subjected to a sterilization treatment. The viability of the spores was then rapidly determined using a multiangle light scattering (MALS) device (DAWN Model B, or a Model F, Photometer, Wyatt Technology Corp., Santa Barbara, Calif.) that monitored the spore response to the sterilization treatment. The spores were examined using MALS as follows.

The sterilized (treated) and the control (untreated) spores were separately eluted from the slide and were placed into a cuvette or a borosilicate glass scintillation vial containing 5% Brain Heart Infusion (BHI) broth. The untreated, control spores or the hydrogen peroxide and ethylene oxide treated spores were then heat-shocked at 70° C. for 10 minutes to induce germination. After cooling to ambient temperature, the heat shocked spore suspension was examined using MALS at the 0 minute start time, and the samples were then incubated at 37° C. in BHI for various time intervals. MALS measurements were taken at intervals of 30 minutes, two hours, and four hours to document the discrete stages of spore germination and formation of viable vegetative cells. When a sterilized Biological Indicator (BI) was being assessed, an additional measurement was made at 24 hours post-treatment to ensure that any growth present, even though slow, was detected. The germination stages were detected by comparison of the samples to unique profiles generated from MALS analysis, which profiles were computer generated and/or analyzed.

Graphic display and data scoring were performed using computer programs specifically developed for analyzing MALS data per the manufacturer's instructions. The data processing and storage programs allow the comparison of any profile derived in the past, present, or future, or any combination thereof.

The results of the computerized MALS data were verified by several standard techniques for the detection and identification of various *B. subtilis* growth stages and/or forms, including use of acridine orange direct counting (AODC) of spores and/or vegetative bacilli (Sharma and Prasad, 1992, Biotech. Histochem. 67:27-29; Bruno and Mayo, 1995, Biotech. Histochem. 70: 175-184) and by plating control or treated spore samples onto trypticase soy agar (TSA) plates to detect and enumerate viable spores. Also, TSA broth was inoculated and incubated to ensure that growth or lack of growth occurred. The AODC staining procedure, when visualized by ultraviolet microscopy, is capable of differentiating between the various successive stages of spore germination. Included in these successive stages (in order of their appearance) are green-staining spores, round or oblong red-orange bodies, well defined red-orange single rod-shaped bacilli, and large red-orange bacilli that are dividing within four hours. Each AODC stage corresponded to the unique profiles generated by the MALS monitoring system. The unique profile can be seen in a graphic display where the relative light intensity (y axis) is plotted versus the angle θ of each photo detector (x axis).

Data disclosed herein were generated by steam autoclave, ethylene oxide, ozone, and hydrogen peroxide sterilization and demonstrate that spore survival/killing can be determined within about two hours after sterilization treatment by using the B. subtilis biological indicator (BI) monitored by a MALS instrument (e.g., DAWN-B and DAWN-F). Moreover, the data disclosed herein demonstrate that by as soon as 30 minutes and even directly following treatment, detectable morphological changes have occurred that are determinative for demonstrating successful sterilization. Both successful and failed sterilization conditions were readily determined using this system, and the sensitivity of this detection method is at least equivalent to, and in most cases more sensitive than, routinely used prior art biological indicators and methods.

The Materials and Methods used in the experiments presented in this example are now described.

Preparation of the Biological Indicator

A clean spore suspension of a well-known bacterial spore-forming strain was obtained from a reliable commercial source. The prior art teaches the use of bacterial spores from species such as B. subtilis and B. stearothermophilus as biological indicators of sterilization with either steam or chemical sterilizers. In this example, B. subtilis spores were obtained from Difco Laboratories (Detroit, Mich.), because they are cleaned and washed to purify and standardize the spores prior to use. The spores were stabilized and standardized at approximately 1.6 to $1.8 \times 10^8$ spores/ml.

Spore Preparation

The surface of a Roux bottle containing about 300 ml of A K agar #2 (Becton-Dickinson Microbiology Systems, Cockeysville, Md.) was seeded with B. subtilis, ATCC 6633, and the spores were incubated for five days at 37° C. The growth was scraped off and was suspended in about 50 ml 0.1 M Tris chloride (pH 8.0). The spore suspension was then treated with 0.1 mg/ml lysozyme at 37° C., followed by further treatment with 1% sodium dodecyl sulfate for 30 minutes at room temperature to clean the spores. The suspension was centrifuged at low speed to remove any debris and less dense spores, and after decanting, the spores were washed 10 times in deionized and distilled water. The spores were resuspended in distilled water at an optical density ($OD_{625nm}$) of 0.3, which gave a concentration of about $1.7 \times 10^8$ spores/ml. This suspension can be more accurately standardized using a MALS DAWN-B or DAWN-F instrument (Wyatt Technology Corp., Santa Barbara, Calif.). AODC slides were used to verify the actual concentration of spores as well as the appropriate morphology of the spores.

BI Slide Preparation

Using a B. subtilis spore suspension from Difco (estimated concentration of $1.7 \times 10^8$ spores/ml/vial) the entire contents (1 ml) were added to a Teflon-coated slide with 8 wells, and the suspension was air dried in a laminar-flow hood under sterile conditions for a minimum of 1 hour. A longer drying period was used, but did not improve the dryness or stability of the BI on the slide. This slide was placed in a Petri dish and used for a sterilization challenge.

Alternate Form of BI for Sterilization Challenge

The bottom of a polypropylene tube was coated with B. subtilis spores at a concentration of $1.7 \times 10^8$ and the sample was air-dried under sterile conditions. A capsule (or pill form) containing dry, sterile, BHI in an amount sufficient to give a 5% concentration when added to 10 ml of sterile distilled water, was attached to the cap (within a small sealed crushable vial) within the polyethylene tube. After sterilization, the small vial containing BHI was crushed and sterile distilled water ($dH_2O$) was injected into the polypropylene tube using a syringe. The contents, having spores, BHI, and water were mixed thoroughly, and the sample was then heat-shocked, if required, at 70° C. for 10 minutes. The sample was allowed to cool to 37° C., and the sample was then introduced into a cuvette/scintillation vial and read immediately and later by the MALS device or introduced through a flow-through device.

MALS Data Collection and Processing of the B. subtilis BI

The instrument used to collect and analyze data on performance of the biological indicator was a Wyatt Technology DAWN Model B or Model F light scattering photometer (DAWN-B and DAWN-F) designed and manufactured by Wyatt Technology Corporation (Wyatt, Santa Barbara, Calif.). The DAWN instruments included a vertically polarized 632.8 nm helium neon (HeNe) laser light source, a "read-head" with 15 photodiode detectors (i.e., 15 angular measurement detectors that range from 23.07 to 128.32 degrees) and a laser monitor at 180 degrees, and an amplifier board that provides analog signals of the output. The amplifier booster PC board permits gain settings of 1×, 20×, and 100× with the capability of being adjusted to modify the strength or intensity of the signals.

The DAWN-B photometer is a batch measurement system so that each measurement is made from a particle suspension within a single borosilicate glass scintillation vial (commercially available through Fisher Scientific, Co.). The measurements were made in a horizontal plane tilted at 5° about the circumference of the "read head" and can be tailored to specific needs with the potential of setting the read-time intervals. For all measurements in the data disclosed herein, there were 400 measurements/second for 4 seconds, of which the most representative 10% of these were sampled for calculation purposes. The DAWN-B was calibrated and normalized each day prior to making measurements per the manufacturer's instructions.

The software used to analyze the data presented herein was developed and copyrighted by Wyatt. The software used to collect data included a program designated as "SPORE" with subfiles including DAWN-B87 subfile used to collect data and SKOR-B87 subfile to analyze the results obtained on bacterial culture populations. The data obtained from the instrument typically in print out form included results for various parameters including information from each detector and its angle, the intensity of light scatter at each angle and their log weighted average intensity, standard deviation, gain, number of values kept, solvent-adjusted wavelength, refractive index of solvent, and laser wavelength. The data collected by the device were then inputted into unique, retrievable readable data files which were indexed according to the date of the sample analysis such that each sample was assigned a unique set number within each file by the computing device.

The data display described above was sufficiently thorough to permit the determination of which detector angles were the most critical to the identification of the B. subtilis spore, germinative cell, and vegetative cell morphologies as well as any additional discernible subpopulations that might arise under normal germination and/or which arose as a consequence of the sterilization treatments used to challenge the BI. It was determined that using the spore preparations as described above, the addition of 900 μl from the 20 ml eluant into 15 ml of 5% BHI yielded highly reproducible values from either heat-shocked or non-heat shocked *B. subtilis* spore cultures. Higher concentrations of spores resulted in saturation values (values that plot off-scale for a two log scale plot) for one or more of the detectors.

Acridine Orange Staining for Assessment of Spore Germination Morphological Forms and Assessment of Total Numbers Acridine orange (AO) staining was used to provide a method for image analysis by color fluorescence of the various morphologies appearing during germination. AO staining is based on interaction of the dye with nucleic acid (RNA or DNA) to form a red-orange color when viewed by ultraviolet microscopy. The spore cortex prevents dye penetration and contact with nucleic acid, hence causing the spores to appear as pale green ovoid bodies. Following a heat-shock of the spores at 70° C., during the first stage of germination, which occurred at about 30 min, red-orange (bright) bodies emerged, followed within one hour by red-orange rod shaped bacilli. About three hours after the initial heat shock, the undamaged control cells became chains of large dividing red-orange cells. Using a calibrated microscopic grid in conjunction with AO staining, direct counts (AODC) were made. This was also used to verify the number of normal or disrupted spores as well as vegetative cells present in the sample throughout the entire incubation period and to document the light scattering profiles that were generated by MALS. In addition, this procedure served as a check on the viable count data.

AO staining provides a method for image analysis by color fluorescence of microbial forms. AO staining is based upon interaction of the dye with nucleic acid (RNA or DNA) to form a red-orange color when viewed by ultraviolet microscopy. *B. subtilis* spores stained with AO and observed using UV microscopy, appeared as pale green ovoid bodies. In the first stage of germination, oblong red-orange cells emerged, the red-orange cells were followed by single red-orange rod-shaped (*bacillus*) cells. Finally, the red-orange rod-shaped cells were followed by large dividing red-orange cells that formed chains.

In addition to providing morphological data involving spore germination, use of a calibrated microscopic grid in conjunction with acridine orange staining permits AO direct counts (AODC) to be performed on each sample thereby verifying the number of spores or vegetative cells or disrupted particles present in the sample. AODC slides were prepared to verify the results obtained with DAWN-B measurements obtained from measurements of control and sterilization treated BIs.

AODC Slide Preparation and Examination

One ml samples of the culture to be counted were placed into small conical vials and the cell culture was fixed by adding 30 μl of a 36.5-38.0% formalin solution. After fixing the culture with formalin for at least about 30 minutes, the sample was either refrigerated or the AO staining procedure was carried to completion. To stain, 100 μl of a 0.1% acridine orange solution were added to the 1.0 ml spore sample and the dye was allowed to react with the spores for approximately five to eight minutes. Polycarbonate membranes (Poretics®, Osmonics, Livermore Calif.) 25 mm in diameter, 0.2 μm porosity, and black in color were soaked in sterile, distilled water for about 5 to 10 minutes. The membranes were then placed on a millipore filter apparatus. One ml aliquots from control or treated samples which had been stained with AO were placed onto the filters and vacuum was applied. The samples were filtered until the fluid was removed. Then, the filter apparatus container from which the fluid had been removed was rinsed with distilled water to ensure that all cells or spores were impinged upon the filter surface. The filter was laid upon a clean microscope slide, a drop of mineral oil applied to the surface of the membrane, and a clean coverslip was laid onto the membrane.

The AODC slide was examined under a microscope using ultraviolet optics (Olympus VANOX-T equipped for light, phase-contrast, and UV-fluorescence microscopy) which microscope was also fitted with photographic and TV Monitoring equipment. A scaled grid in the eyepiece of the microscope permitted the direct counting of the bacterial spores, bacilli, or other bodies that are stained by the dye and which fluoresce under the UV optics. To determine the number of cells/spores in a sample, the number counted in the entire grid was multiplied by $3.3 \times 10^4$ and by any dilution factor of the sample.

Direct Plate Counts on Trypticase Soy Agar (TSA)

All BI samples monitored by the reader with multi-angle light scattering (MALS) were verified by viable plate counts and growth in broth. Before these assays were performed, the performance was compared for three different growth media for making viable plate counts from the spores of *B. subtilis* and *B. stearothermophilus*. These media were Brain Heart Infusion (BHI) Agar, Nutrient Agar (NA) and Trypticase Soy Agar (TSA). TSA provided better growth and gave more consistent results for both species.

Dried spores from the sample vials or glass slides were eluted into sterile distilled water, plated directly, serially diluted (up to $10^{-6}$), and plated onto TSA. After 18 to 24 hours of incubation at 37° C. for *B. subtilis* and 55° C. for *B. stearothermophilus*), the viable colony forming units (CFU) were counted. Plates that had no colonies were incubated for several more days (up to 7 days) to ensure that there were no damaged, but viable spores. From each of the same samples, Trypticase Soy broth was inoculated and incubated for up to seven days to ensure that there were no surviving bacteria in the negative assays.

The spores were eluted from the biological indicator slides or scintillation vials into 20 ml of sterile distilled water and 0.1 ml of the sample was spread onto TSA plates. TSA plates were found to be preferable to nutrient agar in estimating the viable colony forming units (CFU) and were very comparable to the number of spores assessed using AODC. For example, it was routinely found that an AODC count of about $1.7 \times 10^8$ total spores in the control sample gave an average of $1.64 \times 10^8$ CFU from triplicate samples plated on TSA at dilutions of $10^{-5}$ and $10^{-6}$, respectively. In addition, the results from TSA plating demonstrated that virtually all of the spores in the BI test samples were viable.

Electron Microscopy

Scanning electron microscopy was performed on selected samples to determine what effects, if any, treatment by autoclaving, ethylene oxide, or hydrogen peroxide sterilization had on the spore morphology. This was done as a way to verify the MALS profiles generated from normal and sterilized spores as well as an augmentation to the AODC data. Twenty-five μl of 25% gluteraldehyde were added to 1 ml of the spore suspension to fix the sample. The fixed cells were then collected on a Nucleopore filter, washed free of gluteraldehyde with cacodylate-phosphate buffered saline and fixed in 1% $OSO_4$ dehydrated with ethanol or acetone (to 100%), dried under absolute alcohol, and mounted and coated (carbon or silver) and the stubs coated with gold, palladium alloy. The cell preparations were examined by scanning electron microscopy using magnifications in the range of 20,000 to 30,000×. Examples of these micrographs for the steam autoclave runs are presented in Plates 1 and 2. The main distinguishing feature of the treated spores is the collapsed structure, which is a change in the spores' physical structure and, therefore, their light scattering characteristics using MALS as demonstrated in the profiles.

Selected samples were fixed for electron microscopy to determine what effects, if any, treatment by autoclaving, ethylene oxide, or hydrogen peroxide had on the spore morphology. Twenty-five µl of 25% gluteraldehyde were added to 1 ml of the cell suspension to fix the sample for electron microscopy. The fixed cells were then collected on a Nucleopore filter, were washed free of gluteraldehyde with buffer (cacodylate, phosphate buffered saline) three times for 10 minutes each, and the cells were fixed in 1% $OSO_4$ in buffer for 30 to 90 minutes. The cells were dehydrated in successively higher concentrations of ethanol or acetone (to 100%), dried under absolute ethanol, and were mounted and coated (carbon or silver) and the stubs were coated with gold, palladium alloy. The cell preparations were then examined by scanning electron microscopy. Magnifications in the range of 20,000 to 30,000× were used.

Scanning electron microscopy was performed to verify whether the DAWN-B instrument was capable of discerning differences in the spore surface as a consequence of differing sterilization procedures relative to untreated spores.

The Results of the experiments presented in this example are now described.

Four different types of sterilizers were used in the experimental trials described in the following sections. They were the autoclave (steam) sterilizer, ethylene oxide (EO) sterilizer, STERRAD* $H_2O_2$ sterilizer, and ozone sterilizer. The EO, ozone, and H2O2 sterilizers were used to accomplish "cold" sterilization of heat-sensitive medical equipment and supplies. The steam-sterilizer (AMSCO Scientific Series 3031-S (Gravity), Steris Corp., Mentor, Ohio), was programmable for the cycle parameters which includes time, temperature, pressure, as well as for slow (for liquid) and rapid (non-liquid) exhaust. The programmability of the autoclave allowed the flexibility to program the sterilizer for conditions that could result in either successful or unsuccessful sterilization.

The ethylene oxide sterilizer used herein was operated at the Department of Veterans Affairs, Processing & Distribution Section, VAHMCS Baltimore Division (Baltimore, Md.). The sterilizing cycle was fixed to include a 2.5 hour exposure to ethylene oxide followed by a de-gassing cycle of 14.5 hours. A non-biological indicator was used to also monitor the sterilization. A surgicot 2 (Surgicot, Research Triangle Park, N.C.) laminated EO Gas Indicator (Propper Manufacturing Co., Long Island, N.Y.) which registers a change in color after correct processing has been accomplished was used for this purpose.

The $H_2O_2$ sterilizer (STERRAD* 100 # 930349) used herein was operated at the University of Maryland Medical System's Central Sterile Processing facility (Baltimore, Md.). The STERRAD* is a low temperature, plasma-generating, sterilizer whose sterilization cycle consists of vacuum, injection ($H_2O_2$), diffusion, plasma, and vent stages, respectively. The sterilization cycle requires about 70 minutes to complete. The STERRAD* $H_2O_2$ sterilizer is not designed to accommodate liquids (or even small amounts of moisture) or cellulosic based products like linen and paper and the cycle is fixed. The STERRAD* employed a non-biological indicator comprising a Chemical Indicator strip supplied by the manufacturer which changed from red to yellow (or lighter) as compared to the color bar on the strip when exposed to $H_2O_2$ during the processing cycle. Also, a BI (B. subtilis spore strips) was incubated in a nutrient broth for 7 days to determine successful sterilization.

Control Cultures for Sterilization

For all control (untreated) cultures, 1 ml of B. subtilis spores at approximately $1.7 \times 10^8$ spores/ml was the starting challenge dose, regardless of how the challenge was performed for the treatment. The culture was diluted at a ratio of about 1 to 20 in sterile, distilled $H_2O$ and 900 µl of this suspension were added to 15 ml of 5% BHI broth. The suspension was heat-shocked at 70° C. for 10 minutes and was incubated at 37° C. for the duration of the experiment (which was typically four or five hours). For all experiments, plate counts on TSA and AODC slides were performed in order to verify the DAWN-B (MALS) readings. Typical MALS data for a control culture was accompanied by AODC slides and by plate counts on TSA. The sterilization experiments were performed in parallel control with samples which had not been treated to generate parallel control MALS data files. For example, control file was run in parallel with a full STERRAD* cycle. Similarly, a control file was run in parallel with a full Ethylene Oxide sterilization cycle, and control files were run in parallel with the autoclave sterilization data. Analyses on these data were performed to ascertain whether specific detectors were more sensitive for determining the various stages of the spore germination cycle.

Autoclave Sterilized Cultures

The autoclaves used in the studies were AMSCO Scientific Series 3031-S Gravity and 3021-S that were programmable for temperature, time, and pressure (psig). Standard settings of 121° C. and 15 psig were used in all autoclave studies and the exposure times were varied in order to achieve conditions that would give various levels of killing. Initially, sterilization periods of 1, 2, 3, 4, 5, 15 and 30 minutes were evaluated to establish conditions for achieving full sterility and partial killing in a range between 30 and 80% for B. subtilis spores (the preferred biological indictor herein). Having established the appropriate autoclave period, a predicate organism (B. stearothermophilus) was included in the same autoclave batches for direct comparison. The evaluation demonstrated that exposure periods of 2 and 15 minutes gave results that consistently showed partial sterility (2 min) and complete sterility (15 min).

For all autoclave-sterilized cultures, one ml of B. subtilis spores at approximately $1.7 \times 10^8$ spores/ml was dried on a slide, as described previously elsewhere herein, and was used as the challenge dose. After completion of the sterilization cycle, the culture was diluted and suspended in 5% BHI, as described above. The heat-shock step was omitted because the autoclave temperature (121° C.) was sufficient to either initiate germination or to inactivate the spores such that germination did not occur, i.e., sterility is obtained.

Autoclaving was performed at 121° C. and at 15 psi for periods of 1, 2, 3, 4, 5, 15, and 30 minutes using a programmable autoclave (AMSCO Scientific Series 3031-Gravity). AODC and DAWN-B measurements were made on each sample at time intervals of 0 minutes, 30 minutes, 1 hour, 2 hours, 3 hours, 4 hours, and at 24 hours to determine whether germination and growth had occurred. The data regarding steam sterilization (both successful and unsuccessful) are disclosed herein in FIGS. 1-4. Data were also collected for BIs that were immersed within volumes of water ranging from 100 ml to 300 ml, and these data here demonstrated that BIs immersed in liquid were not inactivated unless the autoclave cycle was 30 minutes or longer. These results simply underline the well-established fact that as the load size and volume to be sterilized increases the length of the sterilization cycle must be increased proportionately.

Multiangle Light Scattering Photometer

The MALS photometer Model B (Wyatt Technologies Corp., Santa Barbara, Calif.) was used to examine the biological indicator.

In addition, an Ocean Optics Transmission Spectrophotometer Model USB-2000, with both ultraviolet and visible optics, capable of collecting data for light absorbed and light scattered, was also used to measure the effect of autoclaving on *B. subtilis* spores. It was first verified that the instrument was capable of showing increases in the population of germinating spores, and then used to determine the effects of autoclaving on spores in the absence of incubation.

The Ocean Optics USB 2000 Fiber Optic Spectrophotometer used has a miniature modular design which allows one to choose from 2 detectors, 14 gratings, 6 slits and many accessories that can be used to optimize the system for a specific application, e.g., examination of particles such as microorganisms in order to analyze particles. It accepts light energy transmitted through single-strand optical fiber and disperses it via a fixed grating across the linear CCD array detector. The detector is a 2048-element linear silicon CCD array with an effective range of wavelengths between 200 and 1100 nm. Its dynamic range is $2 \times 10^8$. Its estimated sensitivity is 86 photons/count; also, $2.9 \times 10^{-17}$ joule/count. Its signal-to-noise value at full signal is 250:1 with a dark noise value of 2.5-4.0 RMS. It is capable of resolving particles in the range of about 0.3 nm to 10.0 nm, depending on the groove density of the grating and the diameter of the fiber or width of the slit. Given the *B. subtilis* spore size of about 1 m×1.3 m and a vegetative cell size in the range of about 2 to 3 m, this bacterium is readily visualized with these optic specifications. Multiple wavelengths within the UV-Vis range permits both particle size and molecular content analyses to be done.

MALS Profile for Untreated Control Spores Demonstrates Specific Profiles Correlated to Cell Morphology and Life Cycle Stage of Organism The data disclosed herein demonstrate a typical MALS profile for untreated heat shocked *B. subtilis* spores (FIG. 1). MALS analysis was performed on untreated control spores at selected culture intervals of 0 minutes (set 1), 30 minutes (set 6), 2 hours (set 16), and 4 hours (set 21) post heat-shock treatment (i.e., 70° C. for 10 minutes). The germinating culture was grown in 5% Brain Heart Infusion (BHI) broth, statically, at 37° C. Over a range of θ angles from 25° to 125°, the intensities at each angle changed during the 30 minutes and two hour intervals without a significant change in the number of viable cells (spores/vegetative cells). The lack of increase in cell number was confirmed by acridine orange direct counting (AODC) and by plating of parallel samples onto trypticase soy agar plate (TSA). However, during this period, the spores underwent the morphological stages which lead to formation of the vegetative form of the *bacillus* (i.e., the cells changed from spores to "bright bodies" at 30 minutes and then from "bright bodies" to rod-shaped bacilli). By four hours, bacterial growth had occurred and chains of bacilli had formed. AODC counts increased from $1.77 \times 10^8$ cells at 2 hours to about $2.98 \times 10^8$ at 4 hours and the DAWN-B $N/N_o$ value changed from 1.0 to 2.3.

These data indicate that the MALS measurement detected a meaningful increase in the number of viable organisms which increase corresponded directly to the numbers measured microscopically by AODC and TSA. These data further indicate that MALS measurements may be correlated to biological parameters. The DAWN-B data file and relevant parallel AODC and TSA plate counts were performed contemporaneously.

The data disclosed herein were further analyzed by evaluating the various profiles generated at each time point after heat shock. As stated previously elsewhere herein, FIG. 1 depicts the results of MALS determination of germination/transitions/growth of control *B. subtilis* spores which were heat-shocked and untreated for the MALS measurements taken at the 0 minute (set 1) and 30 minutes (set 6) intervals. The data disclosed indicate that the profile of set 1 (0 minutes) is that of a spore whereas the "bright body" profile is shown by set 6 (30 minutes). The change in the MALS profile at 30 minutes was the first indication that the spore was alive and had the capacity to form vegetative cells capable of forming colonies on solid growth media such as nutrient agar or TSA.

The data disclosed here was further evaluated with respect to the various MALS detectors and further demonstrate that although the number of bacteria did not increase from 0 minutes to 30 minutes during the transition from the spore to the "bright body," the cell morphology changed during that time interval. In addition, the data disclosed herein demonstrate that certain MALS detectors were more sensitive indicators of the morphological change which occurred in the cells during the 30 minute interval. That is, while the $N/N_o$ value (ratio of log-weighted intensities for all detectors) for set 1 to set 6 (0 minutes and 30 minutes, respectively) exhibited no significant difference indicating no increase in the number of cells, there were significant differences in the $N/N_o$ values at certain scattering angles. These are notably different at detectors 1-3 (two-fold difference), a crossing over of the curve plots at detectors 5 and 6, a small difference at detectors 7 and 8, a 20% difference at detectors 11-13, and a slight difference at detectors 13, 14. Without wishing to be bound by theory, these results indicate that the unique differences in MALS profiles between the spore and the "bright body" are emphasized at detectors 1-3 (representing θ scattering angles of 23 to 35°), detectors 5 and 6 (representing 47.2 and 53.5° θ angles—noting that here is a crossover with detector 5 showing a greater value for the spore and 6 showing a greater value for the "bright body"), and detectors 11-13 (representing θ scattering angles of 89 to 106°).

MALS analysis of untreated control spores was performed and a comparison was made between the DAWN-B measurements made at 0 min (set 1) and 2 hours (set 16) on the post-heat shocked culture incubated at 37° C. in 5% BHI broth (FIG. 1). Again, there was no increase in the number of viable organisms and the MALS measurements for sets 1 and 16 give a $N/N_o$ ratio of 1.0. Plate counts and AODC also confirmed the lack of an increase in the number of viable organisms during this time interval. However, the MALS profiles of the two sets differ significantly, corresponding to a spore (set 1) and a *bacillus* (set 16) in the vegetative state (FIG. 1). These differences are especially emphasized at detectors 1-3, detectors 5 and 6, and detectors 11-13. Set 21 (representing 4 hours of growth at 37° C. in BHI broth) exhibited an $N/N_o$ ratio of 2.3 when compared with set 1 and with set 16. This result demonstrates a substantial increase in the number of bacilli (vegetative cells) over the number at 2 hours (set 16). Since the spores germinated and had produced bacilli by two hours and the bacilli had multiplied by four hours, the bacteria were viable. These results were substantiated by the formation of colonies on TSA plates and by a corresponding increase in cell numbers observed by AODC direct counts.

Figure 2:
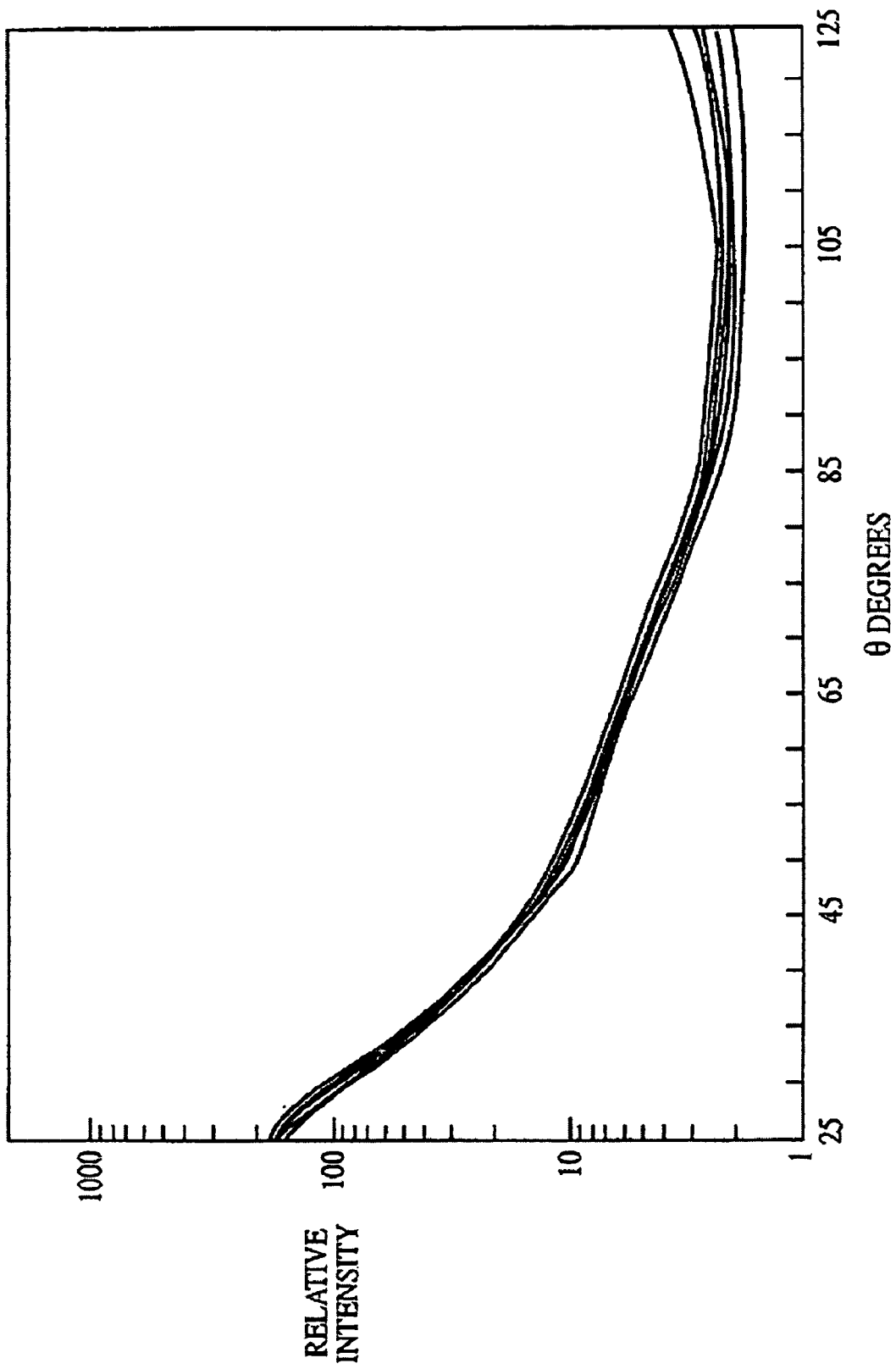

The data disclosed herein demonstrate that effective steam sterilization by autoclaving the spores for 5 minutes at 121° C. under 15 psi of pressure was detected by MALS analysis. Further, the data demonstrate that MALS analysis can detect the effectiveness of steam sterilization treatment. FIG. 2 depicts the light scattering measurements made on the biological indicator (approximately $1.7 \times 10^8$ *Bacillus subtilis* spores dried on a glass slide) following autoclaving at 121° C./15 psi for five minutes. There were no changes in the DAWN-B profiles observed over a 24 hour period, demonstrating that all of the organisms had been killed. None of the transitional morphologies exhibited by untreated spores were detected in the autoclaved BI, also indicating that sterility was attained by this treatment. These results were verified by both plate counts on TSA and AODC slides, which demonstrated that no colonies were formed and that none of the typical germination morphologies appeared in the BI even after 24 hours or more of incubation in BHI.

Additional analysis of the MALS profiles generated by steam-killed spores was performed which compared the 0 minute sample with 30 minutes, 2 hours, and 24 hours measurements. These comparisons demonstrated that the morphological transition forms characteristic of normal germination did not appear in autoclave sterilized BI. Furthermore, changes at the most sensitive detectors at unique angles (FIG. 2) failed to occur. These data constitute proof that the spores were killed by the sterilization procedure, which was verified by TSA plate counts done in 10 replicates. In addition, duplicate data for a second BI gave the same results for both the DAWN-B measurements and 10 TSA replicate plates.

Thus, the assay disclosed herein made it possible to rapidly and efficiently determine the efficacy of steam autoclave sterilization within only a short period of time without the need for methods requiring complex and time-consuming sample processing such as AODC and TSA plating.

MALS Detection of Insufficient Sterilization

Figure 3:
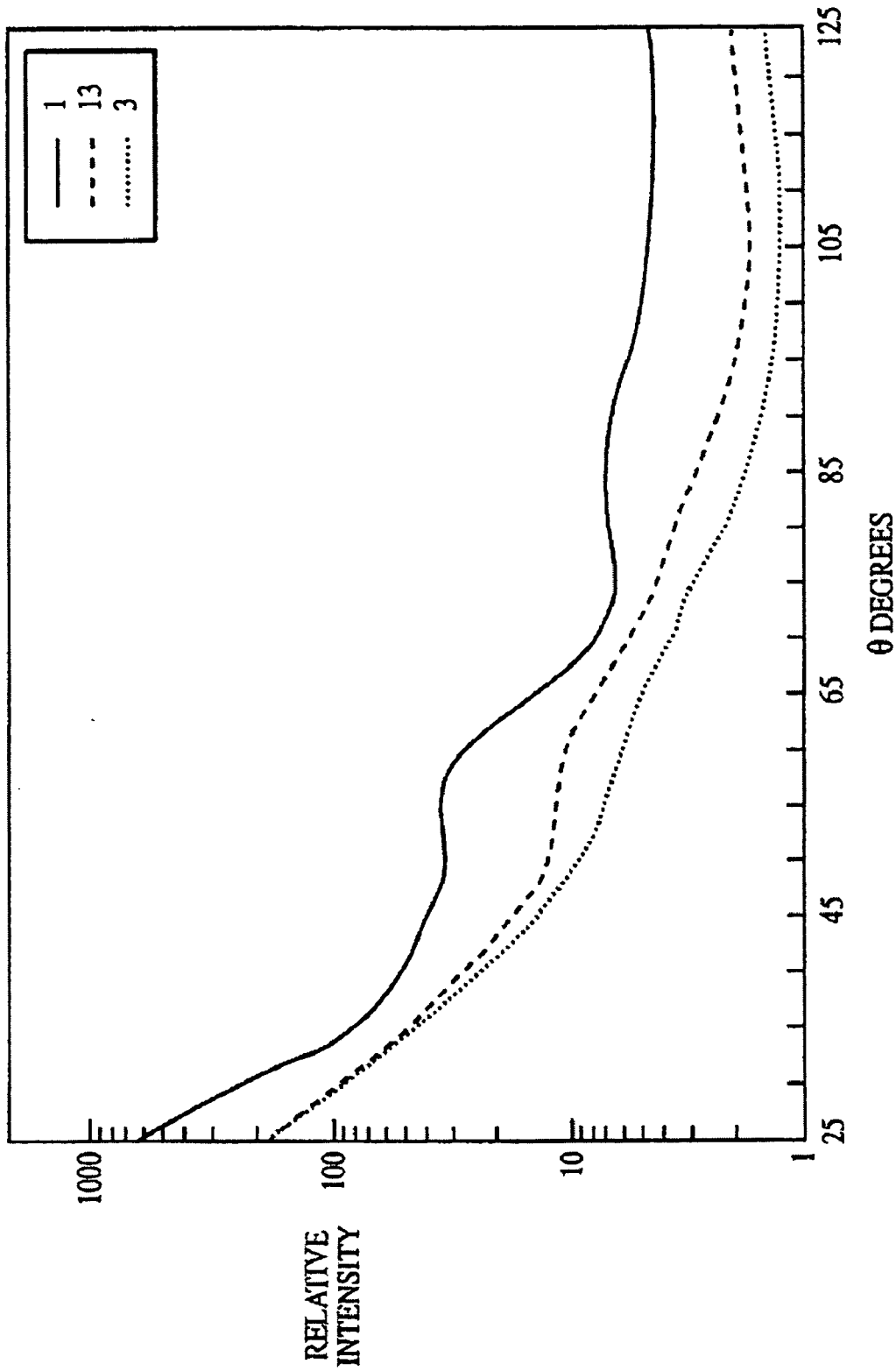

Spores treated under conditions known to be insufficient to produce sterility were also examined by MALS analysis. That is, the data disclosed herein demonstrate the results of autoclaving the biological indicator for 3 minutes at 121° C. and 15 psi (FIG. 3). Three sample incubation intervals were examined post treatment, i.e., 0 minutes, 1 hour, and overnight plus an additional 6 hours of incubation (24 hours total). The additional six hour incubation was performed after the addition of an another 5% BHI, thereby bringing the concentration to 10%, which was necessary for growth of any "injured" cells.

Parallel twenty-four hour TSA plate counts were also performed and the data disclosed herein demonstrate that the viable spore population was reduced from $1.79 \times 10^8$ colony forming units (CFU) to $2.12 \times 10^5$ CFU by incomplete autoclave sterilization. The plates also exhibited colonies of variable sizes further indicating varying degrees of cell damage and recovery under these autoclaving conditions. Duplicate data confirmed these results.

Figure 4:
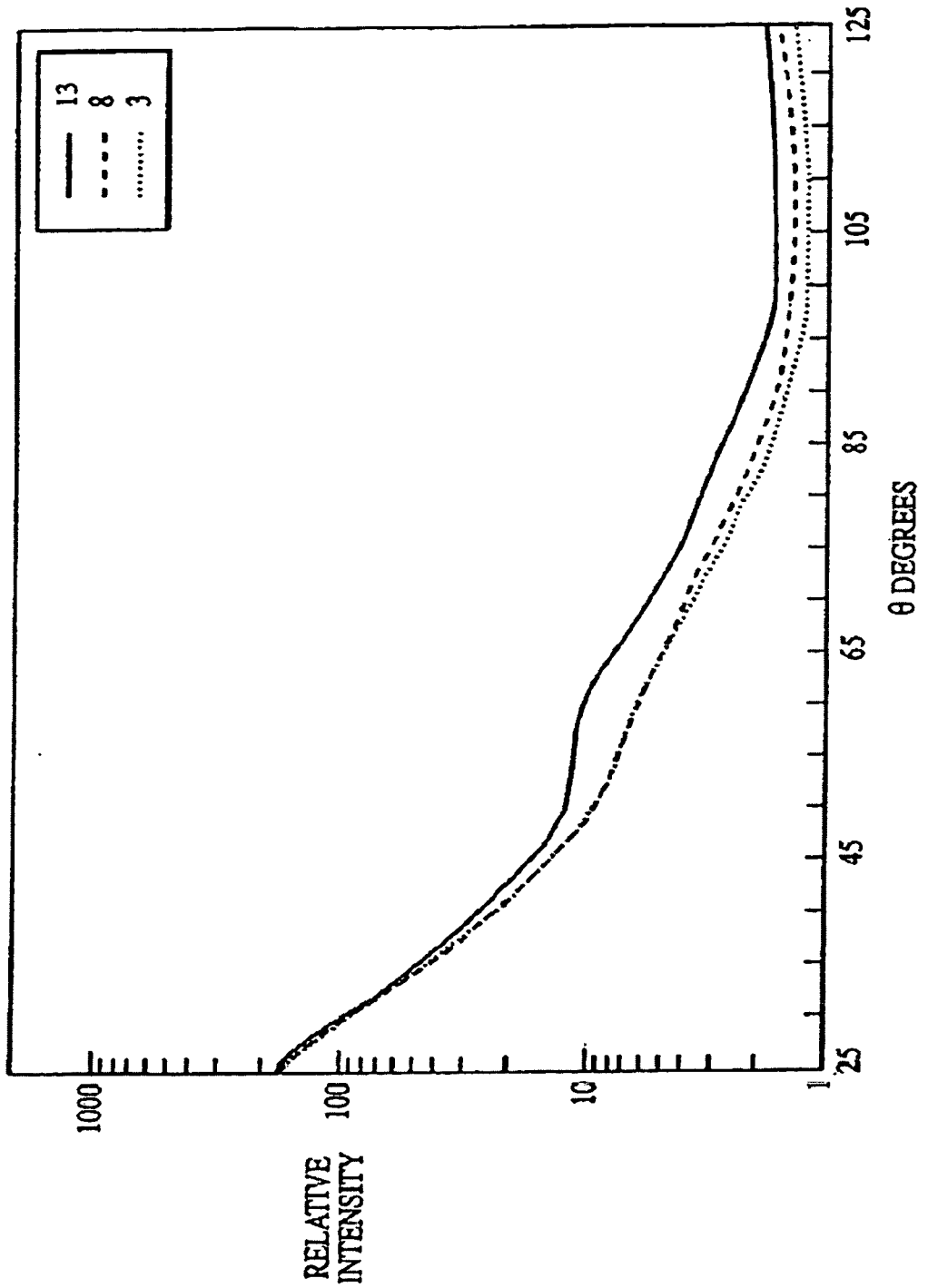

The light scattering data at intervals of 0 minutes, 30 minutes, and 1 hour following autoclaving at 121° C./15 psi for 3 minutes and incubation in 5% BHI were also compared (FIG. 4). There was a change in the cell morphology at 30 minutes of incubation, but after one hour of incubation, evidence of incomplete sterilization was observed since there was a change in the profile showing a change from the spore to the *bacillus* form. The data disclosed herein also demonstrate that the predicted changes in morphology occurred during incubation, i.e., intensity increases were observed at detectors 5, 6 and at detectors 11-13. These results were verified by TSA plate counts and AODC which demonstrated that only a three log kill was achieved at three minutes of autoclaving.

Ethylene Oxide Sterilized Cultures

For all ethylene oxide (EO) sterilized cultures, the BI challenge was with one ml of *B. subtilis* spores at a concentration of approximately $1.7 \times 10^8$ spores/ml which were air-dried on a glass slide, as described previously elsewhere herein. After completion of the EO sterilization cycle, the BI culture was diluted and the spores were suspended in 5% BHI, as described above. The culture was diluted to the same concentration as the Control (untreated) BI as described previously herein and the sample was heat-shocked at 70° C. for 10 minutes. Following heat-shock, the sample was incubated at 37° C. for 24 hours to ensure that viable cells could be detected if present. MALS analysis was performed at 0 minutes, 30 minutes, 1 hour, 2 hours, 3 hours, and 4 hours, and parallel samples were taken for AODC slides at those same time points. Direct plating on TSA was also performed to further determine the presence of viable cells.

The data disclosed herein (FIG. 5) demonstrates the data of four independent BIs and the parallel control BI illustrating the effects of EO on spores dried onto a solid support and subjected to EO sterilization. Comparison of these data to those data collected for EO samples immersed within 10, 50, and 100 ml of water, which were all positive for bacterial growth, demonstrated that killing can be incomplete during a normal EO cycle if the gas cannot penetrate the matrix, therefore, liquid samples are not considered appropriate for EO sterilization since the water-insulated BIs all exhibited positive growth. In sum, the data disclosed herein demonstrate that the BIs dried onto a solid support were killed whereas the water insulated BIs still had live organisms present.

Figure 5:
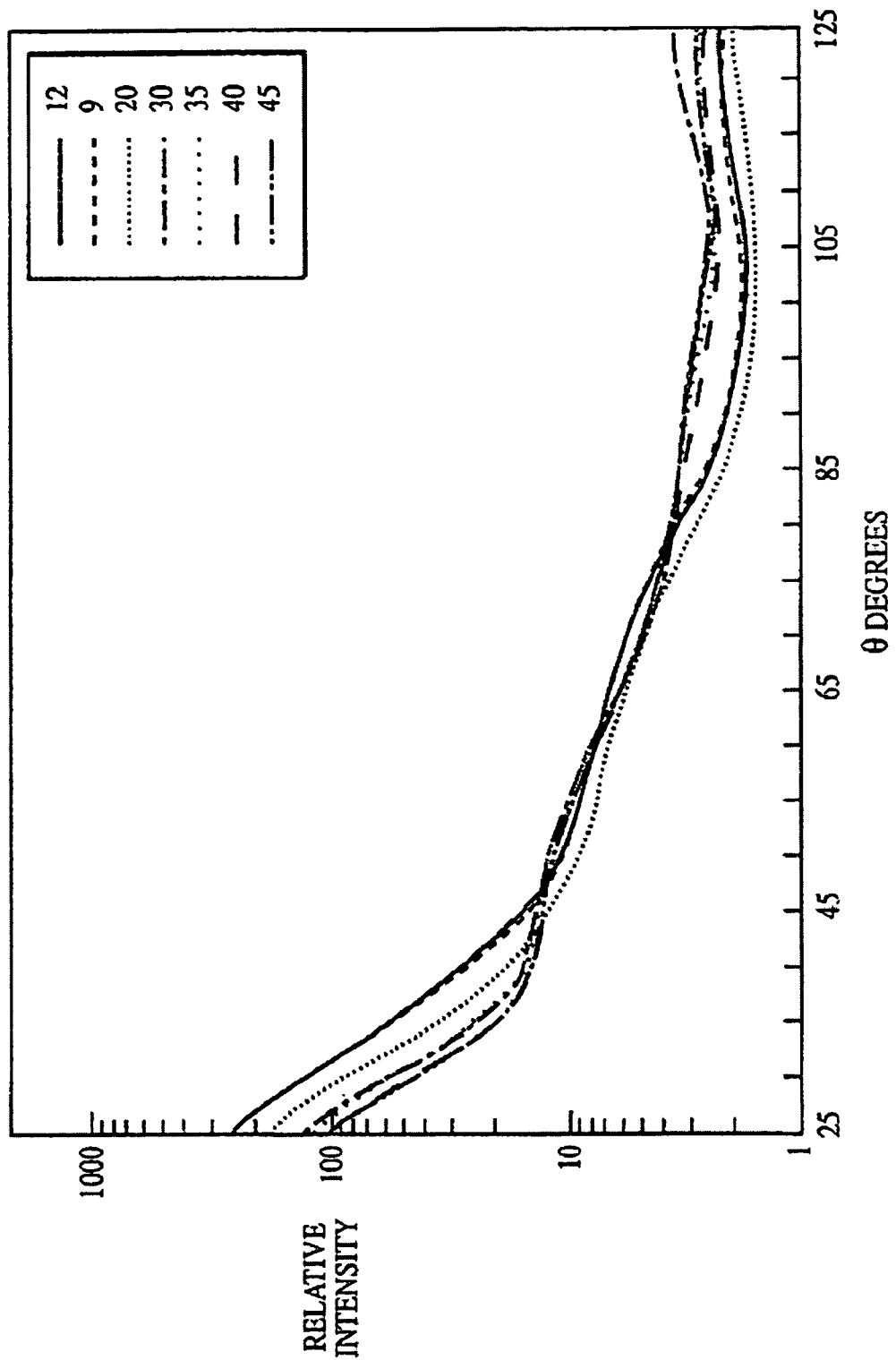

FIG. 5 discloses the results of MALS measurements obtained from a *B. subtilis* BI sterilized by Ethylene Oxide (EO). The morphological profiles demonstrated changes, but growth never occurred as evidenced by both AODC slides and ten TSA plates each performed to detect viable spores obtained from four independent BIs. This figure compares the light scattering patterns throughout a four hour period during which there was an initial change in the morphology at 30 minutes with no further changes. During the entire four hour period, there were no increases in the number of spores/germination bodies.

The MALS profiles for spores treated with EO and incubated for 0 minutes post-heat-shock (set 9) were compared to that of BI incubated for 30 minutes post-heat-shock (set 20). At 30 minutes, increases in intensities at detectors 5, 6 and 11-13 occurred and by 2 hours, the morphological differences were even more pronounced at detectors 1-3, 5, 6, and 11-13. The data disclosed herein further demonstrate that detectors 1-3, detectors 5 and 6, detectors 7 and 8, and detectors 11-13, demonstrate the differences in MALS profiles at selected detectors between 0 minutes and 2 hours of incubation after EO sterilization as depicted in FIG. 5. These early morphological changes were not accompanied by increased cell numbers and the MALS measurements do not indicate any evidence for growth. Further, the morphologies exhibited at 30 minutes through 4 hours do not exactly correlate to those exhibited by an untreated (control, set 12) culture, indicating that, without wishing to be bound by theory, the EO treatment resulted in a damaged germinating body. TSA plates exhibited no viable colonies and AODC slides demonstrated no increase in direct counts.

$H_2O_2$ (STERRAD*) Sterilized Cultures

For all $H_2O_2$ sterilized cultures, the BI challenge was one ml of *B. subtilis* spores at a concentration of $1.7 \times 10^8$/ml which were air-dried onto a glass slide as described previously elsewhere herein. After completion of the STERRAD Cycle of approximately 70 minutes, the BI culture was diluted and the cells were suspended in 5% BHI, as described above. The culture was diluted to the same concentration as the control BI and the sample was heat-shocked at 70° C. for 10 minutes and incubated at 37° C. for 24 hours to detect any viable cells present. MALS measurements were obtained at 0 minutes, 30 minutes, 1 hour, 2 hours, 3 hours, 4 hours, and 4.75 hours, and parallel samples were obtained for analysis by AODC direct counting. Direct plating on TSA was also performed to determine the presence of viable cells. The combination of AODC, which detects the total number of spores and/or vegetative cells and the various life stages thereof, and plate counts on TSA, which gives the number of cells capable of forming colonies (live cells), were correlated with the MALS at selected detectors to determine whether sterility has been attained.

Figure 6:
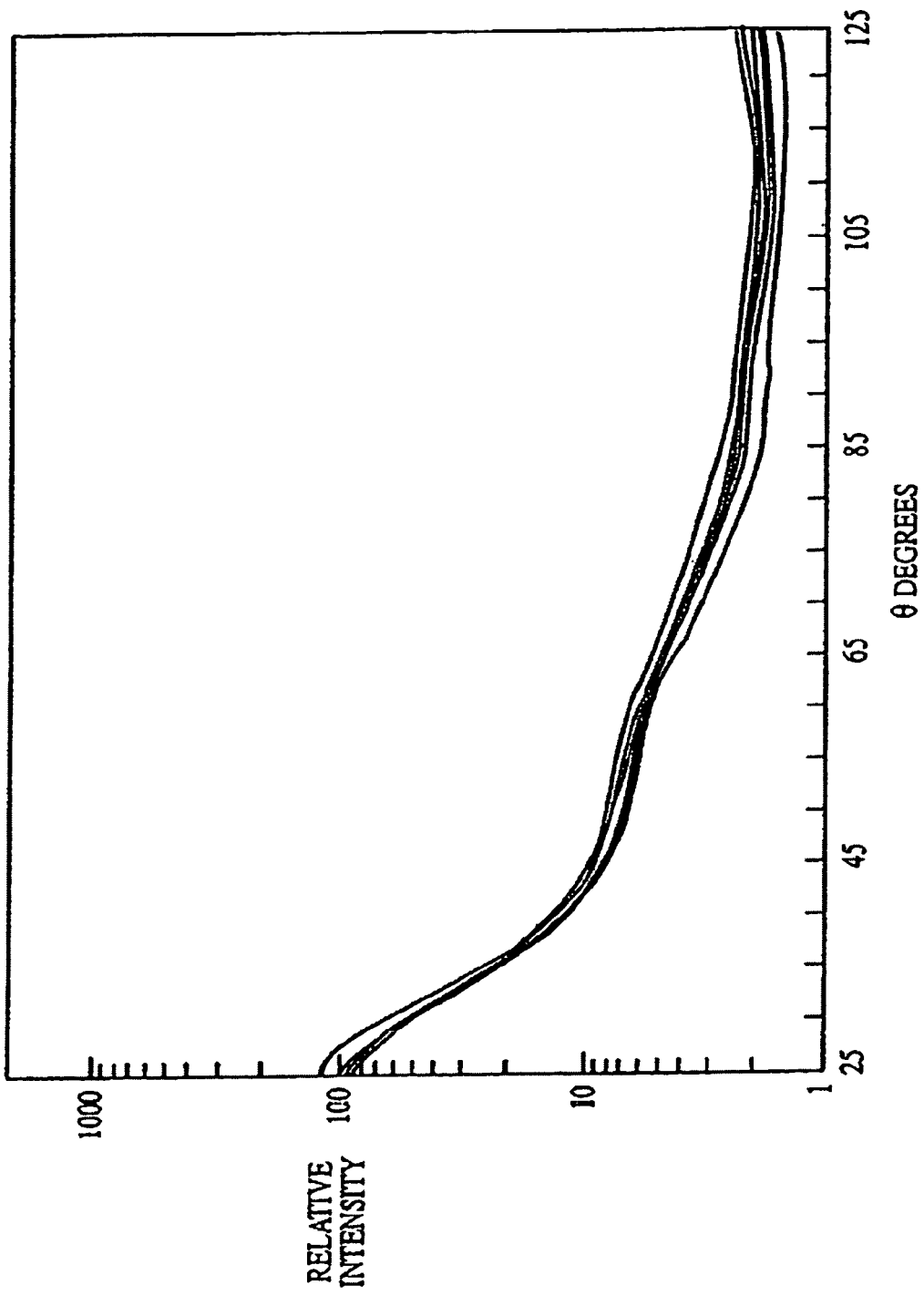

MALS measurements were obtained from *B. subtilis* BI following sterilization with STERRAD* ($H_2O_2$) and incubation of the samples in 5% BHI at 37° C. over a 22 hour period (FIG. 6). The data disclosed herein clearly indicate that no growth had occurred and direct counts on TSA (10 plates on each of the triplicate samples) supported this result since there was no growth on any plate. AODC slides demonstrated that the sterilized spores deteriorated during the incubation intervals that followed. Only one morphological change, i.e., early germination, appeared to have occurred (between the 0 minutes to 30 minutes time interval), but thereafter the cells deteriorated and no further growth occurred.

The MALS profile of BI which had not been sterilized (Control at 0 minutes) was compared with the profile of $H_2O_2$-sterilized BI after 3 hours of incubation (FIG. 6). The data disclosed herein demonstrate that a morphological change occurred after $H_2O_2$ sterilization despite the absence of growth. The $N/N_o$ value (ratio of numbers of cells with respect to number of cells in the original sample) remained 1.0 suggesting that there was no increase in the number of particles. This change in morphology was shown to be reproducible by triplicate measurements made on different BIs over a four hour period without any further changes in the number of cells and without these cells being viable, i.e., no colonies were detected when the putatively sterilized sample was plated onto TSA media.

Figure 7:
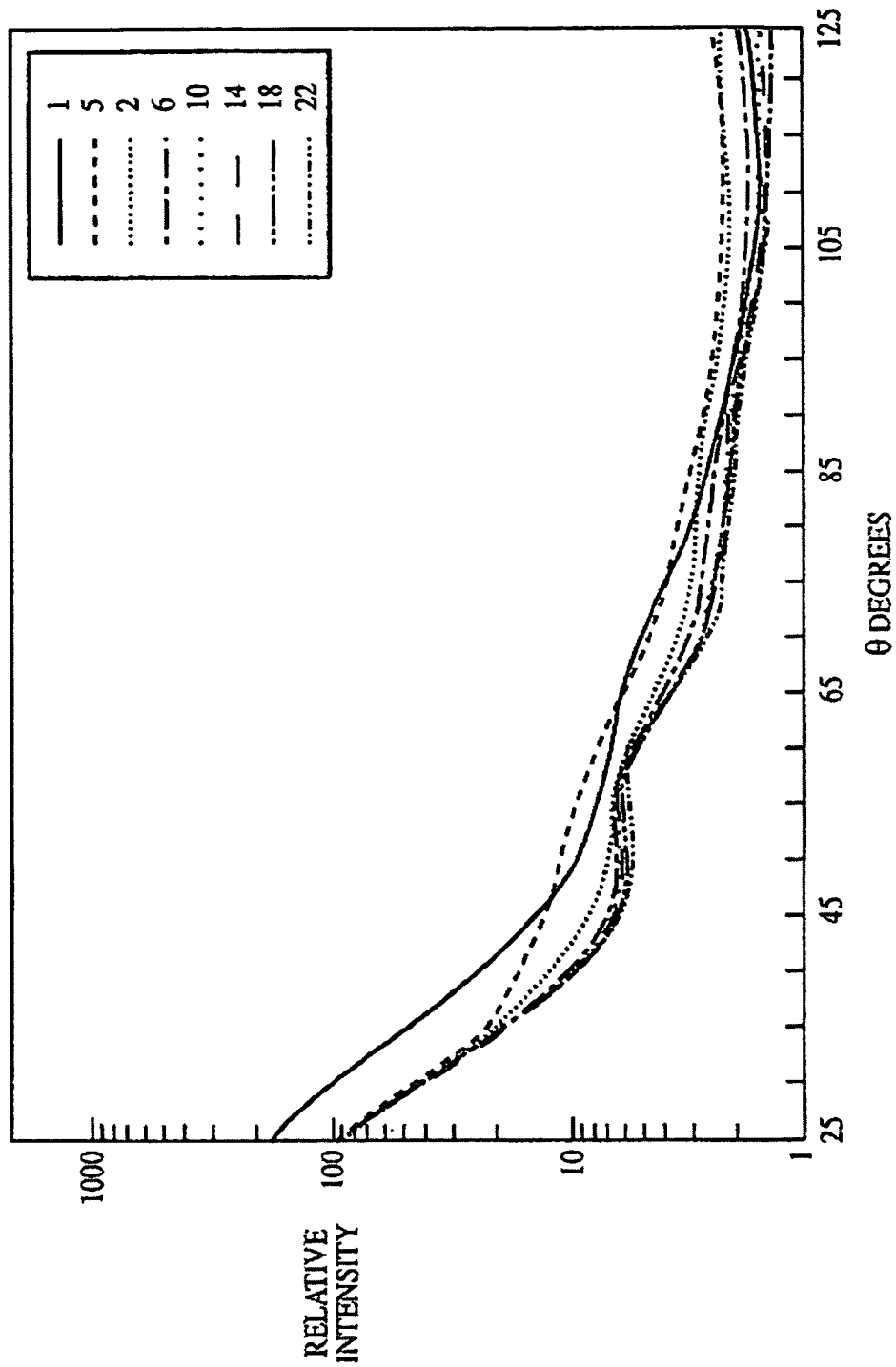

The MALS profiles of untreated, control spores (0 minutes and 30 minutes post-heat-shock) were compared to the profiles obtained from spores sterilized with $H_2O_2$ and incubated for various intervals following heat-shock (FIG. 7). The data disclosed herein demonstrate that the morphologies of the non-sterilized, but heat shocked, spores exhibited the characteristic early germination profile. This germination form was followed by successive changes leading to the *bacillus* form and, eventually, to bacterial growth as shown in FIG. 1. The morphologies of the treated spores also exhibited altered MALS profiles beginning at 0 minutes after sterilization but the spores did not demonstrate any further changes or germination progression over the entire 4 hour incubation period. However, there were slight, but progressive increases in intensity detected at the greater angles with continued incubation. Without wishing to be bound by theory, the increases at greater angles may be due to cellular breakdown of the organisms and may represent the appearance of cell fragments. AODC slides taken from parallel samples demonstrated that there debris was present and was likely due to cellular breakdown, thereby accounting for the smaller particles (cell fragments) present after 4 hours of incubation.

Correlation of MALS BI Sterilization Detector to Other Methods

Over a four hour period, untreated heat-shocked spores of *Bacillus subtilis* germinated and progressed through several transitional stages which included a spore stage, a germination body state, several intermediate forms, the mature *bacillus* stage, and the stage exhibiting dividing cells. The acridine orange staining procedure (AODC) described elsewhere herein has the capability of showing which of these morphological stages are present at any given time during the germination process (Bruno and Mayo, 1995, Biotech. Histochem. 70: 175-84; Sharma and Prasad, 1992, Biochem. Histochem 67:27-29). The data disclosed herein demonstrate that AODC detected an initial spore stage (initially visible as small and green and shaped ovoid), followed by "bright bodies" (bright red-orange or simply bright yellow-green), followed by intermediate forms (orange), mature bacilli (larger and orange) which were, in turn, followed by dividing bacilli (red-orange) giving rise to chains of bacilli.

Multi-angle light scattering (MALS) measurements were made on all of these stages of germination and scanning electron microscopy was also performed on selected samples done in parallel with MALS and AODC. The data disclosed herein demonstrate that MALS measurements are correlated to the stages involved in germination and growth from the spore. Further, the data disclosed herein demonstrate that MALS measurements may be used to determine the effect, if any, of sterilization treatment on the morphology of treated spores and on their subsequent germination and post-germination morphologies.

The data disclosed herein demonstrate that MALS measurements are useful for detecting morphological changes in and/or growth of *B. subtilis* spores as measures of cell viability and as an indicator of efficiency of cell killing by various sterilization methods.

The data disclosed in FIG. 1 demonstrate the MALS measurements for 15 photoreceptors for *B. subtilis* spores which were untreated but which were heat-shocked (70° C. for 10 minutes) to induce germination (Control). MALS measurements were taken at various time points after inoculation of BHI cultures with an equal number of untreated Control spores: set 1 (0 minutes), set 6 (30 minutes), set 16 (2 hours), and set 21 (4 hours).

There was excellent correlation between the MALS measurements made at 0 minutes, 30 minutes, 1 hour, and 2 hours and the morphological changes that could be observed in a normal germinating culture using AODC and scanning electron microscopy. The transition from the spore stage to mature *bacillus* was detected by MALS wherein significant differences were seen in the MALS profiles at 0 minutes, 30 minutes and two hours. Unique profiles representing the spore, the early germination body, and the mature *bacillus* forms were present at 0 minutes, 30 minutes and 2 hours, respectively. By 4 hours, significant cell division and chain formation had occurred as evidenced by AODC and, again, changes in the MALS profile were correlated to the increase in the number of cells. These differences were especially detected by the change in intensities at detectors 1 to 3 ($\theta$ of 23° to $\theta$ of 35°), 5 and 6 ($\theta$ of 47° to $\theta$ of 53.5°), and detectors 11 thru 13 ($\theta$ of 89° to $\theta$ of 106°).

When the biological indicator cultures were sterilized in the autoclave, by hydrogen peroxide, and by ethylene oxide, morphological differences were obvious within 30 minutes, and it could be confirmed that the cells were nonviable by two hours. The profiles of the autoclaved spores were changed by steam sterilization, ozone, and by hydrogen peroxide at 0 minutes, and scanning electron microscopy also demonstrated that the spores had been damaged and had a corresponding difference in appearance, i.e., the spores appeared to be collapsed and were generally more elongated than untreated cells. Thus, the data disclosed herein demonstrate that for steam, and ozone sterilization treatments, examination of the BIs using MALS directly after treatment can be used to assess the efficacy of the sterilization treatment without need of any incubation. This is a dramatic and critical improvement upon prior art methods and systems for assessing the efficacy of sterilization and disinfection treatments.

In the case of ethylene oxide sterilization, the spore did not show great differences compared with untreated spores, but the MALS profile of the early germination body was clearly distinguishable from that of the normal germination body. The action of ethylene oxide is associated with its ability to react with DNA and cause mutations. Without wishing to be bound by theory, the mechanism for the cytocidal effect of EO may explain why the difference in morphology occurs during germination stage rather than in the spore stage, i.e., the nucleic acid modifications caused by EO may lead to altered mRNA expression resulting in altered protein structure resulting, in turn, altered early germination body morphology. In any event, the data disclosed herein demonstrate that for ethylene oxide sterilization treatment, although the assessment of efficacy of the treatment is not as rapid as for steam, ozone and hydrogen peroxide, the present methods yield results within 4 fours which is a vast improvement over prior art methods.

EXAMPLE 2

The experiments presented in this example are summarized as follows.

The data disclosed herein clearly demonstrate that multiangle light scattering (MALS) can be used to monitor the efficacy of steam sterilization or ozone disinfection/killing and that the MALS measurements can be made on samples directly after treatment obviating the need for an incubation period before the efficacy of the treatment can be determined. The DAWN-F was the photometer used in the experiments described herein. The MALS data disclosed herein were supported by direct counts made by staining with acridine orange (AODC) and by survival as measured by colony forming units (CFUs) on trypticase soy agar media.

In addition, broth cultures incubated for up to 7 days consistently demonstrated that there was growth in the incompletely sterilized samples and also demonstrated the absence of growth when sterilization was complete. These data were also supported by the 3M Attest™ (Test Kit 1296™) when the spore strips containing *B. stearothermophilus* were incubated for at least 24 to 48 hours. The data also show that *B. subtilis* spores are a preferred biological indicator, and because the organism grows rapidly one can assess sterility directly and the results can be confirmed within 2 to 4 hours by showing the absence of growth in brain-heart infusion (BHI) broth as detected by MALS measurement.

The Materials and Methods used in the experiments presented in this example are now described.

Test Bacterial Strains

*B. subtilis* was selected as a preferred strain because the spores of this strain are highly resistant to both steam and cold sterilization. In the tests described herein, the spore suspensions used were prepared using spores from Difco strain 0981-50 of *B. subtilis, B. subtilis* strain 168 wild type (168WT), and *B. stearothermophilus*. Difco strain of *B. subtilis* prepared spores (*B. subtilis* spore suspension No. 2, L-00537-02, Lot 128078, Difco) at a concentration of $2\times10^8$ spores per milliliter were used as the standard test organism and *B. subtilis* 168WT and *B. stearothermophilus* were used to provide test comparisons.

All spore suspensions were adjusted to nominal concentrations of approximately $2\times10^8$ spores per milliliter in distilled water, and 1 milliliter of the suspension was air dried for 24 hours in the bottom of a glass vial under sterile conditions in a laminar-flow hood.

Since *B. stearothermophilus* is routinely used for assessing steam sterilization, the 3M Test Kit 1296™ (3M Health Care, S1. Paul, Minn.), which uses this *bacillus* strain as a BI, was used as an additional control for testing the efficacy of steam sterilization. *B. stearothermophilus* is the predicate for steam sterilization since it is believed that this thermophilic bacterium is more resistant to heat-based sterilization treatment than other bacteria.

Steam Sterilization Testing Procedure

Steam sterilization was performed at about 121° C. at 15 pounds per square inch using AMSCO programmable autoclaves (AMSCO Scientific Series 3021-S and Series 3031-S, Steris Corp., Mentor, Ohio). Exposure intervals of 0, 2, 5, 10 and 15 minutes were used initially to determine successful sterilization as determined by multi-angle light scattering (MALS), direct counts by acridine orange staining counts (AODC), colony-forming units (CFU) on trypticase soy agar (TSA), and growth in liquid broth for 3 to 7 days. The data disclosed herein demonstrate that autoclaving for 2 minutes consistently gave incomplete sterilization and was the optimum for comparison with complete sterilization, i.e., 15 minutes.

The MALS instrument used was the DAWN Model F (Wyatt Technology Corp., Santa Barbara, Calif.), which is a flow-through instrument permitting the liquid from a sample to pass through a flow cell while continuously making measurements on the particles as they pass through the cell. Otherwise, the instrument is virtually identical to the DAWN Model B previously described elsewhere herein.

Ozone Sterilization/Disinfection Testing Procedure

Ozone model CD-1B (Aqua-Flo, Inc., Baltimore, Md.), equipped with voltage regulator and oxygen flow controls was used to generate an ozone doses of 0.3 to 0.35 ppm in water. Ozone was generated from oxygen, supplied from an oxygen tank with $O_2$ purity of more than about 99.9%. The generator was fitted with a voltage regulator and an oxygen flow regulator which enabled the precise setting of oxygen flow and voltage parameters such that the desired concentration of $O_3$ could be maintained continuously. An oxygen flow rate of 8 ft$^3$/hr, at 5 psi, and approximately 70 to 80 amps was used to generate the concentrations specified. Excess (head) ozone was passed through a platinum catalyst that converted it back to oxygen where it was released into a vented chemical safety hood.

By the use of toggle switches, the ozone was directed through glass spargers into either of two specifically designated 2-liter Erlenmeyer flasks containing one liter of distilled water. Either a solution of a test chemical or a suspension of microorganisms, or both, was introduced into the flasks via tubes at the top, which passed into the flasks through rubber stoppers that sealed off the system. Samples could be withdrawn at the bottom of the flasks by opening a stopcock. The ozone concentrations were measured using chemical oxidation of indigo dye using an Ozone Pocket Colorimeter™ per manufacturer's instructions (HACH, Inc., Loveland, Colo.). Bacillus spores, at a concentration of $2 \times 10^6$ spores/milliliter were exposed to ozone for treatment times of 0, 5, 10, 15, 20, and 30 minutes, after which times they were measured by MALS, AODC, and CFU, respectively.

Ozone sterilization using humidified ozone gas as a sterilant was selected as a form of cold sterilization that could be quantified according to its "kill" efficacy. The Ozone Generator used was a Model CD-1B (AQUA-FLO, Inc., Baltimore, Md.). Ozone was generated from oxygen, supplied from an oxygen tank with O2 purity of more than about 99.9%. The generator is fitted with a voltage regulator and an oxygen flow regulator which enables the precise setting of oxygen flow and voltage parameters such that the desired concentration of $O_3$ can be maintained continuously. The generator also permits that a desired level of $O_3$ be attained and then the ozone is allowed to revert back to $O_2$ based on its half-life. As oxygen flows through the generator, high voltage converts it to ozone, which is bubbled into water. Excess (head) ozone passes through a platinum catalyst that converts it back to oxygen where it is released into a vented chemical safety hood.

By the use of toggle switches, the ozone is directed through glass spargers into either of two specifically designed 2-liter Erlenmeyer flasks containing one liter of distilled water. Either a solution of a test chemical or a suspension of microorganisms, or both, was introduced into the flasks via tubes at the top which pass into the flasks through rubber stoppers that seal off the system. Samples can be withdrawn at the bottom of the flasks by opening a stopcock. The ozone concentrations were measured using chemical oxidation of indigo dye using an Ozone Pocket Colorimeter™ per the manufacturer's instructions (HACH, Inc., Loveland, Colo.).

The Results of the experiments presented in this example are now described.

Steam Sterilization

Vials containing the dry spores of B. subtilis (Difco), B. subtilis 168WT, or B. stearothermophilus were autoclaved for either 2 minutes or 15 minutes, or were not autoclaved (control). To each of the vials, after treatment, was added enough sterile deionized water or 5% Brain Heart Infusion (BHI) broth to give a final spore concentration of $2 \times 10^6$ spores per milliliter. MALS measurements were made immediately after treatment and without incubation because it could be shown that the extent of the spore kill could be determined directly from the MALS measurements. FIGS. 8, 9, and 10 are the graphic displays for spores of B. subtilis (Difco), B. subtilis (168WT) and B. stearothermophilus, respectively, before autoclave exposure (control), exposure for 2 minutes and exposure for 15 minutes. All measurements were taken before any incubation, so any differences reflected only killing or damage caused by the autoclave treatment. The graphics of FIGS. 8, 9, and 10 clearly show that a 2-minute autoclave exposure caused a drop in the relative intensities at all scattering angles for each of the spore samples. For the B. subtilis strains, there was a much greater drop in relative intensities after a 15-minute autoclave exposure. For B. stearothermophilus, the 2 minute autoclave exposure gave a much more significant decrease in scattering intensities than was seen for the B. subtilis strains, therefore, the additional decrease for the 15-minute autoclave exposure was not so dramatic.

The results of the MALS measurements were validated and could be interpreted by performing AODC and CFU determinations on the same samples. The AODC assays gave a direct visualization of the spores and enabled us to directly count the spores that were present before and after treatment, whereas plate counts (CFU) showed how many of the spores were viable. Tables 1A, 1B, and 1C show direct comparisons of MALS measurements to AODC and CFU analyses of spores and their survival before and after autoclave exposures. Data represented include Table 1A for B. subtilis (Difco), Table 1B for B. subtilis (168WT), and Table 1C for B. stearothermophilus. From Table 1A, it is clear that a two minute autoclave exposure caused a significant reduction in the number of viable spores, but that approximately half are still alive (i.e., CFU counts were 48.5% of the control population). In contrast, an autoclave exposure of 15 minutes resulted in no survivors (i.e., CFU counts were 0% of the control population). From Table 1B, it is clear that a two-minute autoclave exposure caused a significant reduction in the number of viable spores for B. subtilis 168WT, but that about 25% were still alive. After 15 minutes of exposure, there were no survivors. From Table 1C, it is clear that over 90% of the B. stearothermophilus spores were killed from a two-minute exposure and that virtually all were killed after 15 min (nearly 6 log kill), however, for most B. stearothermophilus samples autoclaved for 15 min, there were no survivors.

These data show that MALS measurements can be used to determine killing of spores by autoclave treatment, and that the measurements are directly correlated with the extent of killing/survival. Survival measured by colony forming units on agar plates validated the assumption that decreases in light scattering intensities were due to damaging or killing spores i.e., the number of normal spores in the population decreases with increasing time of autoclave exposure. AODC observations showed that there was a reduction in the number of spores with normal appearance, but that some of the spores still visible by AODC were non-viable.

Vials containing the dry spores of B. subtilis (Difco), B. subtilis 168WT, or B. stearothermophilus were autoclaved for either 2 minutes or 15 minutes, or were not autoclaved (control). To each of the vials, after treatment, was added enough 5% Brain Heart Infusion (BHI) broth to give a final spore suspension of approximately $2 \times 10^6$ spores per milliliter.

The control spore suspensions were heat-shocked at 70° C. for 10 minutes and then cooled to the appropriate incubation temperature for each species/strain. The incubation temperature for the two B. subtilis strains was 37° C. and the incubation temperature for the thermophile, B. stearothermophilus, was 55° C. The autoclaved spore suspensions were not heat-shocked because the autoclaving temperature was sufficient to initiate germination if any.

MALS measurements were made directly after treatment and at hourly intervals following incubation. Samples were removed at the 0 hour interval for making plate counts on TSA and additional samples were fixed in formalin for acridine orange staining. The data obtained for measurements made on samples taken directly after treatment are disclosed in Table 1A for Bacillus subtilis (Difco) spores, Table 1B for Bacillus subtilis 168WT spores, and Table 1C for Bacillus stearothermophilus spores.

TABLE 1A

| Treatment time (min) | MALS | | AODC | | CFU | | |
|---|---|---|---|---|---|---|---|
| | Average Intensity | % of control | Spores per ml | % of control | CFU/ml | % of control | % of AODC |
| 0 | 2294 | 100 | $2.70 \times 10^6$ | 100 | $2.00 \times 10^6$ | 100 | 74 |
| 2 | 1921 | 83.7 | $1.33 \times 10^6$ | 49.2 | $9.70 \times 10^6$ | 548.5 | 72.9 |
| 15 | 1267 | 55.2 | $1.25 \times 10^6$ | 46.2 | 0 | 0 | 0 |

TABLE 1B

| Treatment time (min) | MALS | | AODC | | CFU | | |
|---|---|---|---|---|---|---|---|
| | Average Intensity | % of control | Spores per ml | % of control | CFU/ml | % of control | % of AODC |
| 0 | 4028 | 100 | $2.21 \times 10^6$ | 100 | $2.84 \times 10^6$ | 100 | 100 |
| 2 | 2374 | 59 | $1.00 \times 10^6$ | 45 | $6.89 \times 10^5$ | 24 | 69 |
| 15 | 1517 | 38 | $7.60 \times 10^6$ | 35 | 0 | 0 | 0 |

TABLE 1C

| Treatment time (min) | MALS | | AODC | | CFU | | |
|---|---|---|---|---|---|---|---|
| | Average Intensity | % of control | Spores per ml | % of control | CFU/ml | % of control | % of AODC |
| 0 | 2891 | 100 | $1.74 \times 10^6$ | 100 | $6.27 \times 10^6$ | 100 | 600 |
| 2 | 741 | 25 | $4.80 \times 10^6$ | 27 | $4.00 \times 10^4$ | 0.65 | 8.5 |
| 15 | 579 | 20 | $5.10 \times 10^5$ | 23 | 67‡ | 0.001 | 0.02 |

Note.
Average intensity is the log weighted average of intensities at all detectors. Colony forming units (CFU) were determined after 24 hours incubation. The results indicated by "‡" reflect that 20 of 25 plates in the undiluted sample did not exhibit growth after incubation.

These data demonstrate that MALS intensity measurements decrease directly following autoclave treatment. Further, these data, which are depicted graphically in FIG. 8, demonstrate that AODC direct counts and the number of colony-forming units (viability counts) also decrease correspondingly for *B. subtilis*-Difco (FIG. 8A), *B. subtilis* 168WT (FIG. 8B), and *B. stearothermophilus* (FIG. 8C).

Figure 8A:
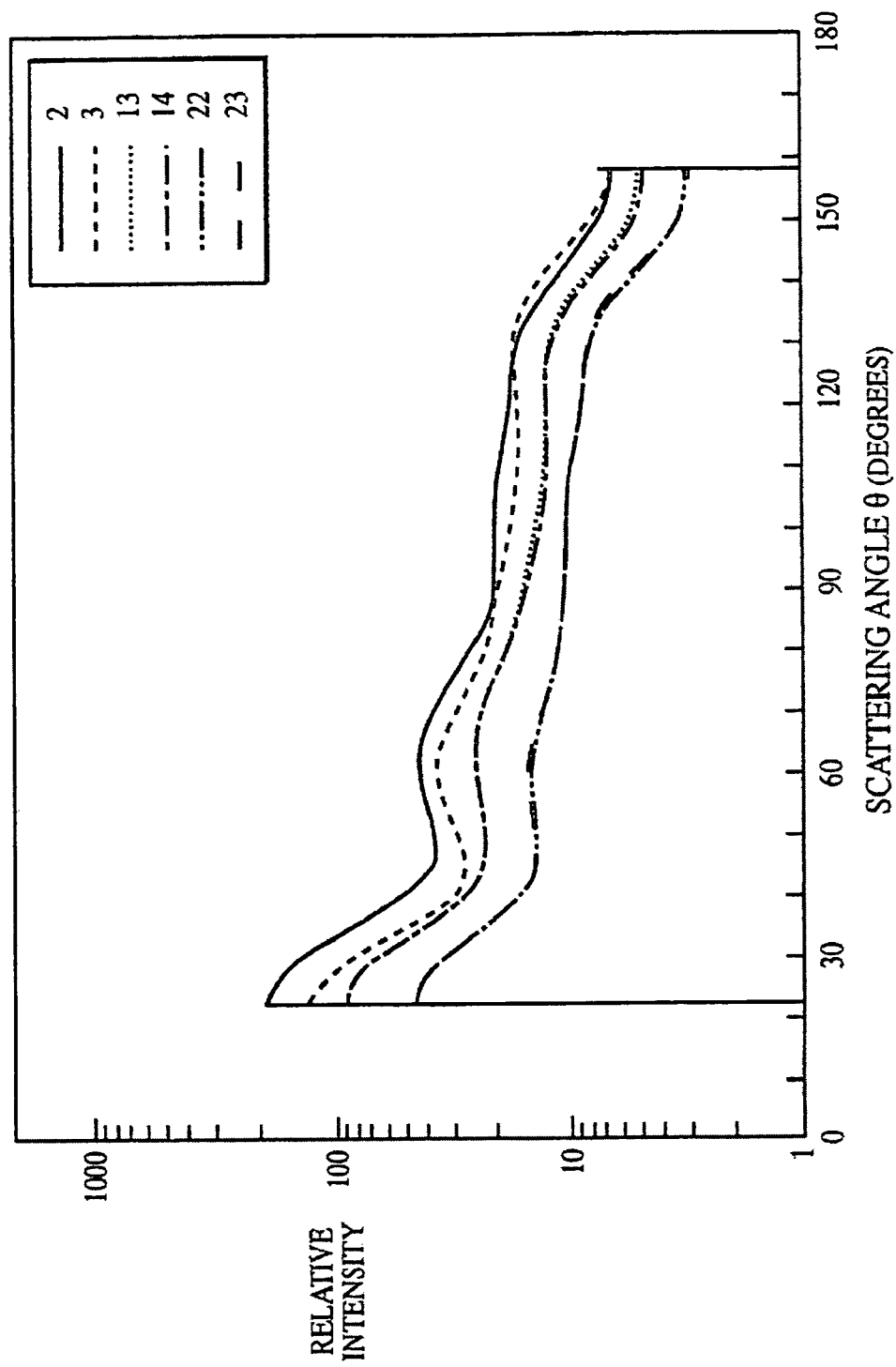
Figure 8B:
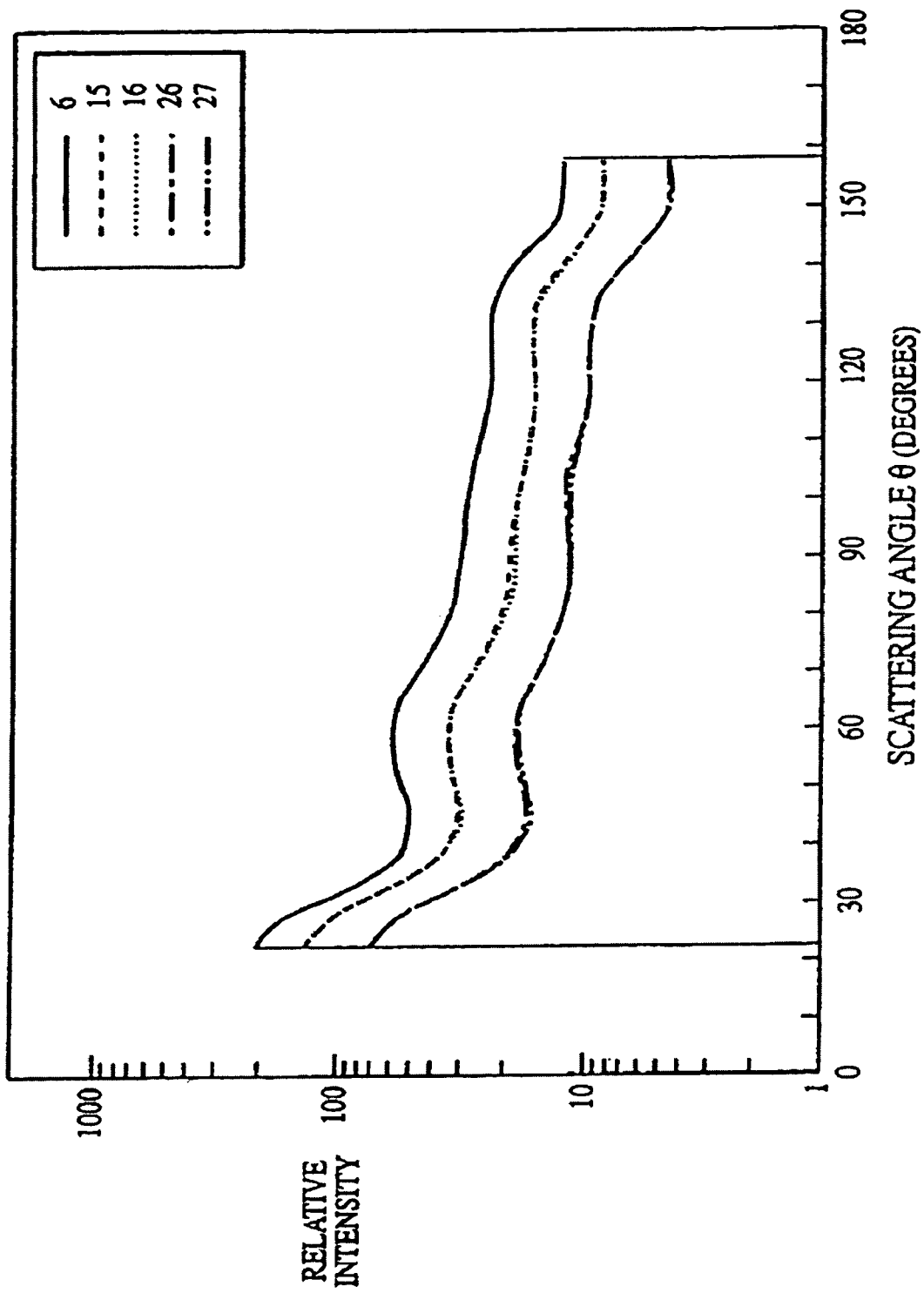
Figure 8C:
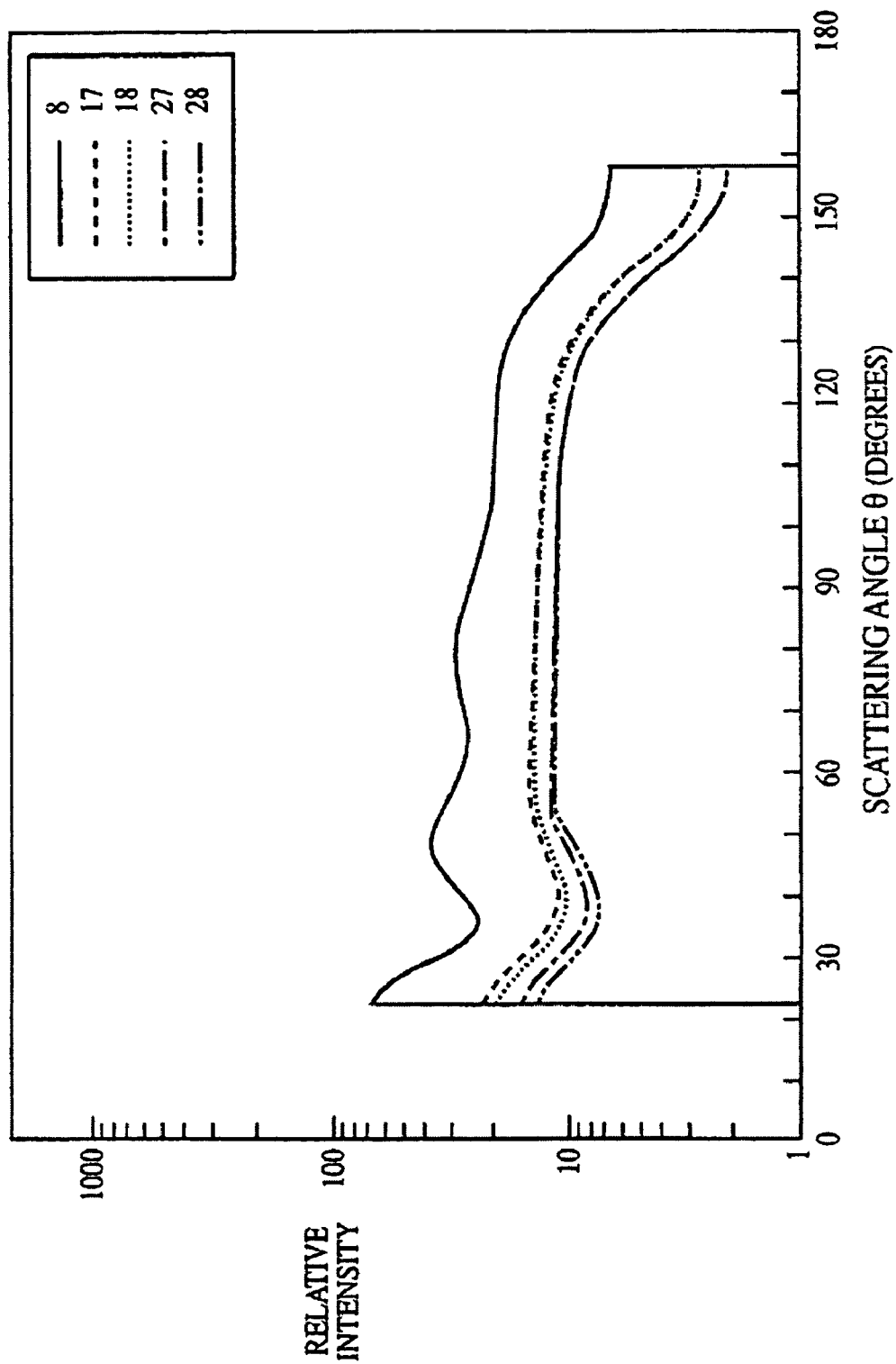

FIGS. 8A, 8B, and 8C are representative MALS graphic data demonstrating the relative decreases in intensities at each scattering angle following incomplete (2 minutes) and complete (15 minutes) autoclave sterilization. These data are representatives of the average MALS measurements summarized in Tables 1A-1C in the column entitled "MALS Average Intensity."

The data disclosed herein (FIGS. 9A-C) demonstrate the growth of *B. subtilis* (Difco) (FIG. 9A), *B. subtilis* 168WT (FIG. 9B), and *B. stearothermophilus* (FIG. 9C) during 4 hours of incubation in 5% (w/v) BHI broth. The growth of the controls of *B. subtilis* strains was extensive during this same incubation period, whereas that of *B. stearothermophilus*, although positive, was slow. The bacterial counts of the two-minute autoclaved *B. subtilis* cultures also increased during the four hours of incubation, demonstrating that the spores had not been killed, whereas the cultures inoculated with spores autoclaved for 15 minutes failed to show an increase in cell growth. However, neither of the cultures of *B. stearothermophilus* spores which were autoclaved (i.e., 2 or 15 minutes), exhibited growth over the four-hour period (FIG. 9C).

FIG. 10 depicts a representative MALS graph obtained using *B. subtilis*-Difco untreated control depicting both the transition from a spore to a vegetative form (e.g., rod) at 2 hours of incubation and then continued growth over a three hour period. These data are representative of the MALS data for the control culture disclosed in graphical form in FIG. 9A.

Figure 9A:
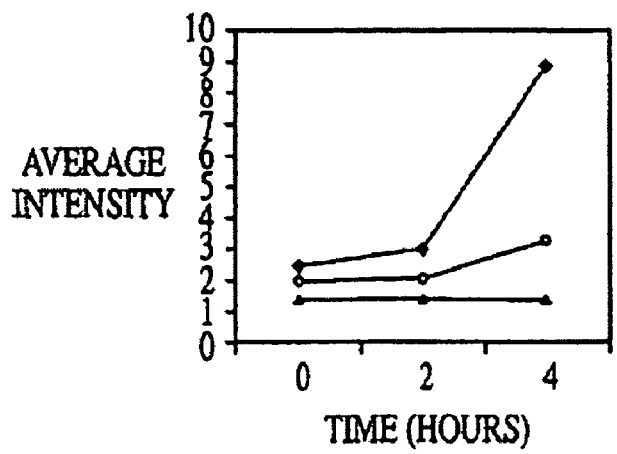
Figure 10:
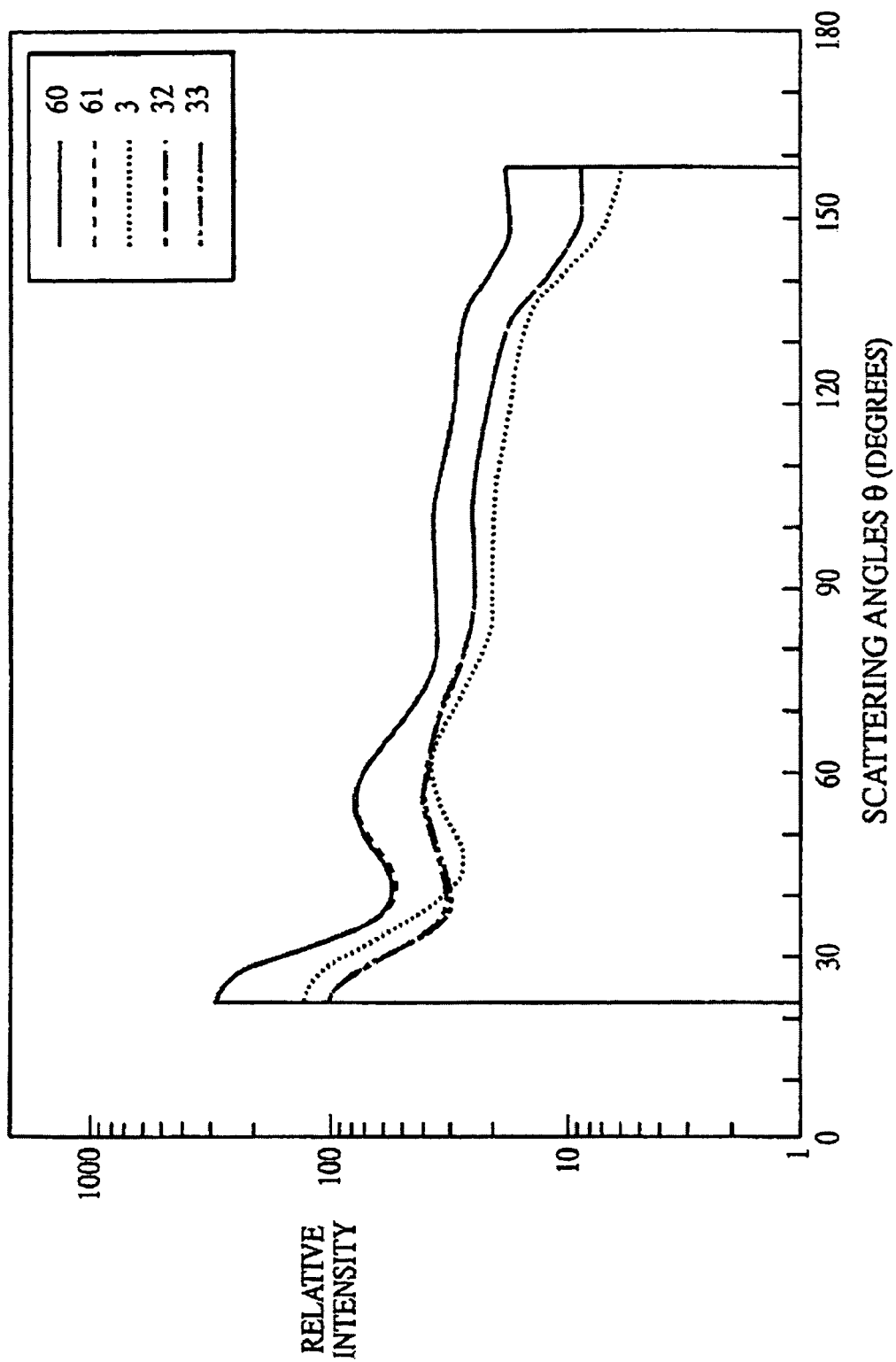
Figure 11:
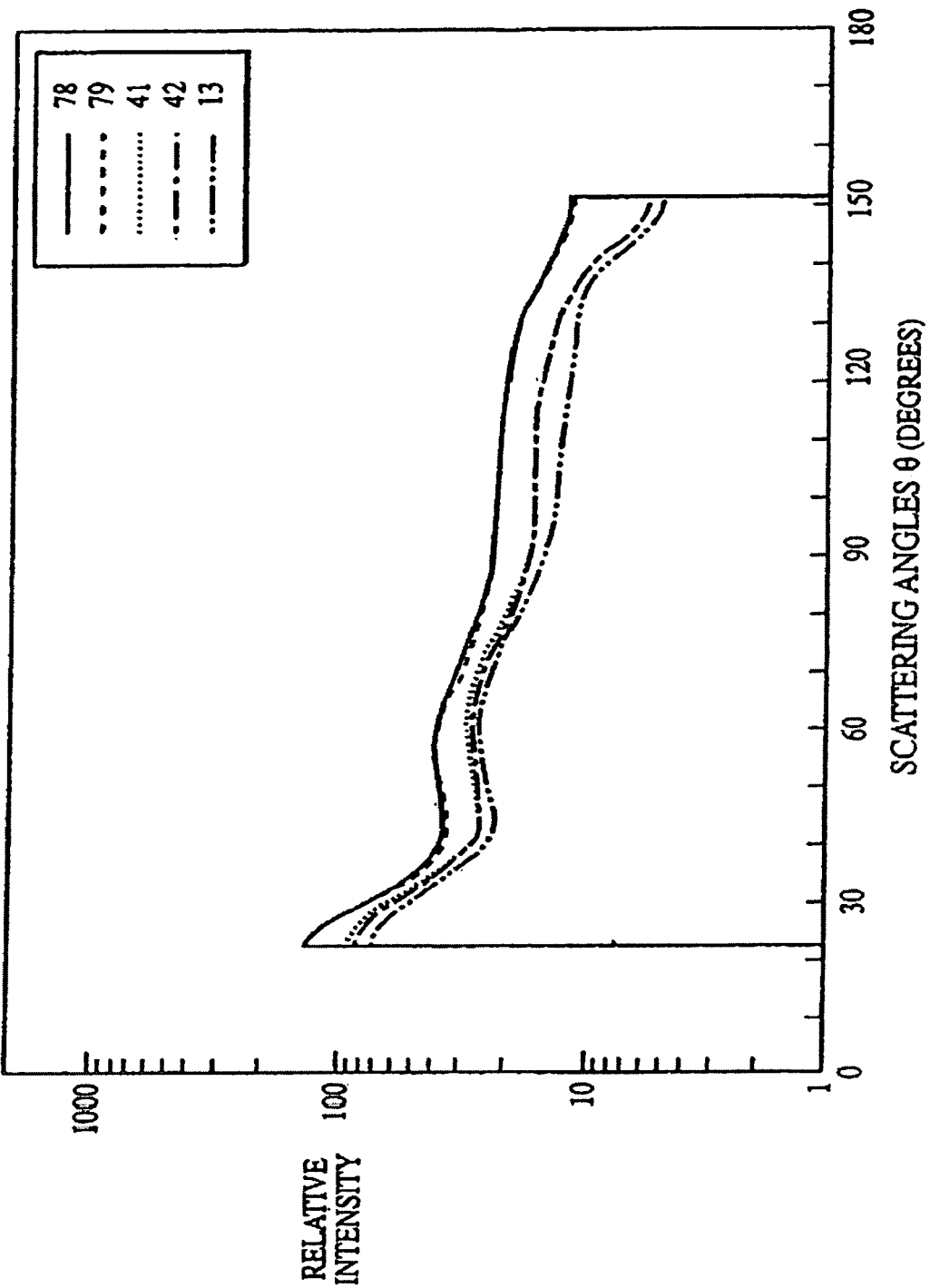

FIG. 11 depicts a representative MALS data set from the same data file disclosed in graphical form in FIG. 9A. That is, FIG. 11 depicts the MALS data for *B. subtilis*-Difco spores autoclaved for 2 minutes and incubated for 0, 2, or 4 hours. The data disclosed demonstrate the transition and growth of the 2 minute autoclaved culture. These data are summarized in FIG. 9A.

Figure 12:
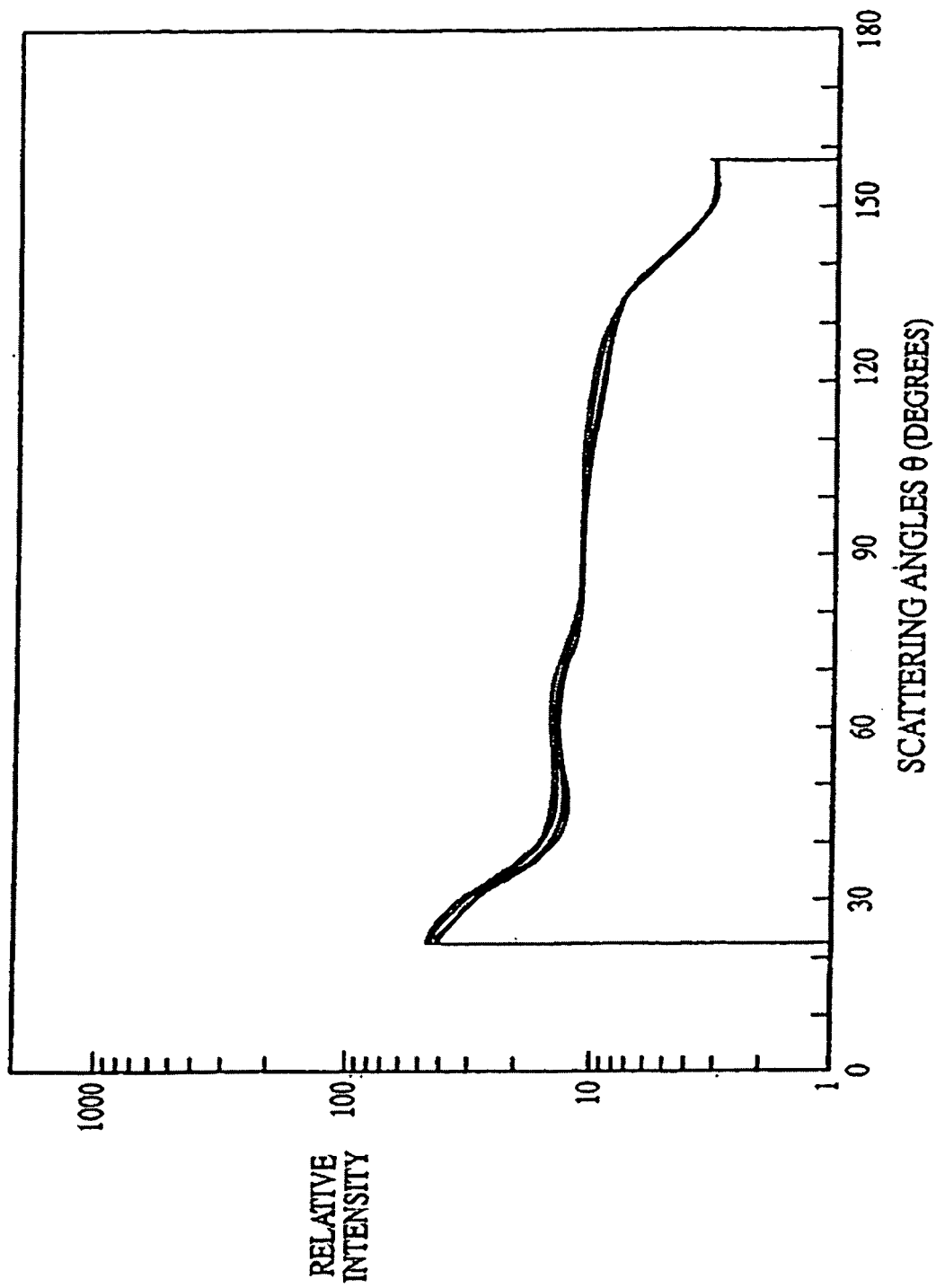

FIG. 12 is a representative MALS data set from the same data file disclosed in graphical form in FIG. 9A. That is, FIG. 12 depicts the MALS data obtained from a culture of *B. subtilis*-Difco spores autoclaved for 15 minutes and incubated for 0, 2, or 4 hours. The data disclosed herein demonstrate that the culture of spores autoclaved for 15 minutes failed to make a transition from the spore and consequently failed to grow. These data are summarized in FIG. 9A.

Figure 9B:
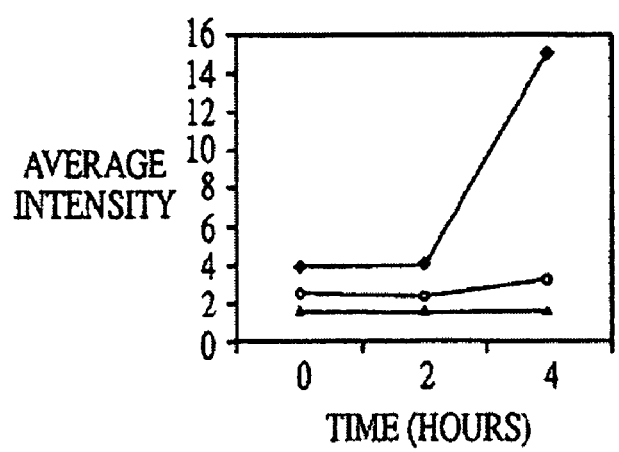
Figure 9C:
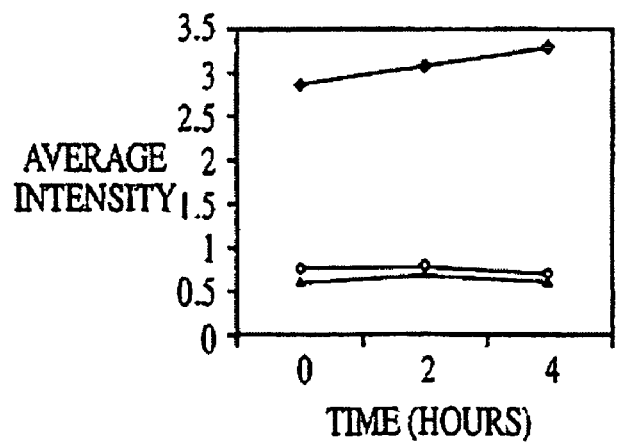

FIG. 9B summarizes the data obtained on the effect of steam sterilization on the growth of *B. subtilis* 168WT spores. The data obtained using *B. subtilis* 168WT spores is similar to that obtained using *B. subtilis* Difco spores (FIG. 9A). For *B. subtilis* 168WT spores which were not treated (control, ♦) and then incubated in culture for 0, 2 or 3 hours, the data disclosed herein demonstrate the transition from a spore to a vegetative form at 2 hours and then continued growth over a three hour period (FIG. 9B, ♦).

The data disclosed herein demonstrate the growth of *B. subtilis* 168WT spores which were autoclaved for two minutes and then incubated for 0, 2, or 4 hours after treatment. The data disclosed herein demonstrate the transition and growth of the 2 minutes autoclaved culture (FIG. 9B, ○).

The data disclosed herein further demonstrate the effect of 15 minutes (i.e., complete) steam sterilization on *B. Subtilis* 168WT spores (FIG. 9B, ▲). The data disclosed herein demonstrate that the 15 minutes autoclaved culture failed to make a transition from the spore and consequently failed to grow (FIG. 9B, ▲).

FIG. 9C depicts the effect of steam sterilization on *B. stearothermophilus* spores. The data depicted herein demonstrate that the control, untreated *B. stearothermophilus* spores grew very slowly demonstrating little change in average intensity over 4 hours incubation (FIG. 9C, ♦). Moreover, the data demonstrate that *B. stearothermophilus* spores autoclaved for 2 minutes (▲) exhibited growth characteristics which were nearly identical to spores autoclaved for 15 minutes (O). More specifically, there was essentially no growth in either culture over a period of four hours (FIG. 9C, ○ and ▲ and Table 1C).

Without wishing to be bound by any particular theory, these results are surprising given that *B. stearothermophilus* is a thermophilic bacterium and that it is believed that its spores would be more resistant to heat-based sterilization methods than those of non-thermophilic bacteria such as *B. subtilis*. Instead, the data disclosed herein suggest that the spores of *B. stearothermophilus* are more sensitive to steam sterilization since 2 minutes of autoclaving had a greater effect on the growth of these spores than on *B. subtilis* spores autoclaved for the same period of time. That is, CFU data demonstrate that 2 minutes of autoclaving killed approximately 50% of *B. subtilis* (Difco) spores (Table 1A), 76% of *B. subtilis* 168WT spores (Table 1B), and over 99% of *B. stearothermophilus* spores (Table 1C). These data are confirmed further by the MALS data depicted in FIGS. 9A, B, and C.

These data are surprising in light of the art-recognized acceptance of *B. stearothermophilus* as the "industry standard" biological indicator for heat-based sterilization treatment. Therefore, the data disclosed herein suggest, for the first time, that the BI of the present invention using *B. subtilis* in conjunction with the MALS detection system is a better BI than prior art methods using *B. stearothermophilus* as a BI of steam sterilization.

Ocean Optics Model USB-2000

Figure 15:
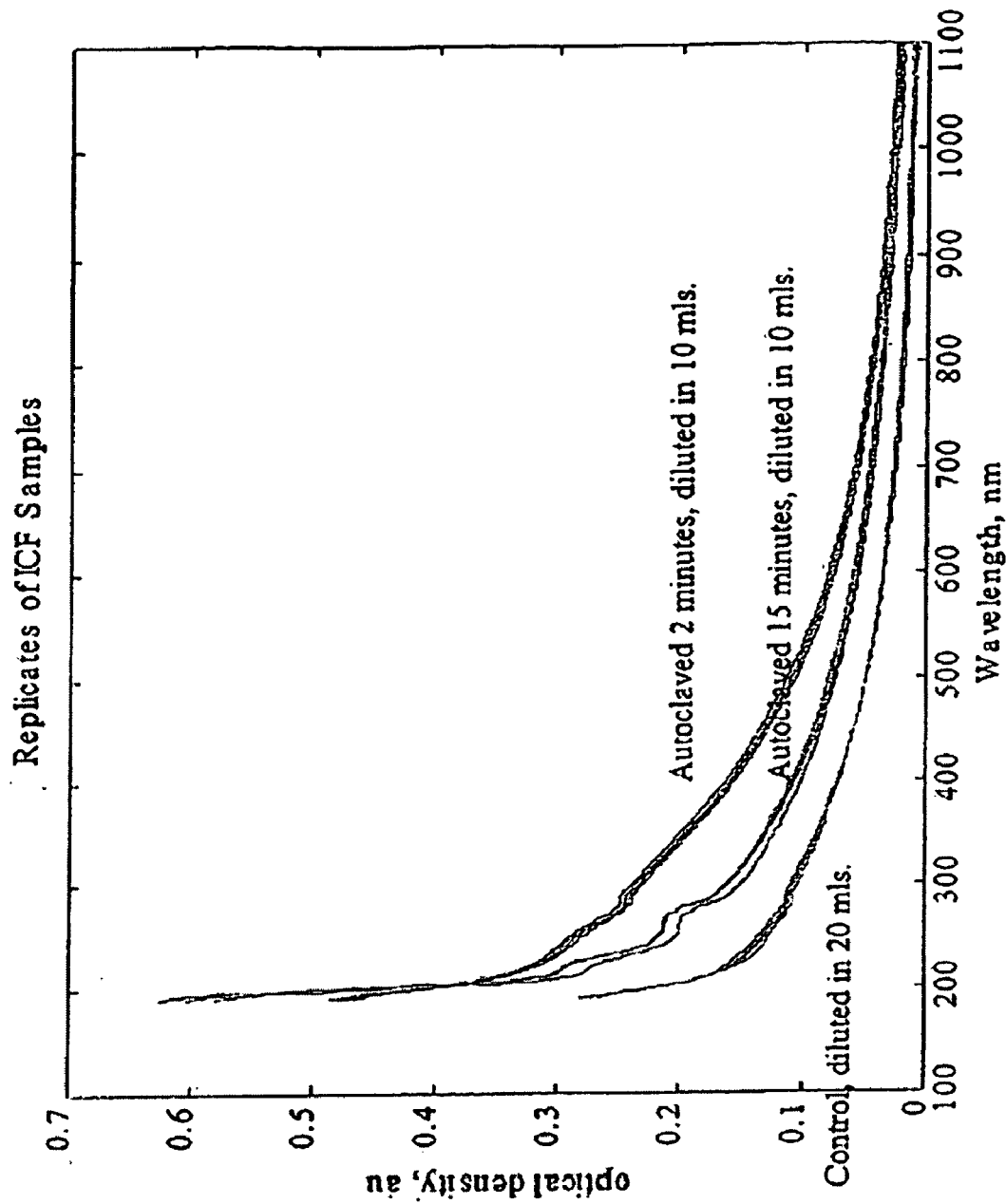
FIG. 15 is a graph depicting the optical density as a function of the wavelength to demonstrate the increase in size and number of cells.
Figure 17:
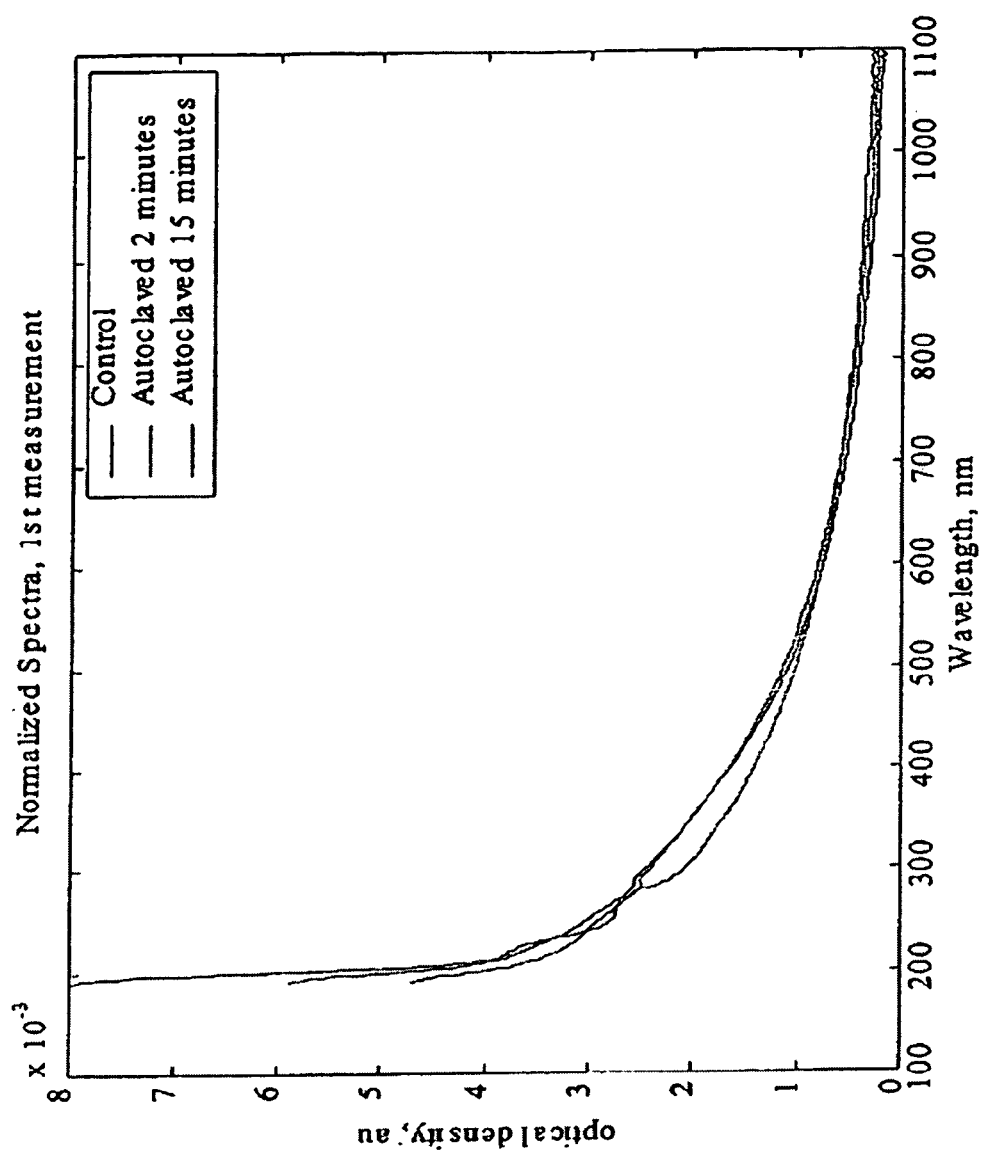
FIG. 17 is a graph depicting the optical density as a function of wavelength to demonstrate the difference in optical densities of control spores versus those autoclaved for 2 or 15 minutes.
Figure 18:
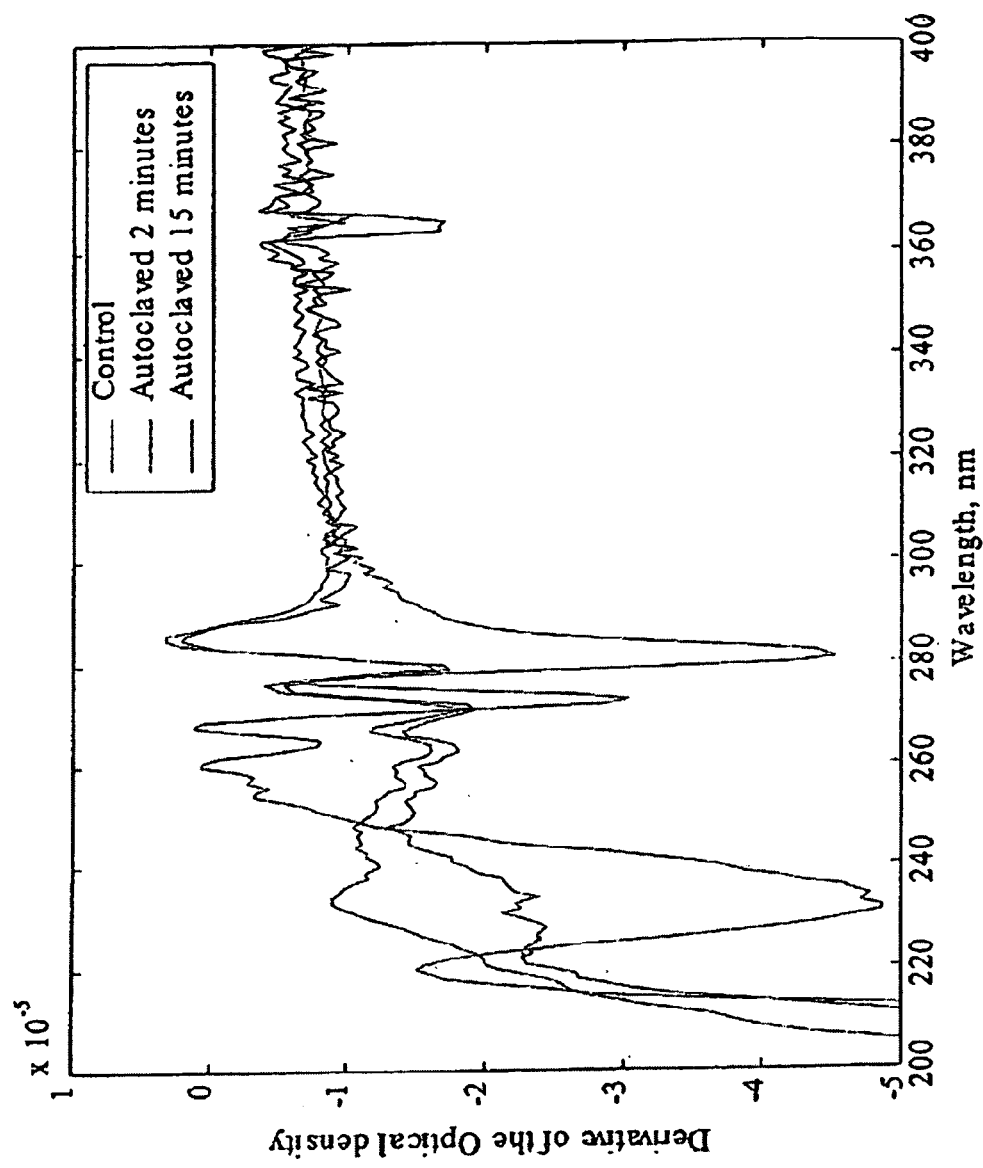
FIG. 18 is a graph depicting the derivative of the optical densities of spores plotted against the wavelength for normal spores and those autoclaved for 2 or 15 minutes.
Figure 19:
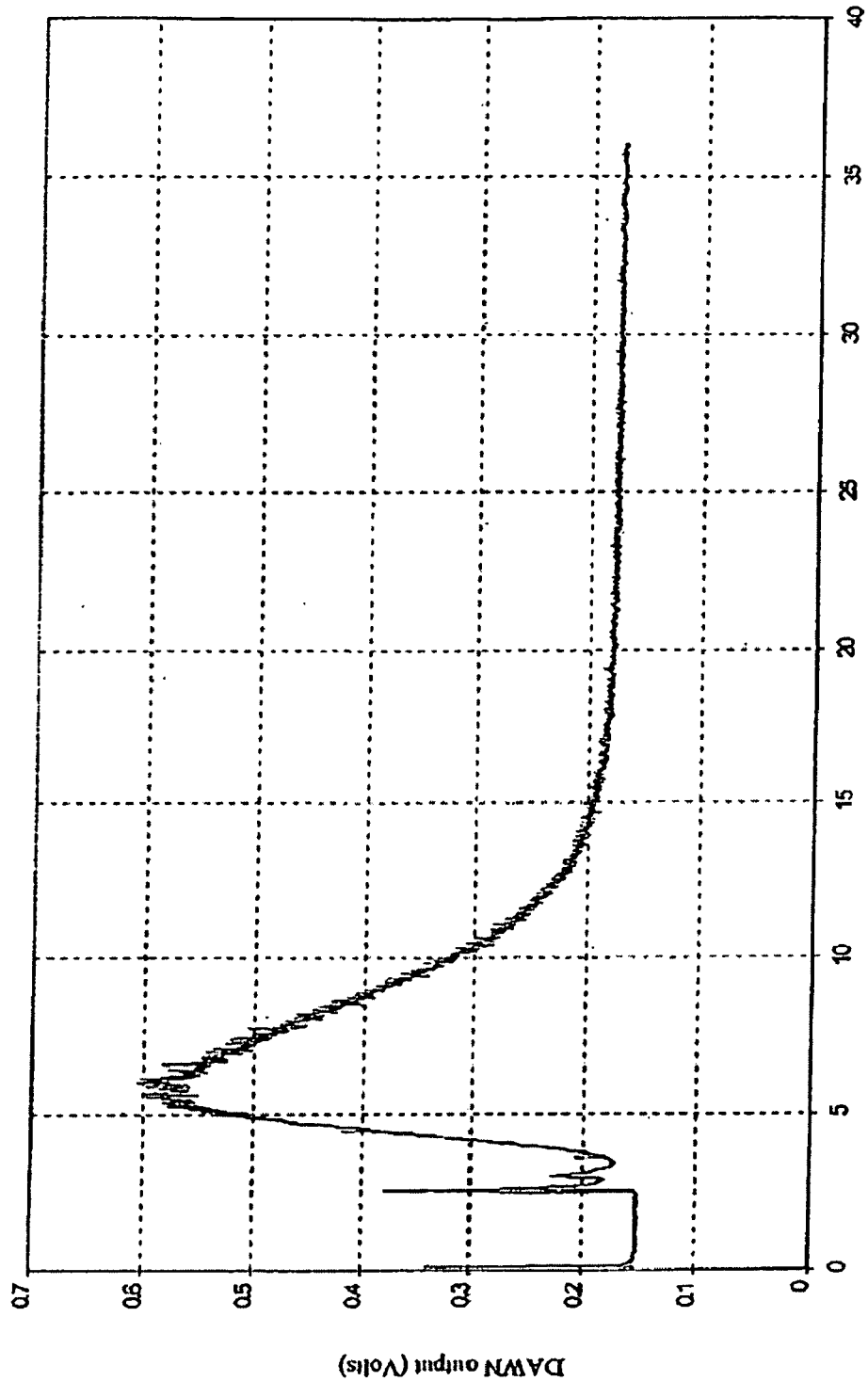
FIG. 19 depicts the fractionation curve of *B. subtilis* as a function of the output in Volts of a DAWN spectrophotometer as a function of elution time in minutes.
Figure 20:
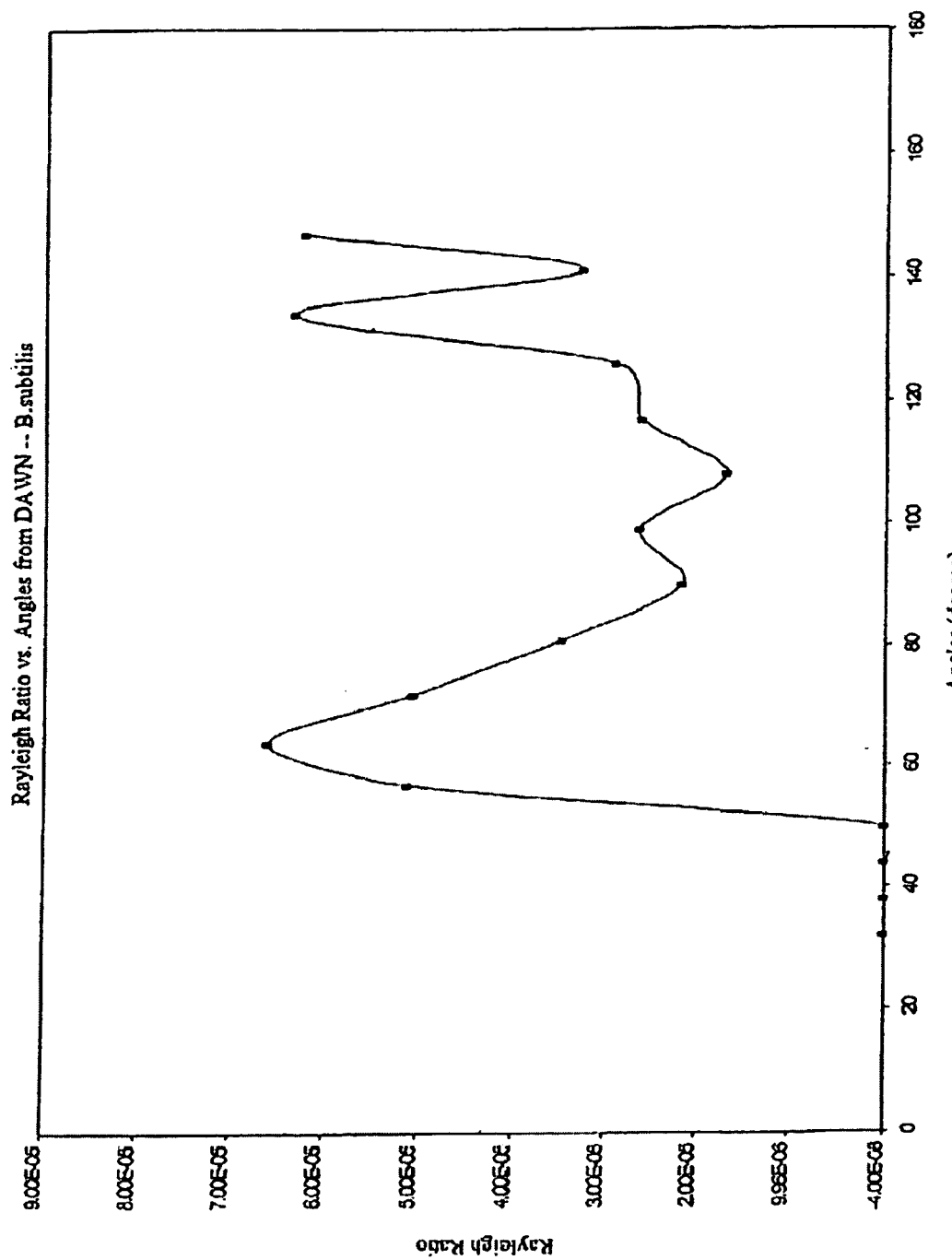
FIG. 20 depicts the Rayleigh Ratio as a function of the angles used in a DAWN spectrophotometer for *B. subtilis* spores.
Figure 21:
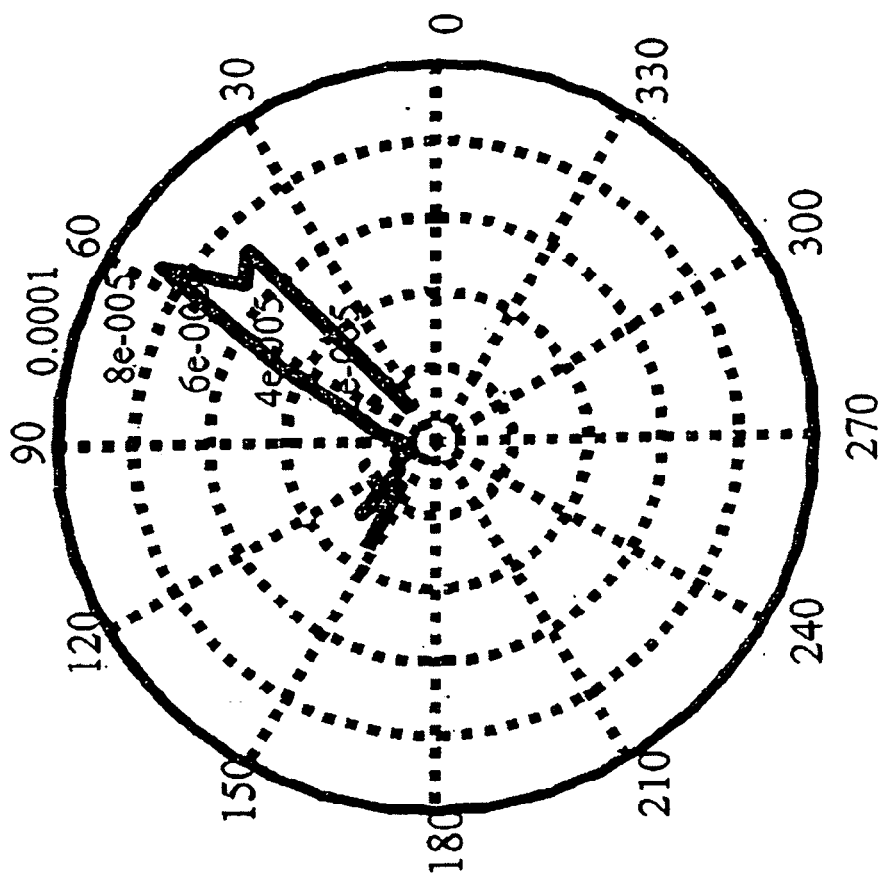
FIG. 21 is a polar plot of *B. globigii* demonstrating the effect of the spectrophotometer at different angles.
Figure 22:
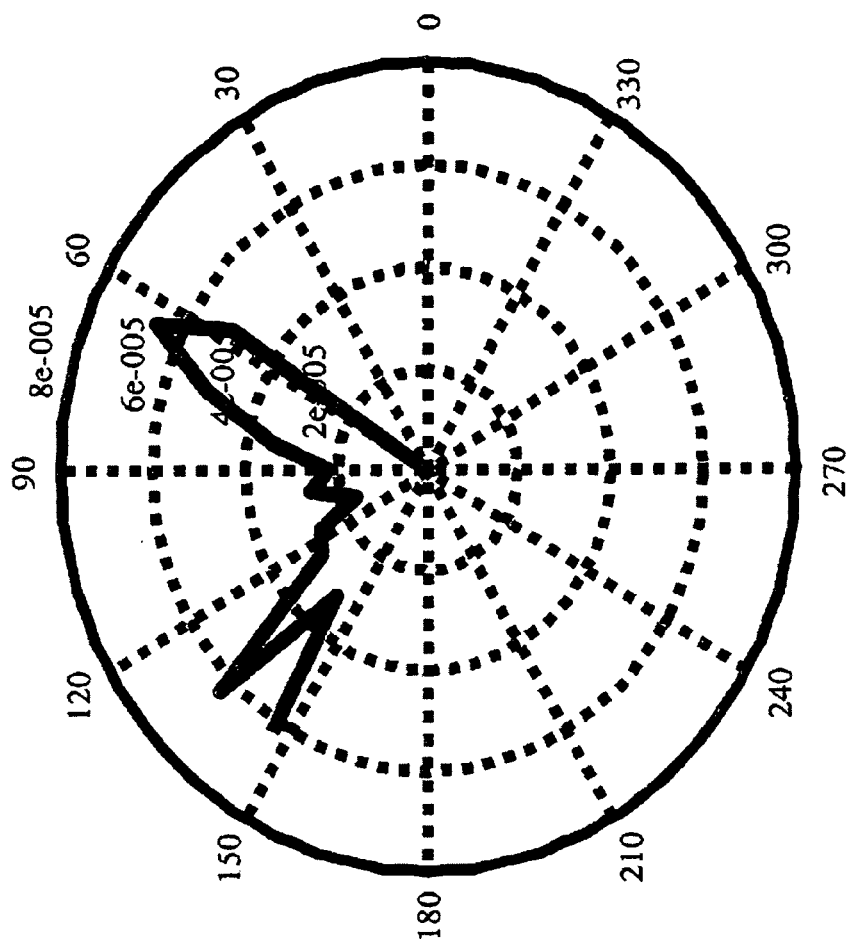
FIG. 22 is a polar plot of *B. subtilis* demonstrating the effect of the spectrophotometer at different angles.
Figure 23:
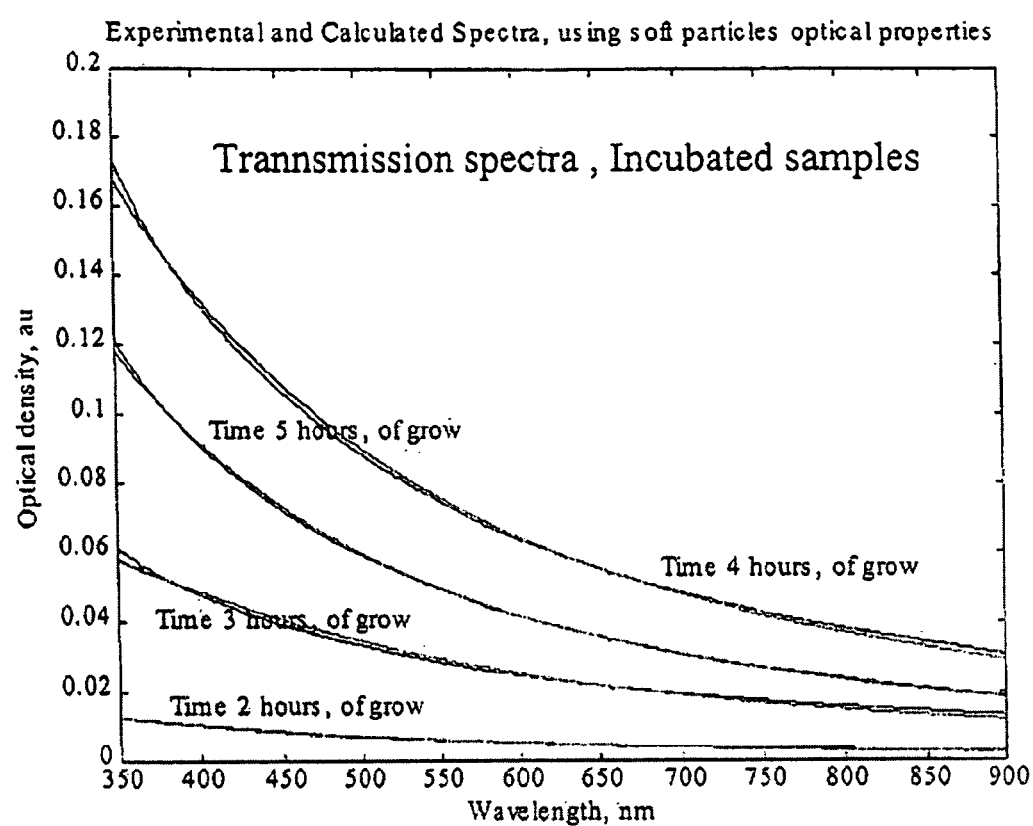
FIG. 23 depicts a graphical representation of the optical density as a function of wavelength for incubated spore samples at various growth time periods including both experimental and calculated spectra.

Germinating spores were monitored for growth over a period of 5 hours after heat-shocking at 70° C. for 8 minutes and growth in 5% Brain Heart Infusion broth. FIG. 15 shows that there is an increase in the number of cells over time. The data was analyzed to show the size of the cells at each interval as well as the number of cells and their concentration in grams/ml. A printout of the analyzed data from FIG. 15 is shown in FIG. 16. What is seen is that the number of organisms increase over time as expected, i.e, from $2.3 \times 10^5$/ml to $1.9 \times 10^7$/ml over a three-hour period. These data are in agreement with other data in which plate counts are done over this time period. This experiment shows that the instrument data can be converted into a form in which the number of bacteria a their characteristics can be determined. FIG. 17 shows the difference in optical densities of control spores versus those autoclaved for 2 or 15 minutes. There is a decrease in the optical densities at the various wavelengths that corresponds to the time of autoclaving. FIG. 18, which is a derivative of the optical densities of normal spores versus those autoclaved for 2 or 15 minutes, shows that spores autoclaved for 2 minutes have changed but still have a profile similar to that of control spores, whereas spores autoclaved for 15 minutes have profiles that differ greatly from either control or 2-minute autoclaved spores. From the peaks and valleys in the spectrum from 220 to about 290 nm, the optical densities in the DNA (260 nm) and protein/amino acid absorbing regions (280 nm) are especially quite different for the spores autoclaved for 15 min. This result indicates that spore DNA is now released from the cortex and that there is a loss in protein, amino acids and other macromolecules as a result of the spore collapsing/rupturing due to the steam under pressure during autoclaving.

Ozone Sterilization

Figure 13:
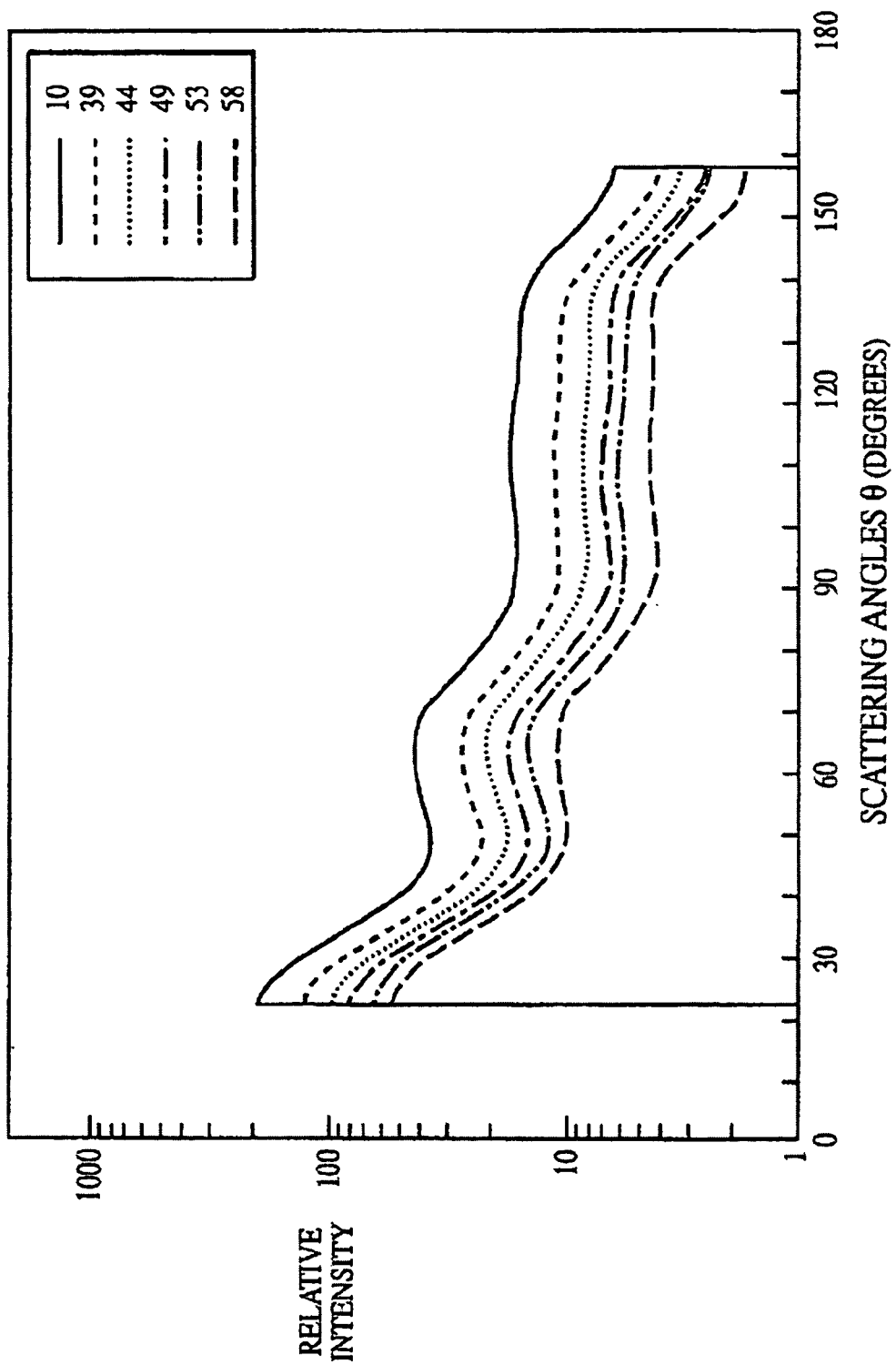

Ozone treatment of microbes is representative of cold sterilization and disinfection. We were able to show that a concentration dependent dose response could be achieved when *Bacillus* spores were exposed to an $O_3$ concentration of 0.3 to 0.35 ppm for varying exposure times. *Bacillus subtilis* spores, at an concentration of $2 \times 10^6$ spores/milliliter were exposed to ozone at treatment times of 0, 5, 10, 15, 20, and 30 minutes, at which times they were measured by MALS, AODC, and CFU, respectively. All measurements were made on spores immediately and without the need for incubation. FIG. 13, which represents MALS measurements made on ozonated *B. subtilis* spores, shows that there is a reduction in the relative intensities at all scattering angles. These measurements could be correlated directly with the cumulative concentration of ozone with increasing time of exposure. For example, the CT (concentration x time) value for ozone that kills 41.4% of the spore population (reduction in viable spores from $2.1 \times 10^6$ to $1.23 \times 10^6$ spores/ml) is 0.3 ppm×5 min=1.5. For a kill of 91% (reduction from $2.1 \times 10^6$ to $1.8 \times 10^3$ spores/ml) the CT is 0.3 ppm×15 min=4.5. For a kill of 99.995% (reduction from $2.1 \times 10^6$ to 10 spores/mL), it is 0.3 ppm×30 min=9.

Table 2 gives a direct comparison of MALS, AODC, and CFU data for ozone treatment of *B. subtilis* spores over at 5-minute intervals over a 30-min period. All MALS and AODC measurements were made on spores immediately after treatment, and in the absence of incubation. Spores were plated immediately onto Trypticase Soy Agar after treatment to verify the number of surviving spores (CFU).

*B. stearothermophilus* spores were also exposed to 0.3 ppm of ozone, but it was shown that between 15 and 20 minutes of exposure gave a kill comparable to a 30 minute ozone exposure for *B. subtilis*. MALS measurements on these spores made immediately after ozone treatment and in the absence of any incubation are presented in FIG. 14.

Ozone treatment of microbes is representative of cold sterilization and disinfection. The data disclosed herein (Table 2) demonstrates the evaluation of cold (e.g., ozone) sterilization using MALS, AODC, and CFU directly after treatment without post-treatment incubation. The data disclosed herein demonstrate the effect of treatment of *B. subtilis*-Difco spores with 0.3 parts per million (ppm) of ozone for treatment times of 0, 5, 10, 15, 20, and 30 minutes.

TABLE 2

| Treatment | MALS | | AODC | | CFU | | |
| --- | --- | --- | --- | --- | --- | --- | --- |
| Time (minutes) | Intensity | % of control | Spores per ml | % of control | CFU/ml | % of Control | % of AODC |
| 0 | 2436.6 | 100 | $2.34 \times 10^6$ | 100 | $2.10 \times 10^6$ | 100 | 100 |
| 5 | 1591.92 | 65.33 | $1.6 \times 10^6$ | 68.3 | $1.23 \times 10^6$ | 58.5 | 76.9 |
| 10 | 1264.26 | 51.89 | $1.16 \times 10^6$ | 49.5 | $1.68 \times 10^5$ | 8.0 | 14.5 |
| 15 | 1039.64 | 42.67 | $1.29 \times 10^6$ | 55.1 | $1.80 \times 10^3$ | 0.09 | 0.14 |
| 20 | 851.5 | 34.94 | $4.87 \times 10^5$ | 20.8 | $1.82 \times 10^2$ | 0.009 | 0.04 |
| 30 | 681.2 | 27.96 | $5.03 \times 10^5$ | 21.5 | 10 | 0.00005 | 0.04 |

Note.
Average intensity is the log weighted average of intensities at all detectors. Colony forming units (CFU) were determined after 24 hours incubation.

MALS, AODC, and CFU data were evaluated just as was done for steam sterilization as disclosed previously elsewhere herein. Spore suspensions of about $2 \times 10^6$ spores per milliliter were ozonated at a dose of approximately 0.35 ppm after which time MALS measurements were performed. AODC slides and TSA plate counts were made for each of the treated and control suspensions. The results of all measurements were performed in parallel, demonstrating that decreases in the spore concentrations were consistently greater with increasing exposure to ozone. The MALS data disclosed in FIG. 13 is a representative MALS printout for the data summarized in Table 2. The data disclosed herein demonstrate that in addition to the data previously disclosed elsewhere herein for autoclaving, ethylene oxide and hydrogen peroxide sterilization treatment, the BI of the present invention is effective in ascertaining the efficacy of ozone sterilization/disinfection treatment. Similar to the data disclosed previously elsewhere herein, the BI of the present invention provides immediate results demonstrating the efficacy of various sterilization treatments without the need to wait for culture methods requiring lengthy incubation periods.

Because of the unexpected results obtained using B. stearothermophilus to assess the efficacy of steam sterilization as disclosed previously elsewhere herein, the effect of ozonation upon these spores was assessed using MALS detection.

Figure 14:
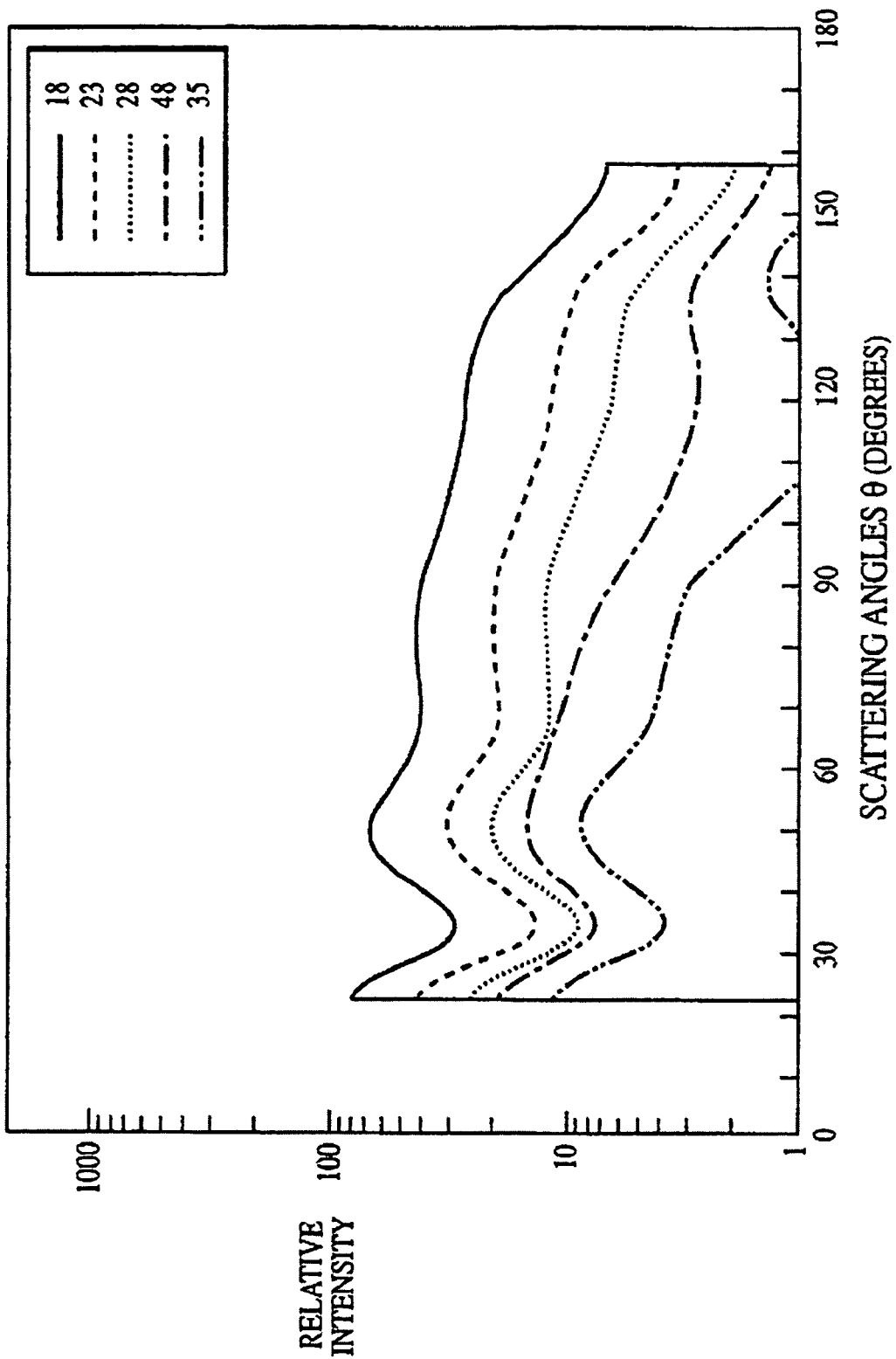

FIG. 14 depicts the results obtained using the same ozone treatment protocol with B. stearothermophilus spores as was used with B. subtilis (Difco) spores at about 0.3 ppm ozone. As was the case for B. subtilis spores, the data disclosed herein demonstrate that there were decreases in spore concentrations with increasing exposure to ozone.

The results of comparing the MALS measurements with AODC and viable counts (CFU) show that this method is capable of assessing the efficacy of either steam sterilization or ozone sterilization/disinfection. Although the DAWN-F (Wyatt Technology Corp.) and the Ocean Optics Model USB-2000 instruments measure different parameters, both are capable of showing a difference between normal (control) spores and those treated with ozone or autoclaved. The collapsed structure of the treated spore (seen by scanning electron microscopy) and changes in the macromolecular structure revealed at least in the ultraviolet absorbance region using Ocean Optics Model USB-2000, make it possible to differentiate between a killed or viable spore. We can therefore determine whether sterilization has been complete or whether there are still viable spores by the ratio of damaged to normal spores, and this is accomplished without the necessity of incubation and growth of a biological indicator organism (e.g. B. subtilis or B. stearothermophilus).

The disclosures of each and every patent, patent application, and publication cited herein are hereby incorporated herein by reference in their entirety.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A system for detecting effectiveness of a sterilization treatment, comprising a biological indicator, a solid support, a liquid medium, and a multi-angle light scattering instrument which generates a multi-angle light scattering profile of the biological indicator, a first multi-angle light scattering profile of the biological indicator prior to a sterilization treatment and a second multi-angle light scattering profile of the biological indicator after a sterilization treatment.

2. The system of claim 1, wherein the biological indicator is a spore selected from the group consisting of a B. subtilis spore, and a B. stearothermophilus spore.

3. The system of claim 2, wherein the biological indicator is a B. subtilis spore.

4. The system of claim 1, wherein the solid support is selected from the group consisting of an adsorbent filter, a membrane, a matrix, glass, plastic, and metal.

5. The system of claim 4, wherein the support is glass in the form of a glass slide or a glass vial.

6. The system of claim 1, wherein the multi-angle light scattering instrument is a multi-angle light scattering photometer.

7. The system of claim 1, wherein the sterilization treatment is selected from the group consisting of a chemical sterilization treatment, and a physical sterilization treatment.

8. The system of claim 7, wherein the chemical sterilization treatment is selected from the group consisting of an ethylene oxide sterilization treatment, a hydrogen peroxide sterilization treatment, a tetrasilver tetraoxide sterilization treatment, and an ozone stenhzation treatment.

9. The system of claim 7, wherein the physical sterilization treatment is selected from the group consisting of a radiation sterilization treatment, a gas plasma sterilization treatment, a steam sterilization treatment, and a dry heat sterilization treatment.

10. The system of claim 1, wherein the liquid medium is selected from the group consisting of water, a brain heart infusion broth medium, a nutrient broth, and a trypticase soy broth.

* * * * *